United States Patent
Yin et al.

(10) Patent No.: US 10,449,388 B2
(45) Date of Patent: Oct. 22, 2019

(54) SYSTEMS AND METHODS FOR SPECIFYING TREATMENT CRITERIA AND TREATMENT PARAMETERS FOR PATIENT SPECIFIC RADIATION THERAPY PLANNING

(71) Applicants: Duke University, Durham, NC (US); Wake Forest University Health Sciences, Winston-Salem, NC (US)

(72) Inventors: Fang-Fang Yin, Chapel Hill, NC (US); Qingrong Jackie Wu, Chapel Hill, NC (US); Lulin Yuan, Cary, NC (US); Yaorong Ge, Matthews, NC (US)

(73) Assignees: Duke University, Durham, NC (US); Wake Forest University Health Sciences, Winston-Salem, NC (US)

( * ) Notice: Subject to any disclaimer, the term of this patent is extended or adjusted under 35 U.S.C. 154(b) by 384 days.

(21) Appl. No.: 14/893,055

(22) PCT Filed: Jun. 18, 2014

(86) PCT No.: PCT/US2014/043022
§ 371 (c)(1),
(2) Date: Nov. 21, 2015

(87) PCT Pub. No.: WO2014/205128
PCT Pub. Date: Dec. 24, 2014

(65) Prior Publication Data
US 2016/0129282 A1 May 12, 2016

Related U.S. Application Data

(60) Provisional application No. 61/836,253, filed on Jun. 18, 2013, provisional application No. 61/891,941, filed on Oct. 17, 2013.

(51) Int. Cl.
*A61N 5/10* (2006.01)

(52) U.S. Cl.
CPC .......... *A61N 5/103* (2013.01); *A61N 5/1031* (2013.01); *A61N 2005/1074* (2013.01)

(58) Field of Classification Search
CPC ........ A61N 5/10; A61N 5/1031; A61N 5/103; A61N 2005/1041
(Continued)

(56) References Cited

U.S. PATENT DOCUMENTS

| 6,327,490 B1 | 12/2001 | Spetz |
| 6,430,307 B1 | 8/2002 | Souma et al. |

(Continued)

FOREIGN PATENT DOCUMENTS

| EP | 3384959 A1 | 10/2018 |
| WO | 03011390 A2 | 2/2003 |

OTHER PUBLICATIONS

European Patent Office Communication under Rule 71(3) Notice of Allowance issued in counterpart EP Application No. 14813397.8 dated Dec. 1, 2017 (one-hundred and one (101) pages).
(Continued)

*Primary Examiner* — Samuel G Gilbert
(74) *Attorney, Agent, or Firm* — Olive Law Group, PLLC

(57) ABSTRACT

Disclosed herein are systems and methods for specifying treatment criteria and treatment planning parameters for patient specific radiation therapy planning. According to an aspect, a method includes receiving data about a patient, computing geometric characterization of one or more organs at risk proximate to a target volume of a patient or vice versa, and selecting relevant treatment knowledge and experience. The method also includes generating, based on the received data, computed geometric characterization, and available knowledge and experience, a first set of radiation treatment planning parameters that will lead to a high quality plan for the patient. Further, the method includes model-
(Continued)

based prediction, based on the data, a second set or more of radiation treatment planning parameters that will lead to alternative achievable plans with different organ sparing objectives for treating the patient. The multiple sets for parameters can be used separately or in conjunction to generate treatment plans.

21 Claims, 39 Drawing Sheets

(58) Field of Classification Search
USPC .................................................. 600/1; 378/65
See application file for complete search history.

(56) References Cited

U.S. PATENT DOCUMENTS

| | | | |
|---|---|---|---|
| 6,882,702 | B2 | 4/2005 | Luo |
| 7,027,557 | B2 | 4/2006 | Llacer |
| 7,298,819 | B2 | 11/2007 | Dooley et al. |
| 7,362,848 | B2 | 4/2008 | Saracen et al. |
| 7,590,219 | B2 | 9/2009 | Maurer, Jr. et al. |
| 7,693,257 | B2 | 4/2010 | Allison |
| 8,976,929 | B2 | 3/2015 | Wu et al. |
| 2002/0080915 | A1 | 6/2002 | Frohlich |
| 2004/0208341 | A1 | 10/2004 | Zhou et al. |
| 2006/0274885 | A1 | 12/2006 | Wang et al. |
| 2006/0291621 | A1 | 12/2006 | Yan et al. |
| 2008/0008291 | A1 | 1/2008 | Alakuijala et al. |
| 2009/0228299 | A1 | 9/2009 | Kangarloo et al. |
| 2009/0295756 | A1 | 12/2009 | Shamaie |
| 2010/0208867 | A1* | 8/2010 | Nord ............... A61N 5/103 378/65 |
| 2011/0130614 | A1 | 6/2011 | Schulz et al. |
| 2011/0153547 | A1 | 6/2011 | McNutt et al. |
| 2012/0014507 | A1* | 1/2012 | Wu ............... A61N 5/10 378/65 |
| 2012/0190912 | A1 | 7/2012 | McKenna et al. |
| 2012/0226152 | A1 | 9/2012 | Porikli |
| 2013/0034050 | A1 | 2/2013 | Ros et al. |
| 2013/0035582 | A1 | 2/2013 | Radulescu et al. |
| 2013/0077752 | A1 | 3/2013 | Zankowski |
| 2013/0090549 | A1 | 4/2013 | Meltsner et al. |
| 2013/0197878 | A1 | 8/2013 | Fiege et al. |
| 2013/0289332 | A1 | 10/2013 | Purdie et al. |
| 2014/0205128 | A1 | 7/2014 | Spoettl et al. |
| 2014/0350863 | A1 | 11/2014 | Hartman et al. |
| 2015/0087879 | A1 | 3/2015 | Nelms |
| 2015/0238158 | A1 | 8/2015 | Zhou et al. |
| 2016/0129282 | A1 | 5/2016 | Yin et al. |

OTHER PUBLICATIONS

Chinese (State Intellectual Property Office of People's Republic of China) Office Action for Application No. 201480034786.7 dated Sep. 20, 2017.

International Search Report on Patentability for Application No. PCT/US2016/021272 dated Sep. 12, 2017.
Extended European Search Report dated Dec. 20, 2016 received in EP 14813397.8.
International Search Report and Written Opinion with respect to related PCT Application No. PCT/US2016/21272 dated Jun. 10, 2016.
International Search Report and Written Opinion with respect to related PCT Application No. PCT?US2016/21271 dated Jun. 27, 2016.
PCT International Search Report dated Oct. 16, 2014 for PCT Patent Application PCT/US2014/043022.
Decision of Rejection issued in counterpart Chinese Application No. 201480034786.7 dated Jul. 6, 2018 (two (2) pages).
Office Action issued in counterpart CN Application No. 201480034786.7 dated Mar. 8, 2018.
Extended European Search Report issued in counterpart EP Application No. 18170881.9 dated Jun. 29, 2018, (five (5) pages).
Decision to Grant a European Patent Pursuant to Article 97(1) EPC issued in counterpart EP Application No. 14813397.8 dated Apr. 12, 2018. (two (2) pages).
International Preliminary Report on Patentability and Written Opinion issued in PCT Application No. PCT/US16/063204 dated May 22, 2018, (six (6) pages).
Corrected Notice of Allowability issued in issued in U.S. Appl. No. 13/184,746 dated Jan. 9, 2015.
Final Office Action issued in U.S. Appl. No. 13/184,746 dated Feb. 14, 2014.
Non-Final Office Action issued in U.S. Appl. No. 13/184,746 dated Aug. 21, 2014.
Non-Final Office Action issued in U.S. Appl. No. 13/184,746 dated Oct. 3, 2013.
Notice of Allowance issued in U.S. Appl. No. 13/184,746 dated Oct. 31, 2014.
Request for Continued Examination filed in U.S. Appl. No. 13/184,746 dated Aug. 13, 2014.
Response to Non-Final Office Action filed in U.S. Appl. No. 13/184,746 dated Jan. 3, 2014.
Response to Non-Final Office Action filed in U.S. Appl. No. 13/184,746 dated Sep. 22, 2014.
Communication Pursuant to Rule 69 EPC issued in counterpart EP Application No. 18170881 dated Oct. 15, 2018 (two (2) pages).
Non-Final Office Action issued in counterpart U.S. Appl. No. 15/555,488 dated Mar. 22, 2019.
Communication under Rule 71(3) EPC issued in counterpart EP Application No. 18 170 881.9 dated May 21, 2019 (101 pages).
Notification of Re-examination issued in counterpart Chinese application No. 201480034786.7 dated Jun. 28, 2019 (six (6) pages).
Non-Final Office Action issued in counterpart U.S. Appl. No. 15/555,489 dated Jul. 23, 2019.

* cited by examiner

US 10,449,388 B2

SYSTEMS AND METHODS FOR SPECIFYING TREATMENT CRITERIA AND TREATMENT PARAMETERS FOR PATIENT SPECIFIC RADIATION THERAPY PLANNING

CROSS REFERENCE TO RELATED APPLICATIONS

This application is a 35 U.S.C. 371 application of PCT International Patent Application No. PCT/US2014/043022, filed Jun. 18, 2014 and titled SYSTEMS AND METHODS FOR SPECIFYING TREATMENT CRITERIA AND TREATMENT PARAMETERS FOR PATIENT SPECIFIC RADIATION THERAPY PLANNING, which claims priority to U.S. Provisional Patent Application No. 61/836,253, filed Jun. 18, 2013 and titled SYSTEMS AND METHODS FOR SPECIFYING TREATMENT CRITERIA AND TREATMENT PARAMETERS FOR PATIENT SPECIFIC RADIATION THERAPY PLANNING, and U.S. Provisional Patent Application No. 61/891,941, filed Oct. 17, 2013 and titled SYSTEMS AND METHODS FOR SPECIFYING TREATMENT CRITERIA AND TREATMENT PARAMETERS FOR PATIENT SPECIFIC RADIATION THERAPY PLANNING; the disclosures of which are incorporated herein by reference in their entireties.

TECHNICAL FIELD

The presently disclosed subject matter relates to radiation therapy. Particularly, the presently disclosed subject matter relates to systems and methods for specifying treatment criteria and treatment parameters for patient specific radiation therapy planning.

BACKGROUND

Radiation therapy, or radiotherapy, is the medical use of ionizing radiation to control malignant cells. In intensity-modulated radiation therapy (IMRT), the intensity or segment of the radiation is modified in accordance with a treatment plan to deliver highly conformal radiation doses to the planning target volume (PTV) of malignant cells, while sparing the surrounding organs at risk (OARs) and other healthy tissues from radiation damage. By dividing the PTV and OAR volumes into individual volume elements (or "voxels"), the IMRT treatment plan can be characterized by a three dimensional dose distribution that characterizes the magnitude of radiation at each of the voxels. Another effective, two dimensional representation of the dose distribution is the dose volume histogram (DVH). Many clinical toxicity data and guidelines relating radiation damage to organs and radiation dose are expressed in DVH parameters (i.e., x1% volume, or x2 cc volume exceeding y1% or y2 Gy of dose).

A plan is Pareto optimal if it is impossible to further improve a certain dosimetric parameter without compromising the other parameters. Pareto optimal plans can include a set of plans that satisfy different planning criteria and objectives. The term intensity-modulated radiation therapy (IMRT) treatment plan (or simply "IMRT plan") hereby includes all forms of treatment plans that utilize radiation treatment processes in which radiation intensity can be delivered in a non-uniform manner, including but not limited to: intensity modulate radiation therapy (IMRT), volumetric modulated arc therapy (VMAT), treatment plans designed using TOMOTERPAY™, ACCURAY™, proton therapy, VIEWRAY™, VERO™, etc.

The development of an intensity-modulated radiation therapy (IMRT) treatment plan (or simply "IMRT planning") typically involves a complex optimization procedure by which the radiation beam angles and strengths are designed to achieve required dose of radiation for the planning target volume as prescribed, as well as limit the radiation delivered to neighboring normal tissues. While a portion of the IMRT planning process may be performed via computerized optimization algorithms, typically much of the process requires the input and expertise of a human planner. The computerized optimization algorithm calculates the current-state dose distributions/DVHs of each PTV and OAR, and compares those values to the input dose/DVH objectives. The differences of these two sets dose/DVH values are used to adjust the strength of each radiation beamlet based on pre-determined formula.

In particular, the human planner is typically responsible for manually adjusting input planning dose objectives (e.g., dose limits, dose volume histogram [DVH] limits, etc.) via a time-consuming, iterative trial-and-error process. The trial-and-error nature of the process is due to the fact that the planner does not know whether or not a set of given dose objectives will result in a plan that meets all physician-prescribed goals for sparing organs at risk (known as "sparing goals"), or when it does, whether tradeoffs between planning target volume (PTV) coverage and sparing of organs at risk (OARs) can be further improved.

Further compounding the process is the fact that physician-prescribed sparing goals are often adapted from clinical trial studies for general populations (e.g., the Radiation Therapy Oncology Group's (RTOG) sparing goals, the QUANTEC (Quantitative Analysis of Normal Tissue Effects in the Clinic) toxicity data, etc.) that ignore specific anatomical, geometric, and demographic information for individual patients, and often represent the upper limit of an organ's dose tolerance rather than an individual patient's lowest achievable dose in that organ. In summary, because of the lack of quantitative tools for linking variations in anatomy to variations in OAR sparing doses, planners must rely on personal experience and expertise when making adjustments for individual patients. Further, because of the lack of quantitative tools for providing trade-off options between various PTV coverage objectives and OAR sparing objective, physicians and planners must rely on personal experience and expertise when making treatment decisions for individual patients. It is noted that trade-off options may be discrete or continuous, meaning there may be two or more trade-off options made available to a user.

For at least the aforementioned reasons, it is desired to provide improved systems and techniques for radiation therapy decision making and radiation therapy treatment planning.

BRIEF SUMMARY

Disclosed herein are systems and methods for specifying treatment criteria and treatment planning parameters for patient specific radiation therapy planning. According to an aspect, a method includes receiving data about a patient, computing geometric characterization of one or more organs at risk proximate to a target volume of a patient or vice versa, and selecting relevant treatment knowledge and experience. The method also includes generating, based on the received data, computed geometric characterization, and available knowledge and experience, a first set of radiation treatment planning parameters that will lead to a high quality or best achievable plan for the patient. Further, the method includes model-based prediction, based on the data, a second set or more of radiation treatment planning parameters that will lead to alternative best achievable plans with different organ sparing objectives for treating the patient. The first set of radiation treatment planning parameters is different than the second or more sets of radiation treatment planning parameters. The two or multiple sets for parameters can be used separately or in conjunction to generate treatment plans that address different emphasis of clinical goals. The method also includes presenting the first and more radiation treatment planning parameters via a user interface. The method may be implemented by a suitable computing device having a computer program for implementing the functionality described herein.

The systems and methods make use of and extract information from all source types of radiation treatment knowledge, including but not limited to patient treatment plans generated by human expert planners, Pareto-optimal IMRT plans generated by the multi-objective optimizations or similar systems, published radiation treatment guidelines, personal treatment planning knowledge, etc.

BRIEF DESCRIPTION OF THE SEVERAL VIEWS OF THE DRAWINGS

The foregoing aspects and other features of the present subject matter are explained in the following description, taken in connection with the accompanying drawings, wherein.

DETAILED DESCRIPTION

Figure 1A:
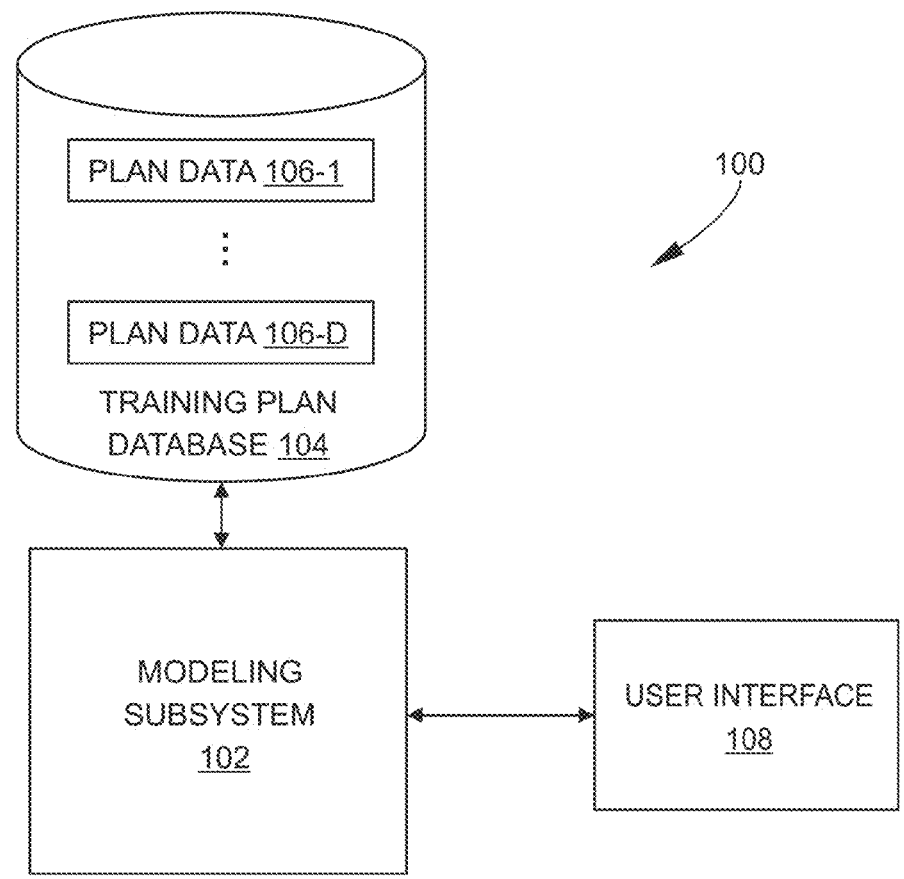
FIG. 1A is a block diagram of an example planning parameter-generation system for radiation therapy planning in accordance with embodiments of the present disclosure.

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

The presently disclosed subject matter provides decision support tools for specifying treatment criteria and treatment parameters for patient-specific radiation therapy planning and selection of radiation treatment options. For example, the presently disclosed subject matter includes systems and methods that provide decision support for specifying treatment criteria and treatment parameters for patient-specific radiation therapy planning and trade-off choices among different treatment goals and objectives. According to embodiments, a method for modeling the trade-off between PTV coverage and OAR sparing is provided. According to another aspect, an ontological framework is used to model treatment guidelines of published journals and other materials.

According to another aspect, a method integrates computerized knowledge from all models in an intuitive and interactive ontology framework. An example system can collect evidence, experience, and knowledge of treatment planning in a distributed and collaborative platform that converts the evidence, experience, and knowledge into computerized models with a process for continuous updates, self-refinement/evolvement, and verification.

According to another aspect, a system is provided for providing decision support using models described herein for delivering new evidences to the modeling system for incremental learning and enhancement of the computerized models.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

As referred to herein, the term "computing device" should be broadly construed. It can include any type of device including hardware, software, firmware, the like, and combinations thereof. A computing device may include one or more processors and memory or other suitable non-transitory, computer readable storage medium having computer readable program code for implementing methods in accordance with embodiments of the present disclosure. A computing device may be, for example, retail equipment such as POS equipment. In another example, a computing device may be a server or other computer located within a retail environment and communicatively connected to other computing devices (e.g., POS equipment or computers) for managing accounting, purchase transactions, and other processes within the retail environment. In another example, a computing device may be a mobile computing device such as, for example, but not limited to, a smart phone, a cell phone, a pager, a personal digital assistant (PDA), a mobile computer with a smart phone client, or the like. In another example, a computing device may be any type of wearable computer, such as a computer with a head-mounted display (HMD). A computing device can also include any type of conventional computer, for example, a laptop computer or a tablet computer. A typical mobile computing device is a wireless data access-enabled device (e.g., an iPHONE® smart phone, a BLACKBERRY® smart phone, a NEXUS ONE™ smart phone, an iPAD® device, or the like) that is capable of sending and receiving data in a wireless manner using protocols like the Internet Protocol, or IP, and the wireless application protocol, or WAP. This allows users to access information via wireless devices, such as smart phones, mobile phones, pagers, two-way radios, communicators, and the like. Wireless data access is supported by many wireless networks, including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or microbrowsers, which are web browsers with small file sizes that can accommodate the reduced memory constraints of wireless networks. In a representative embodiment, the mobile device is a cellular telephone or smart phone that operates over GPRS (General Packet Radio Services), which is a data technology for GSM networks. In addition to a conventional voice communication, a given mobile device can communicate with another such device via many different types of message transfer techniques, including SMS (short message service), enhanced SMS (EMS), multi-media message (MMS), email WAP, paging, or other known or later-developed wireless data formats. Although many of the examples provided herein are implemented on smart phone, the examples may similarly be implemented on any suitable computing device, such as a computer. The system may be implemented in a cloud computing environment.

As referred to herein, the term "user interface" is generally a system by which users interact with a computing device. A user interface can include an input for allowing users to manipulate a computing device, and can include an output for allowing the computing device to present information and/or data, indicate the effects of the user's manipulation, etc. An example of a user interface on a computing device includes a graphical user interface (GUI) that allows users to interact with programs or applications in more ways than typing. A GUI typically can offer display objects, and visual indicators, as opposed to text-based interfaces, typed command labels or text navigation to represent information and actions available to a user. For example, a user interface can be a display window or display object, which is selectable by a user of a computing device for interaction. The display object can be displayed on a display screen of a computing device and can be selected by and interacted with by a user using the user interface. In an example, the display of the computing device can be a touch screen, which can display the display icon. The user can depress the area of the display screen where the display icon is displayed for selecting the display icon. In another example, the user can use any other suitable user interface of a computing device, such as a keypad, to select the display icon or display object. For example, the user can use a track ball or arrow keys for moving a cursor to highlight and select the display object.

One major source of knowledge is the dose volume effects knowledge that physicians rely on to perform the critical task of prescribing proper radiation dose for individual patients. This knowledge may be attained from numerous clinical trials and studies published in paper articles and guidelines, and from physicians' personal experience. There is very little support for physician's highly complex decision-making process for dose prescription. A decision support system is disclosed herein to integrate the patient-specific predictive models with a computerized model of clinical trials literature in a formal ontological network.

The present disclosed subject matter can provide radiation oncologists with practical and clinically accepted patient-specific optimal planning parameters predicted from models that formalize past experience and knowledge. Examples of this are provided in U.S. Patent Publication No. 2012/0014507 entitled "Automatic Generation of Patient-Specific Radiation Therapy Planning Parameters," the contents of which are hereby incorporated by reference in its entirety. Another aspect of the present disclosure provides for dose prediction models that are established by learning from databases of patient treatment plans generated by human expert planners, Pareto-optimal plans generated by the multi-objective optimizations or similar systems, and by learning from published radiation treatment guidelines, personal treatment planning knowledge, etc. A plan is Pareto optimal if it is impossible to further improve a certain dosimetric parameter without compromising the other parameters. Pareto optimal plans can include a set of plans that satisfy different planning criteria and objectives. The knowledge embedded in such plans/sources that are extracted into dose prediction models include, but are not limited to, (1) patient-specific anatomy features and its correlation to dose/DVHs in the OAR, based on his/her own unique tumor target and organ shape/positions relative to the tumor volume, and (2) clinical knowledge from the radiation oncologist's experience and expertise and planner's experience and expertise about beam configuration (e.g., energy, collimator size and orientations, special blocks, etc.), dose constraint settings (dose volume relations and weighing factors, etc.), and the like.

Another aspect of the present disclosure provides for a method for modeling the trade-off between PTV coverage and OAR sparing comprising, or different OAR sparing compromising, consisting of, or consisting essentially of learning from various knowledge sources described hereinabove. The dose prediction model accounts for many things, including but not limited to, variation of multiple OARs, their relationships to PTV, the limitations/constraints of beam arrangements, the specific patient conditions that calls for specific trade-off organ dose sparing, etc. The anatomical features about the patient used in the dose prediction model include, but are not limited to, one or more of the following measures: OAR volumes; PTV volumes; fraction of OAR volumes overlapping with PTV (overlap volumes); fraction of OAR volumes outside the treatment fields (out-of-field volumes); fraction of OAR volumes that relate critical toxicity data points; distance to target histogram (DTH) in Euclidean system or other non-Euclidean metrics; distance of target to OAR histogram (DOH) in Euclidean system or other non-Euclidean metrics; tightness of the geometric enclosure of PTV surrounding OAR; and other shape descriptions, combinations thereof, and the like.

The dose features that the model may correlate to anatomy features include, but are not limited to, one or more of the following measures: PTV dose homogeneity; dose gradient around OAR and PTV; partial dose gradient around one OAR; dose volume points (e.g., mean dose, median dose, max dose, dose corresponding to 30% volume, etc.) and dose volume histograms (DVH) or PTV and OAR; 3D isodose lines' positions and volumes; 3D isodose at specific anatomical points, combinations thereof, and the like.

In some embodiments, the dose and DVH prediction models establishes the correlations using anatomical features as input and the dose features as output. Part or all of these features can be used at a time.

In addition, these features can be further processed to reduce data dimension. For example, DVHs, DTHs, DOHs, and the like can be sent to dimension reduction techniques, such as principle component analysis, or multi-dimensional scaling, etc., to reduce the data dimension. Such techniques are known to those skilled in the art.

The dose prediction model described herein establishes the anatomy to dose correlation using machine learning techniques, statistical analysis, and the like. For example, a support vector regression model that maps a number of anatomical features extracted from PTVs and OARs to a number of dose volume features can be used to predict the dose volume histogram (DVH) of the OARs and PTVs in a number of test patient configurations. Another example comprises using stepwise multiple regression method systematically to analyze the correlation between these patient anatomical features and the corresponding dose volume features. The stepwise regression method adds in most significant anatomical factor to the model and eliminates the least significant one at each step of regression so that the only significant factors are included in the final model.

Another aspect of the present disclosure provides a method of integrating computerized knowledge from all models described herein and presenting the decision alternatives in an intuitive and interactive user interface. The critical organ sparing parameters can draw information from one of these sources, or from in combination. Further, the information will be integrated and a trade-off dose prediction model can be used to allow planners to choose different options to assign/prescribe dose to different organs taking into account the specific needs of each unique patient. The trade-off model may provide multiple trade-off options.

The patient unique information includes all information that may potentially influence the physician's decision on prescribing dose to the PTV and each of the OARs. Factors may include, but are not limited to, the patient's previous radiation treatment, the prior treatment dose, location, and the dose volume information of the prior treatment to each of the OARs, patient's physiological conditions such as organ function analysis, transplant conditions, combinations thereof and the like.

FIG. 1A illustrates a block diagram of an example planning parameter-generation system 100 for radiation therapy planning in accordance with embodiments of the present disclosure. It is noted that the planning parameter-generation system 100 is described as being implemented by a single computing device in this example, although it should be appreciated that the system 100 may alternatively be implemented by one or more computing devices located locally together or remote from one another. The system 100 may be implemented by one or more processors and memory. For example, the system 100 may be suitably implemented hardware, software, firmware, or combinations thereof.

Referring to FIG. 1A, the planning parameter-modeling and prediction system 100 may include a modeling subsystem 102 and a training plan database 104 interconnected as shown. The modeling subsystem 102 is configured to read from and write to the training plan database 104, and other knowledge information such as guidelines, personal experiences, etc. The modeling subsystem 102 may generate a planning parameter for a new patient as described in more detail herein. Further, the modeling subsystem 102 is configured to store a representation of a predictive model, to train the predictive model, to generate a computer-executable program that applies the trained predictive model, and to execute tasks and functions described herein. Additional details of the modeling subsystem 102 is described herein.

The training plan database 104 is configured to provide persistent storage of data and efficient retrieval of the stored data. In an example, the database 104 may include records 106-1 through 106-D, where each record contains data associated with a training treatment plan that was formulated by an expert human planner for the patient using either a trial-and-error approach or a Pareto-front guided search process. Example contents of the training plan database 104 are described in further detail herein.

Figure 1B:
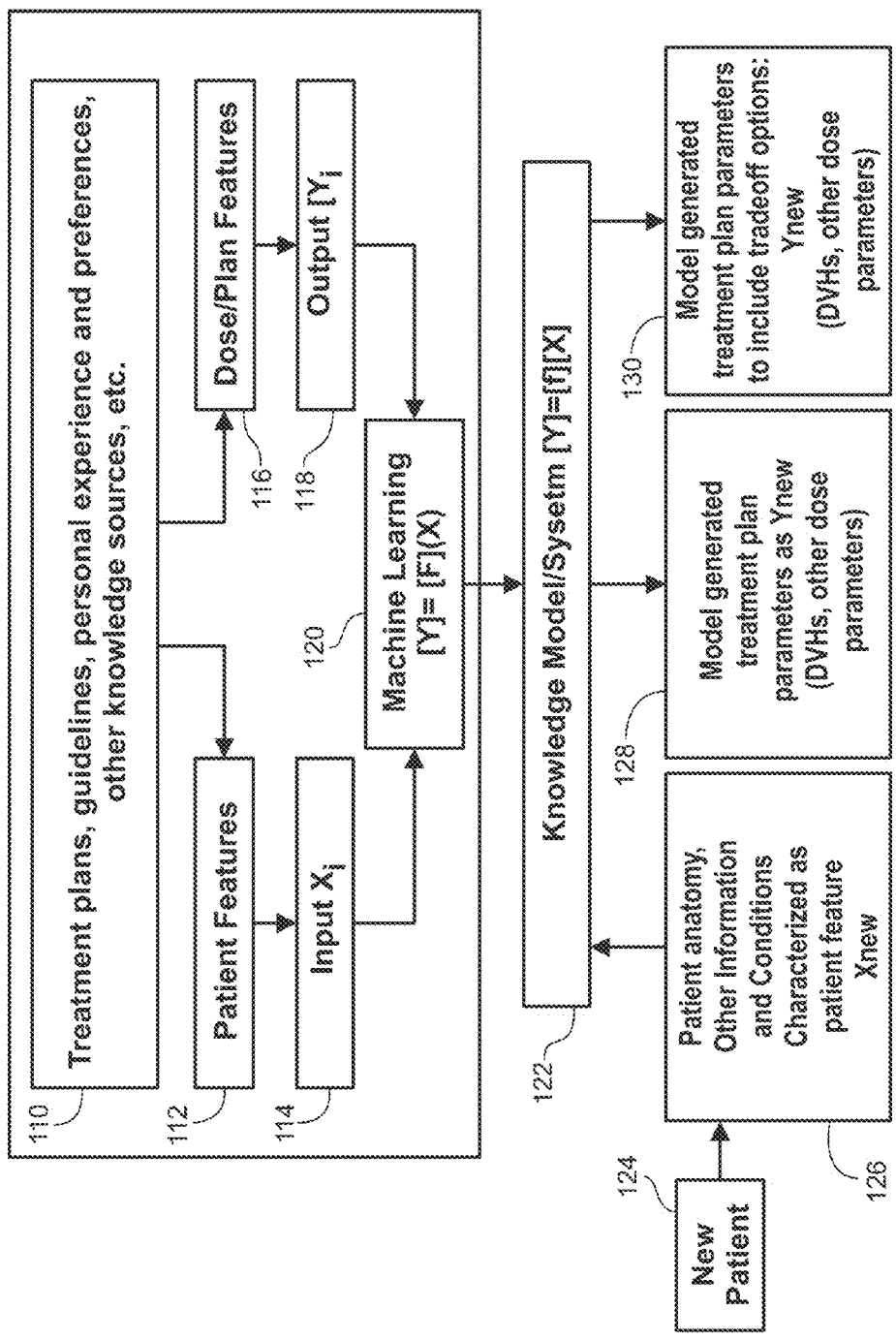
FIG. 1B is a block diagram of another example planning parameter-generation system for radiation therapy planning in accordance with embodiments of the present disclosure.

FIG. 1B illustrates a block diagram of an example planning parameter-generation system for radiation therapy planning in accordance with embodiments of the present disclosure. It is noted that the planning parameter-generation system is described as being implemented by a single computing device in this example, although it should be appreciated that the system may alternatively be implemented by one or more computing devices located locally together or remote from one another. The system may be implemented by one or more processors and memory. For example, the system may be suitably implemented hardware, software, firmware, or combinations thereof.

Referring to FIG. 1B, the system includes providing 110 treatment plans, guidelines, personal experience and preferences, other knowledge sources, etc. This information may be provided to a database. Patient features 112 and dose/plan features 116 may be placed into input Xi 114 and output Yi 118, respectively, which may be placed into machine learning block 120. These components may be involved in the training of the model. Subsequent components relate to application of the model in a knowledge model/system 122.

Subsequently, new patient information 124 may be input. This information (e.g., patient anatomy, other information and conditions) may be characterized as patient feature Xnew. The system 122 may use this new patient information to generate and output model generated treatment plan parameters 128 as Ynew (DVHs, other dose parameters). Further, the system 122 may use this new patient information to generate and output model generated treatment plan parameters to include trade-off options: Ynew (DVHs, other dose parameters).

Figure 2:
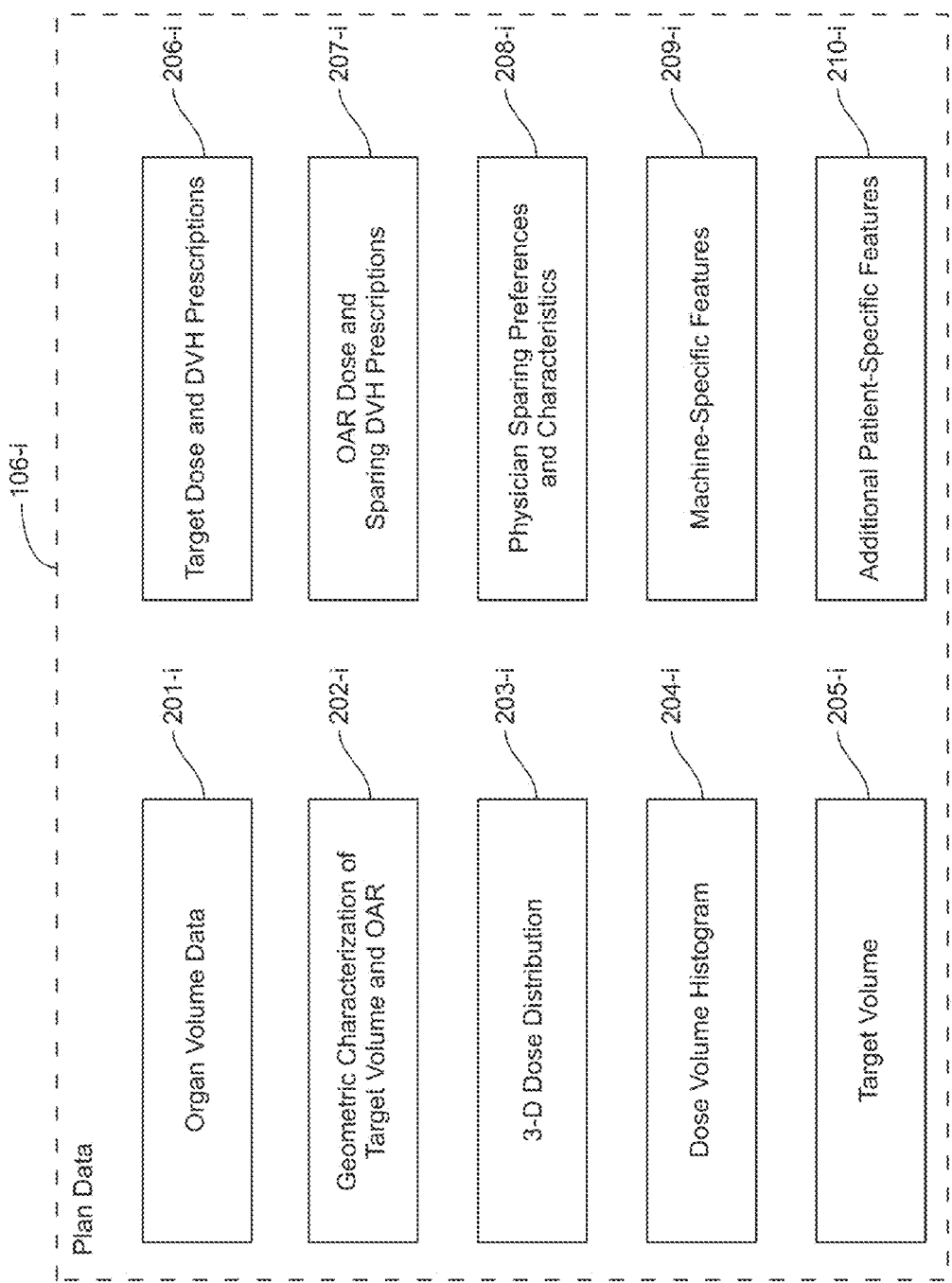
FIG. 2 is a block diagram of example contents of example patient data and patient treatment plan data.

FIG. 2 illustrates a block diagram of example contents of an example record 106-i, where i is an integer between 1 and D inclusive, in accordance with embodiments of the present disclosure. As shown in FIG. 2, record 106-i may include, but is not limited to: organ volume data 201-i; geometric characterization 202-i; three-dimensional dose distribution 203-i; dose volume histogram 203-i; target volume 205-i; target dose and DVH prescriptions 206-i; OAR dose and DVH sparing prescriptions 207-i; physician sparing preferences and characteristics 208-i (e.g., limit lung volume receiving at least 10 Gy to less than 5%, meet all sparing goals for single-kidney patient, etc.); machine-specific features 209-i (e.g., treatment modality, beam angle arrangement, etc.); and additional patient-specific features 210-i (e.g., clinical variables, demographic variables, etc.).

Figure 3:
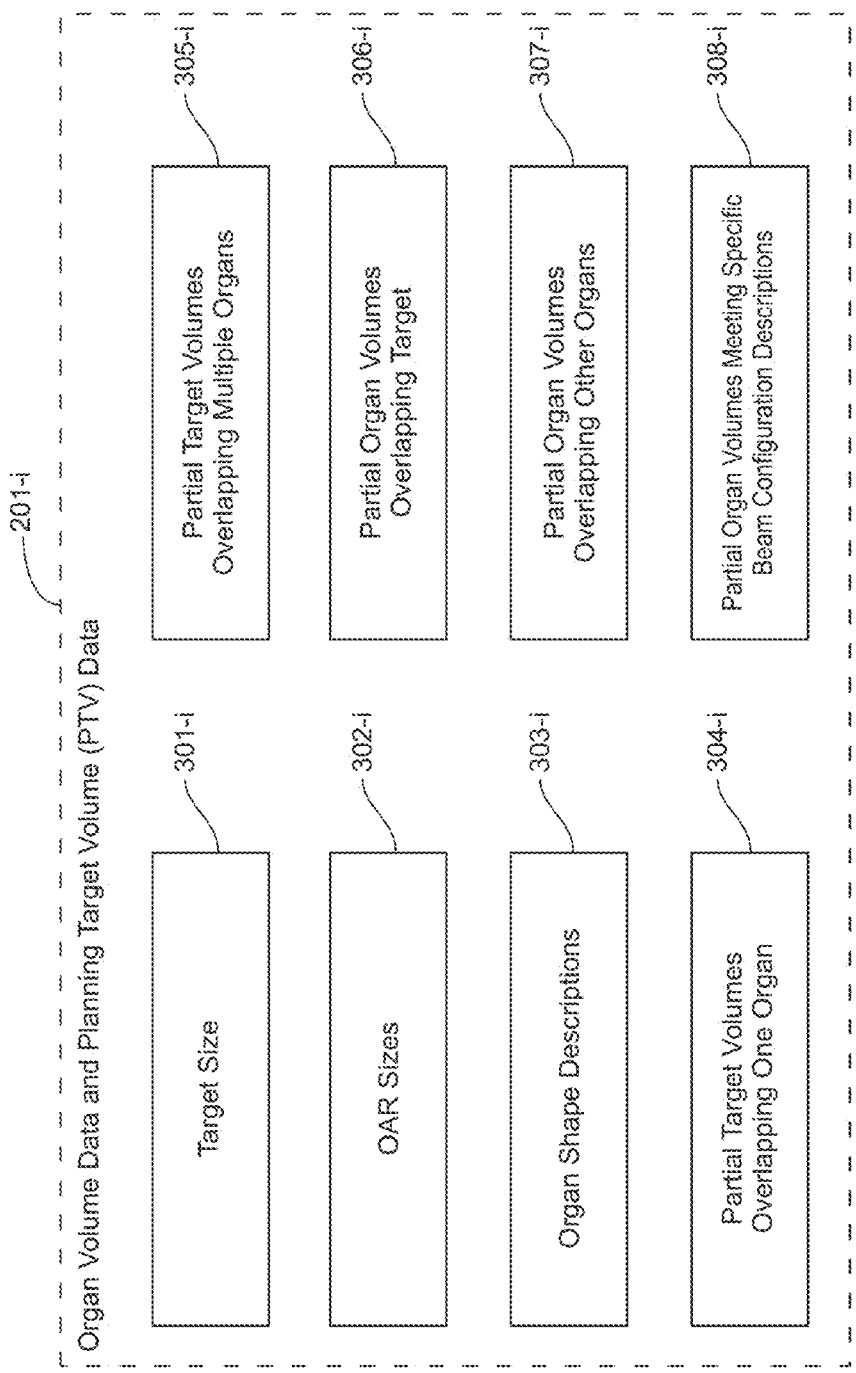
FIG. 3 is a block diagram of example contents of organ volume data and planning target volume (PTV) data.

FIG. 3 illustrates a block diagram of example contents of organ volume data 201-i, where i is an integer between 1 and D inclusive, in accordance with the illustrative embodiment of the present disclosure. Referring to FIG. 3, organ volume data 201-i may store, but is not limited to: target volume size 301-i, which is the size (i.e., volume) of the target volume, in appropriate units (e.g., cubic millimeters, etc.); organ at risk (OAR) volume sizes 302-i; organ shape descriptions 303-i; partial target volumes 304-i overlapping one organ; partial target volumes 305-i overlapping multiple organs; partial organ volumes 306-i overlapping target; partial organ volumes 307-i overlapping other organs; and partial organ volumes 308-i meeting specific beam configuration descriptions (e.g., partial volumes residing outside primary radiation fields, etc.). In other examples, the data may include target shape descriptions, target-OAR shape, geometry interaction descriptions, and the like.

Figure 4:
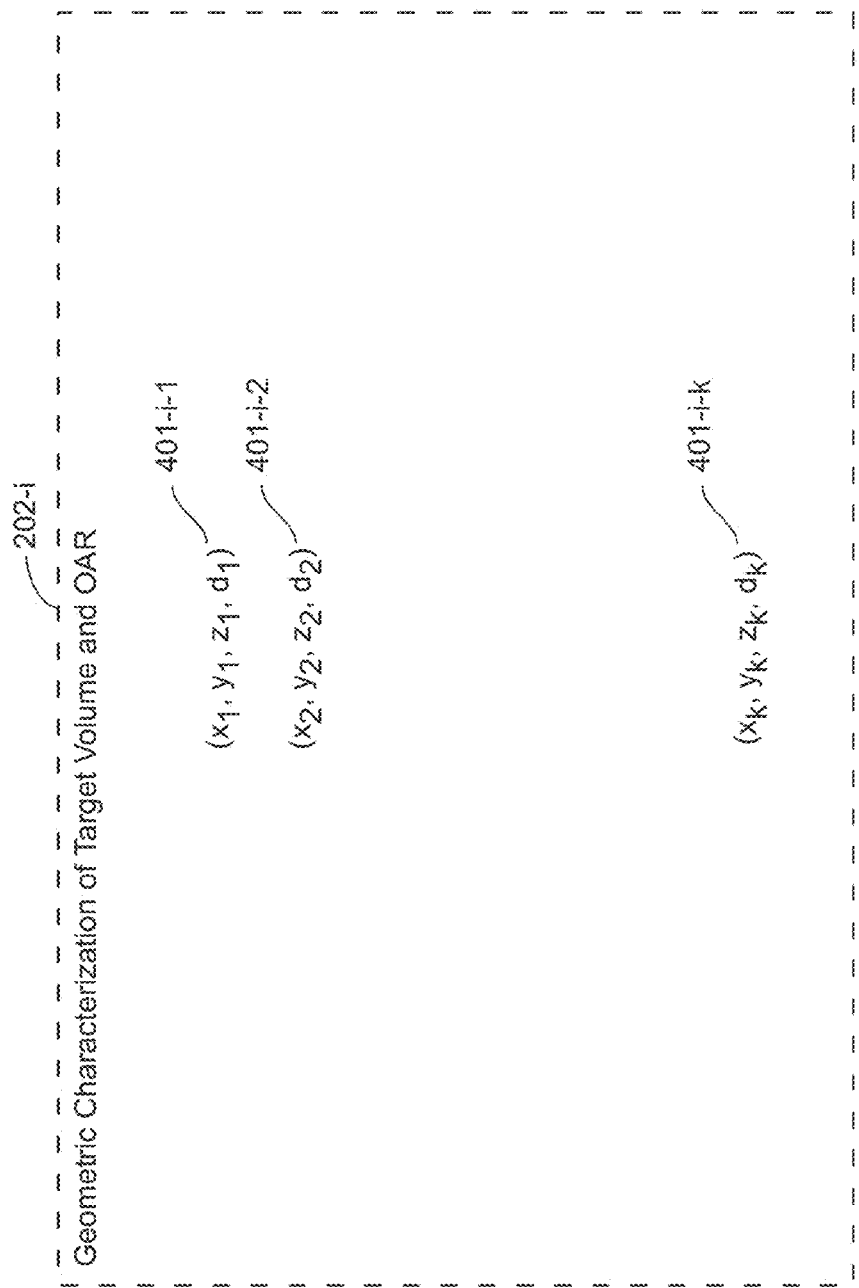
FIG. 4 is a block diagram of example contents of geometric characterization.

FIG. 4 illustrates a block diagram of example contents of geometric characterization 202-i, where i is an integer between 1 and D inclusive, in accordance with the illustrative embodiment of the present disclosure. Referring to FIG. 4, geometric characterization 202-i comprises two-dimensional points 401-i-1 through 401-i-K, where K is a positive integer, and where each of the points associates distance from the target volume with a percentage of the total volume of the organ(s) at risk. In other words, each of points 401-i-1 through 401-i-K correspond to a point on the type of curve illustrated in FIG. 6. Elements x, y, and z represent coordinates. Element d represents dose.

As will be appreciated by those skilled in the art, geometric characterization 202-i of the illustrative embodiment covers the tools and methods that can characterize the geometry of one organ at risk in relation to one or more target volumes, and to other organs at risk. One such geometry description tool is the distance to target histogram (DTH), which measures the portion of OAR or target volume that is at a certain distance from the target volume or other organs. The distance in DTH may be measured in Euclidean space or in some other non-Euclidean space, in a linear or non-linear manner (e.g., a distance space distorted by the radiation beam geometry or dose deposition characteristics, etc.).

Figure 5:
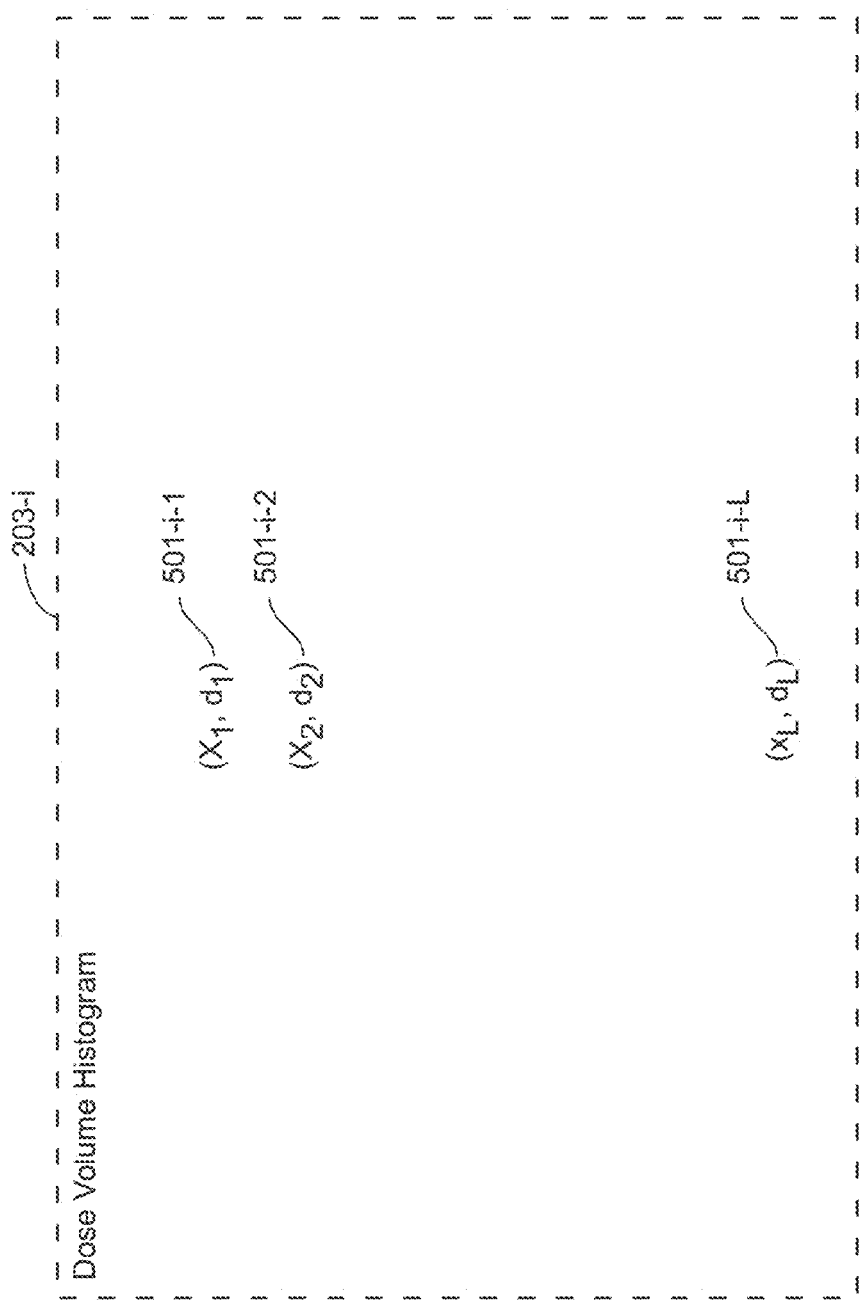
FIG. 5 is a block diagram of example contents of dose volume histogram.

FIG. 5 illustrates a block diagram of example contents of dose volume histogram 203-i, where i is an integer between 1 and D inclusive, in accordance with the illustrative embodiment of the present disclosure. As shown in FIG. 5, dose volume histogram 203-i comprises two-dimensional points 501-i-1 through 501-i-L, where L is a positive integer, and where each of the points is taken from the dose volume histogram for the patient. As described above, in some embodiments of the present disclosure, each of points 501-i-1 through 501-i-L may associate dosage ranges with a percentage of the volume being exposed to that dosage range (e.g., points corresponding to the histogram bins of the illustrative DVH in FIG. 6, etc.), while in some other embodiments, each of points 501-i-1 through 501-i-L may associate dose value with a percentage of the volume being exposed to that dose or higher (e.g., points corresponding to those of the illustrative DVH shown in FIG. 7, etc.), while in still some other embodiments, each of points 501-i-1 through 501-i-L may be obtained from some other type of representation of the dose volume histogram for the patient. Element x represents x % or x cc of target/organ/normal tissue volume. Element d represents dose.

Figure 6:
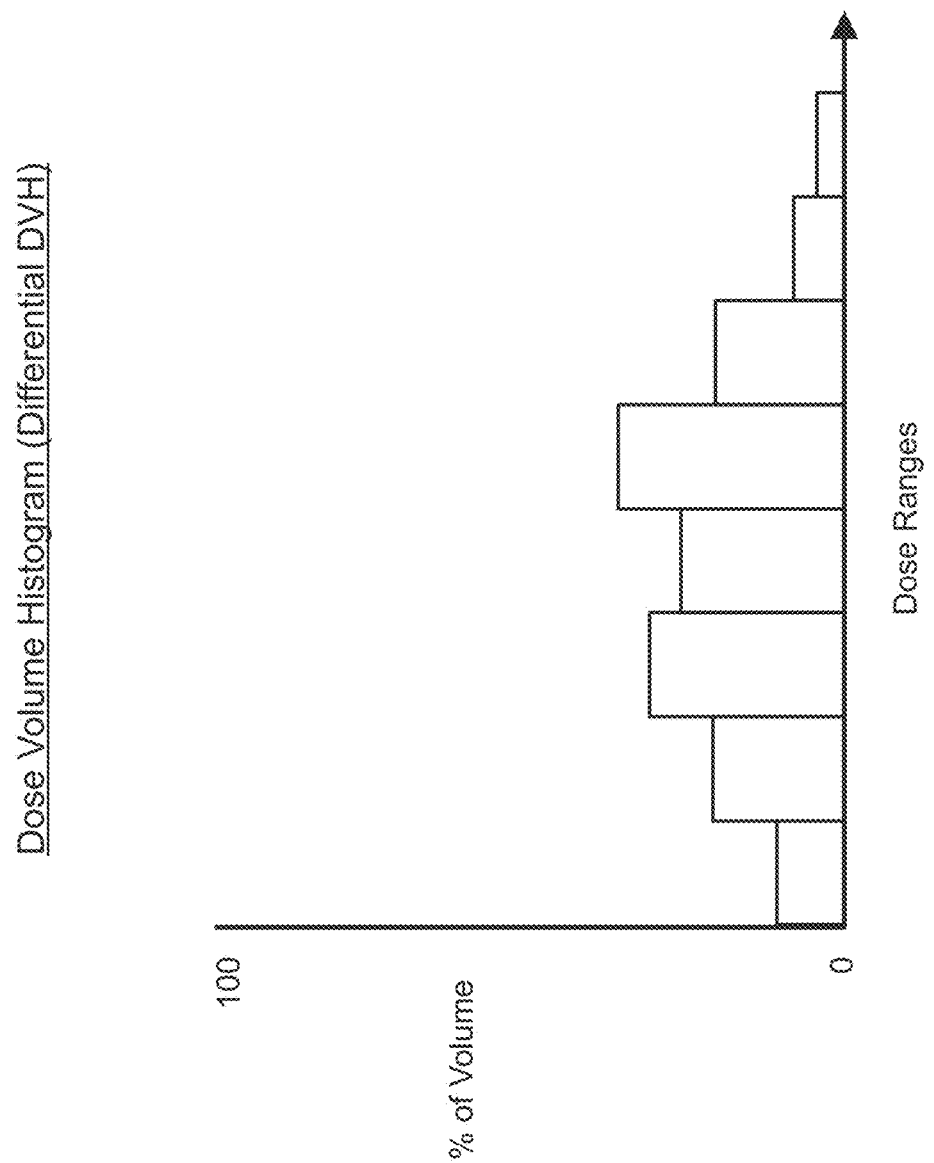
FIG. 6 is a first illustrative dose volume histogram (DVH) in accordance with an illustrative embodiment of the present disclosure.

FIG. 6 illustrates a first illustrative dose volume histogram (DVH), referred to as a "differential DVH," in accordance with the illustrative embodiment of the present disclosure. As shown in FIG. 6, DVH associates each of a plurality of dosage ranges (e.g., 0-2 Gy, 2-4 Gy, etc.) inside the volume of an organ at risk (x-axis) with the percentage of the volume being exposed to that dosage range (y-axis). X-axis indicates the x % or x cc of target/organ/normal tissue volume, and d represents dose. It is noted that the figure indicates a percentage of volume, although alternatively it may represent a cc of volume. As will be appreciated by those skilled in the art, in some embodiments of the present disclosure the dose volume histogram can be derived from a dose distribution, while in some other embodiments the dose volume histogram may be derived from the dose volume histogram, described below and with respect to FIG. 7, while in still some other embodiments the dose volume histogram may be derived from some other data or obtained in some other manner.

Figure 7:
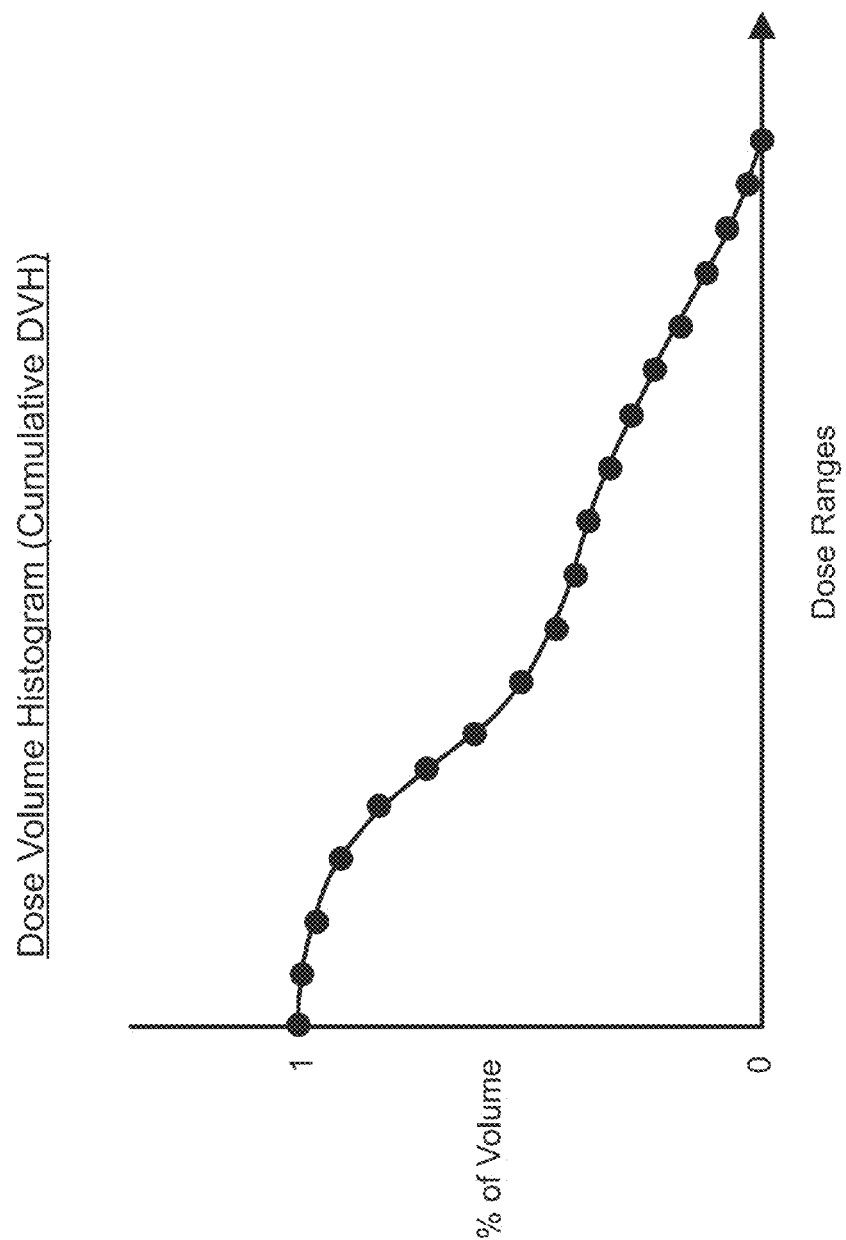
FIG. 7 depicts a second illustrative DVH, referred to as a "cumulative DVH," in accordance with the illustrative embodiment of the present disclosure.

FIG. 7 depicts a second illustrative DVH, referred to as a "cumulative DVH," in accordance with the illustrative embodiment of the present disclosure. As shown in FIG. 7, the DVH associates dosage range (x-axis) with the percentage of an organ or target volume (y-axis, where 1 corresponds to 100% volume and 0 corresponds to 0% volume). As will be appreciated by those skilled in the art, in some embodiments of the present disclosure dose volume histogram may be derived from the dose volume histogram shown in FIG. 6, while in some other embodiments dose volume histogram can be derived directly from a dose distribution, while in still some other embodiments dose volume histogram shown in FIG. 7 can be derived from some other data or obtained in some other manner. It is noted that the figure indicates a percentage of volume, although alternatively it may represent a cc of volume.

Figure 8:
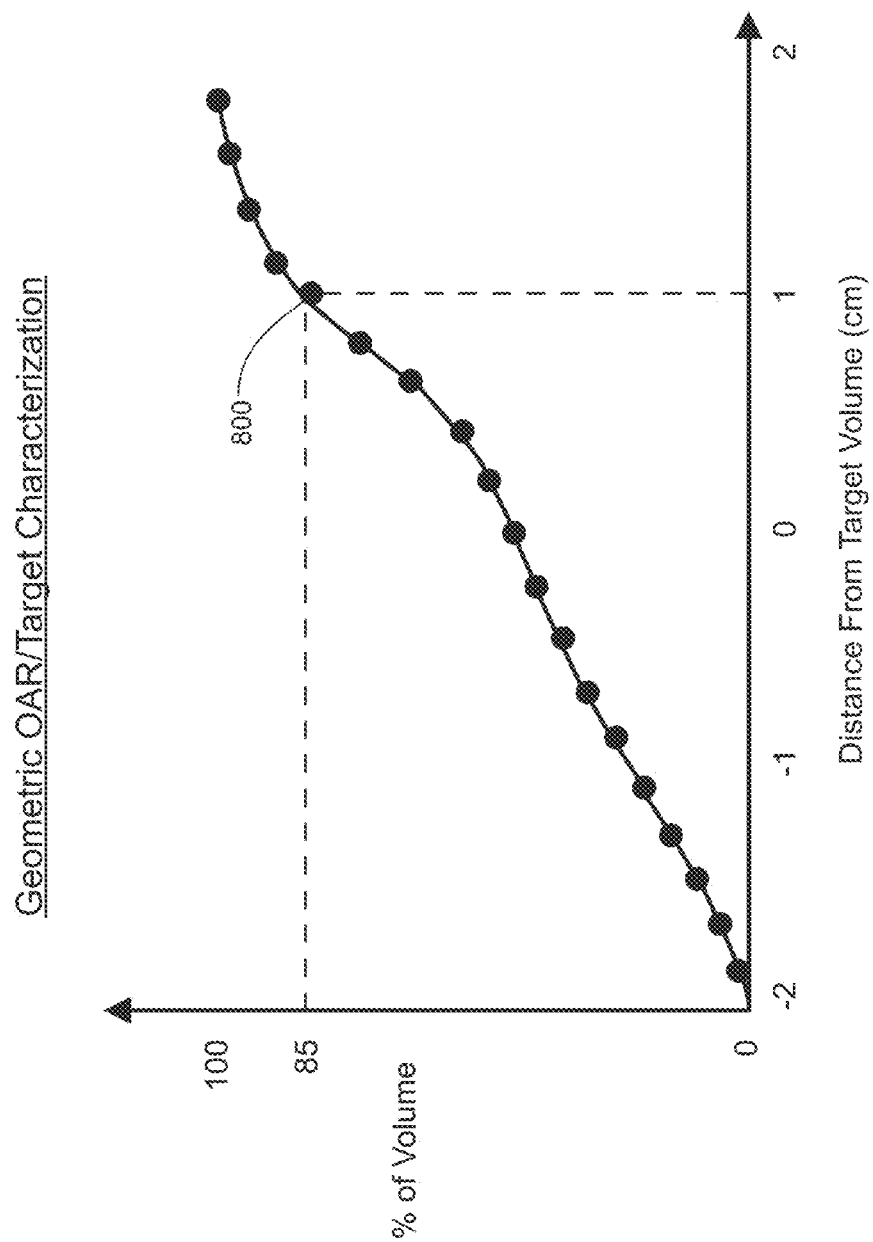
FIG. 8 depicts an illustrative graph characterizing the geometry of one or more organs at risk with respect to a target volume, in accordance with the illustrative embodiment of the present disclosure; or vice versa, one or more PTV with respect to a OAR volume (in this case, the horizontal bar is distance from OAR, and the y-bar is the % or CC of PTV volume)

FIG. 8 depicts an illustrative graph characterizing the geometry of one or more organs at risk (OAR) with respect to a target volume, in accordance with the illustrative embodiment of the present disclosure. As shown in FIG. 8, the graph associates distance from the target volume (x-axis) with a percentage of the total volume of the organ(s) at risk (y-axis), where a negative distance indicates overlap between the target and OAR. For example, point 800 indicates that 85% of the total volume of the organ(s) at risk is within one centimeter of the target volume. The distance can be further defined based on Euclidean or other non-Euclidean metric space. It is noted that FIG. 8 provides a simple example of geometric OAR/PTV characterization. In one implementation, this may include additional variations on how to calculating the distance, or other methods in describing the geometric characteristics, such as angular enclosure or the like.

Figure 9:
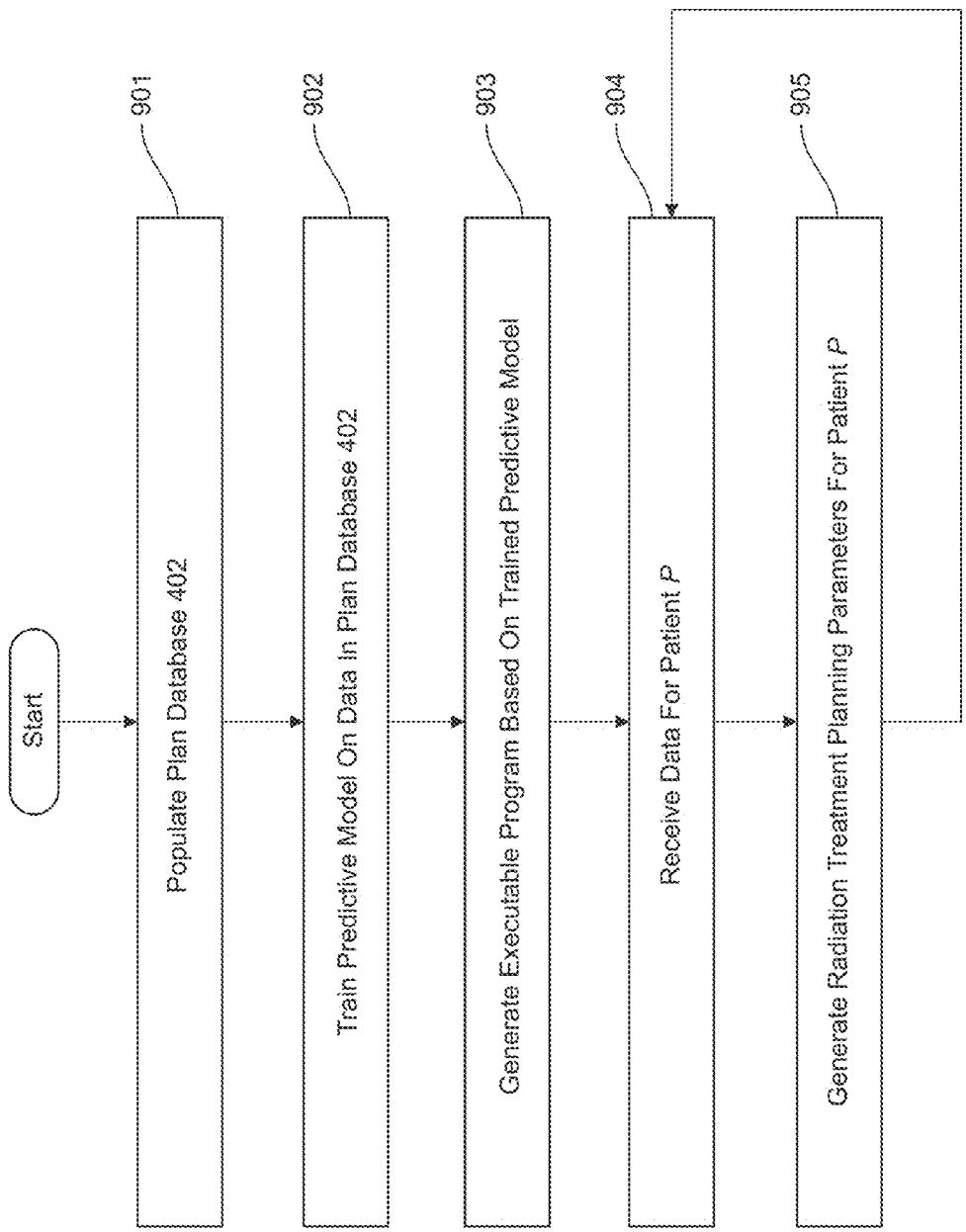
FIG. 9 is a flowchart of an example method for radiation therapy planning in accordance with embodiments of the present disclosure.

FIG. 9 illustrates a flowchart of an example method for radiation therapy planning in accordance with embodiments of the present disclosure. In this example, the method is described as being implemented by the system shown in FIG. 1B, although it should be understood that the method may alternatively be implemented by any suitable system. It should also be understood that the steps or tasks depicted in FIG. 9 can be performed simultaneously or in a different order than that depicted.

Referring to FIG. 9, the method includes populating, at task 901, a plan database. For example, the system shown in FIG. 1B or one or more other computing devices may populate a plan database. Task 901 is described in further detail herein and with respect to FIG. 10. In examples, the plan database may include, but is not limited to, personal experience and preferences or knowledge sources other than the plan database.

At task 902 of FIG. 9, a predictive model is trained on the data in the plan database. For example, the system of FIG. 1B may train a predictive model on the data in the plan database. Task 902 is described in further detail herein and with respect to FIG. 11.

At task 903 of FIG. 9, an executable program may be generated based on the trained predictive model. For example, the system of FIG. 1B may generate an executable program based on the trained predictive model.

At task 904 of FIG. 9, data may be received for a patient P for whom a radiation treatment plan is desired. For example, the system of FIG. 1B may receive data for a patient P for whom a radiation treatment plan is desired. In accordance with the illustrative embodiment, these data include, but are not limited to: the size and shape of patient P's target volume; the size(s) and shape(s) of each of patient P's organ(s) at risk; and a geometric characterization (of the form of the illustrative curve depicted in FIG. 6) of patient P's organ(s) at risk with respect to the target volume.

At task 905 of FIG. 9, a set of radiation treatment planning parameters may be generated for patient P. For example, the system of FIG. 1B may generate a set of radiation treatment planning parameters for patient P. Task 905 is described in further detail herein and with respect to FIGS. 14-16.

After task 905 has been completed, execution may continue back at task 904.

Figure 10:
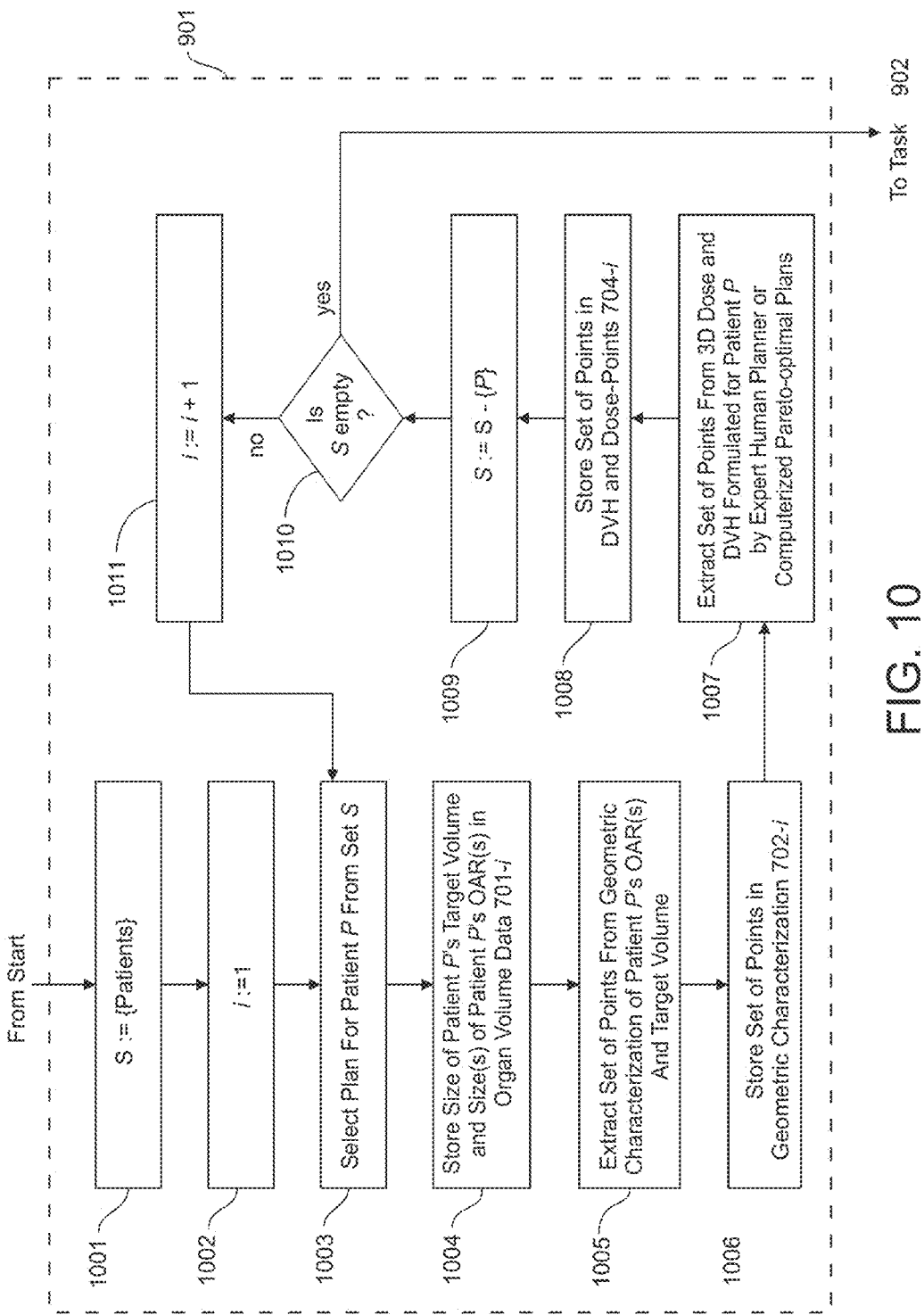
FIG. 10 depicts a flowchart of an example method for implementing task shown in FIG. 9 in accordance with embodiments of the present disclosure.

FIG. 10 depicts a flowchart of an example method for implementing task 901 shown in FIG. 9 in accordance with embodiments of the present disclosure. It should be understood by those skilled in the art, after reading this disclosure, which subtasks depicted in FIG. 10 can be performed simultaneously or in a different order than that depicted.

At subtask 1001 of FIG. 10, the modeling subsystem 104 may initialize variable S to a set of radiation treatment plans previously formulated by expert human planners using trial-and-error approach or Pareto-front guided search. At subtask 1002, the modeling subsystem 104 may initialize variable i to 1.

At subtask 1003, the modeling subsystem 104 may select from set S a plan for a patient P.

At subtask 1004, the modeling subsystem 104 may store the size of patient P's target volume and the size(s) of patient P's organ(s) at risk in organ volume data 201-*i* of patient record 106-*i* in plan database 102.

At subtask 1005, the modeling subsystem 104 may extract a set of points from a geometric characterization of patient P's organ(s) at risk and his or her target volume.

At subtask 1006, the modeling subsystem 104 may store the set of points obtained at subtask 1005 in geometric characterization 202-*i* of patient record 106-*i* in plan database 102.

At subtask 1007, the modeling subsystem 104 may extract a set of points from a dose volume histogram and dose points meeting other specific geometric characteristics that were formulated for patient P by either an expert human planner or computerized pareto-optimal plans.

It is noted that in one example subtasks 1004, 1005, 1006, and 1007 may be combined to extract a set of anatomical features and plan features 106-*i* such that all these features are extracted at once all together. Each patient anatomic feature may form a vector, and each patient's treatment plan may form a vector. All patients in the database may combined to form the anatomy feature matrix and treatment plan feature matrix.

At subtask 1008, the modeling subsystem 104 may store the set of points obtained at subtask 1007 in dose volume histogram 203-*i* of patient record 106-*i* in plan database 102.

At subtask 1009, the modeling subsystem 104 may remove patient P from set S.

At subtask 1010, the modeling subsystem 104 may check whether set S is empty; if so, execution continues at task 902 of FIG. 9, otherwise execution proceeds to subtask 1010.

At subtask 1011, the modeling subsystem 104 may increment variable i. After subtask 1010, execution continues back at subtask 1003.

Figure 11:
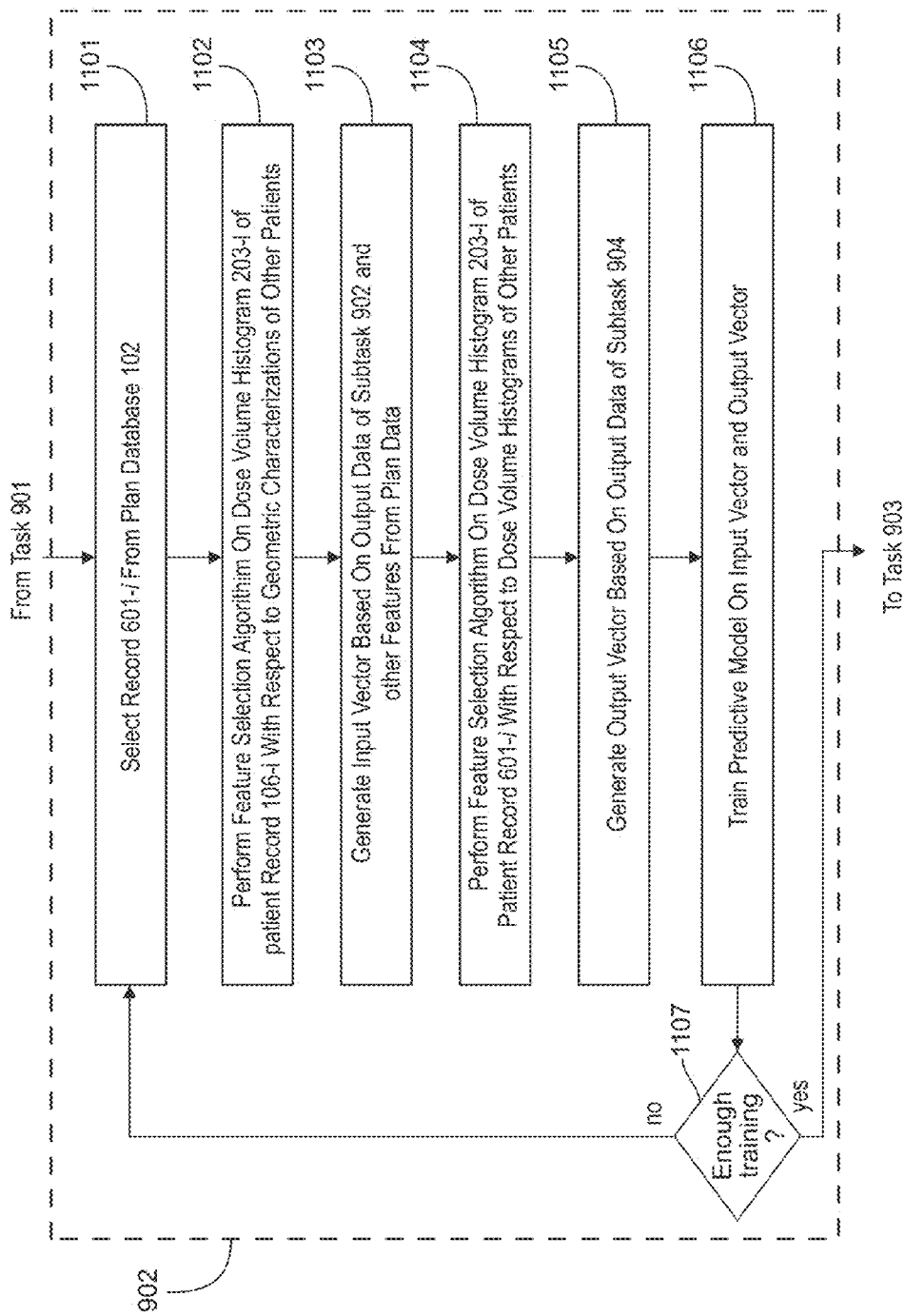
FIG. 11 depicts a detailed flowchart of task in accordance with the illustrative embodiment of the present disclosure.

FIG. 11 depicts a detailed flowchart of task 902 (model training) in accordance with the illustrative embodiment of the present disclosure. It will be clear to those skilled in the art, after reading this disclosure, which subtasks depicted in FIG. 11 can be performed simultaneously or in a different order than that depicted.

At subtask 1101, the modeling subsystem 104 may select some record 106-i from plan database 102, where i is an integer between 1 and D inclusive. As an example, this may be an input anatomy feature matrix 100x, and a plan feature matrix 100x.

At subtask 1102, the modeling subsystem 104 may perform a feature selection algorithm on geometric characterization 202-i of patient record 106-i with respect to the geometric characterizations of other patients. In accordance with the illustrative embodiment, a principal component analysis is employed as the feature selection algorithm at subtask 1102; however, as will be appreciated by those skilled in the art, in some other embodiments of the present disclosure some other type of feature selection algorithm may be employed at subtask 1102, and it will be clear to those skilled in the art, after reading this disclosure, how to make and use embodiments of the present disclosure that employ such alternative feature selection algorithms. Subtask 1102 may include performing data dimension reduction if needed.

Subtask 1102 is described in detail below and with respect to FIG. 12.

At subtask 1103, the modeling subsystem 104 may generate an input vector that comprises (i) one or more values based on the output data of the principal component analysis of subtask 1102, (ii) target size 301-i of patient record 106-i, and (iii) and organ at risk (OAR) sizes 302-i-1 through 202-i-R of patient record 106-i. As will be appreciated by those skilled in the art, in some embodiments of the present disclosure the one or more values of item (i) may simply be the principal component scores corresponding to the M eigenvalues obtained at subtask 1102, while in some other embodiments the one or more values of item (i) may be derived in some way from these M eigenvalues (e.g., via normalization of the eigenvalues, via a technique that combines the eigenvalues in some fashion, etc.). Subtask 1103 may include applying machine learning techniques such as multi-regression learning, support-vector learning, neural network learning, and the like to the anatomy feature matrix [X] and plan feature matrix [Y], to solve their relationship as [Y]=[F][X]. The matrix [F] represents the model, and it may be a complex mathematical function.

At subtask 1104, the modeling subsystem 104 may perform a feature selection algorithm on: (i) dose volume histogram 203-i of patient record 106-i, and (ii) dose points meeting other specific geometric characteristics with respect to the dose volume histograms of other patients. In accordance with the illustrative embodiment, a principal component analysis is employed as the feature selection algorithm at subtask 1104; however, as will be appreciated by those skilled in the art, in some other embodiments of the present disclosure some other type of feature reduction algorithm may be employed at subtask 1104, and it will be clear to those skilled in the art, after reading this disclosure, how to make and use embodiments of the present disclosure that employ such alternative feature selection algorithms.

Subtask 1104 is performed in a manner similar to subtask 1102, and is described in detail below and with respect to FIG. 15.

At subtask 1105, the modeling subsystem 104 may generate an output vector that is based on the output data of the principal component analysis of subtask 1104. As will be appreciated by those skilled in the art, in some embodiments of the present disclosure the output vector may simply contain principal component scores corresponding to the Q eigenvalues obtained at subtask 1104, while in some other embodiments the output vector may be derived in some way from these Q eigenvalues (e.g., via normalization of the eigenvalues, via a technique that combines the eigenvalues in some fashion, etc.).

At subtask 1106, the modeling subsystem 104 may train the predictive model on the input vector and output vector generated at subtasks 1103 and 1105, respectively. Subtask 1106 may include applying machine learning techniques such as step-wise multiple regression learning, support-vector learning, neural network learning, and the like to the anatomy feature matrix [X] and plan feature matrix [Y], to solve their relationship as [Y]=[F][X]. The matrix [F] represents the model, and it may be a complex mathematical function.

At subtask 1107, the modeling subsystem 104 may determine whether the predictive model has been trained sufficiently. As will be appreciated by those skilled in the art, in some embodiments of the present disclosure this determination can be based on one or more convergence criteria, while in some other embodiments of the present disclosure the determination may be made in some other fashion (e.g., based on some other criteria, based on a pre-determined number of iterations, etc.).

If the determination at subtask 1107 is negative, execution continues back at subtask 1101; otherwise, execution proceeds to task 903 of FIG. 9.

Figure 12:
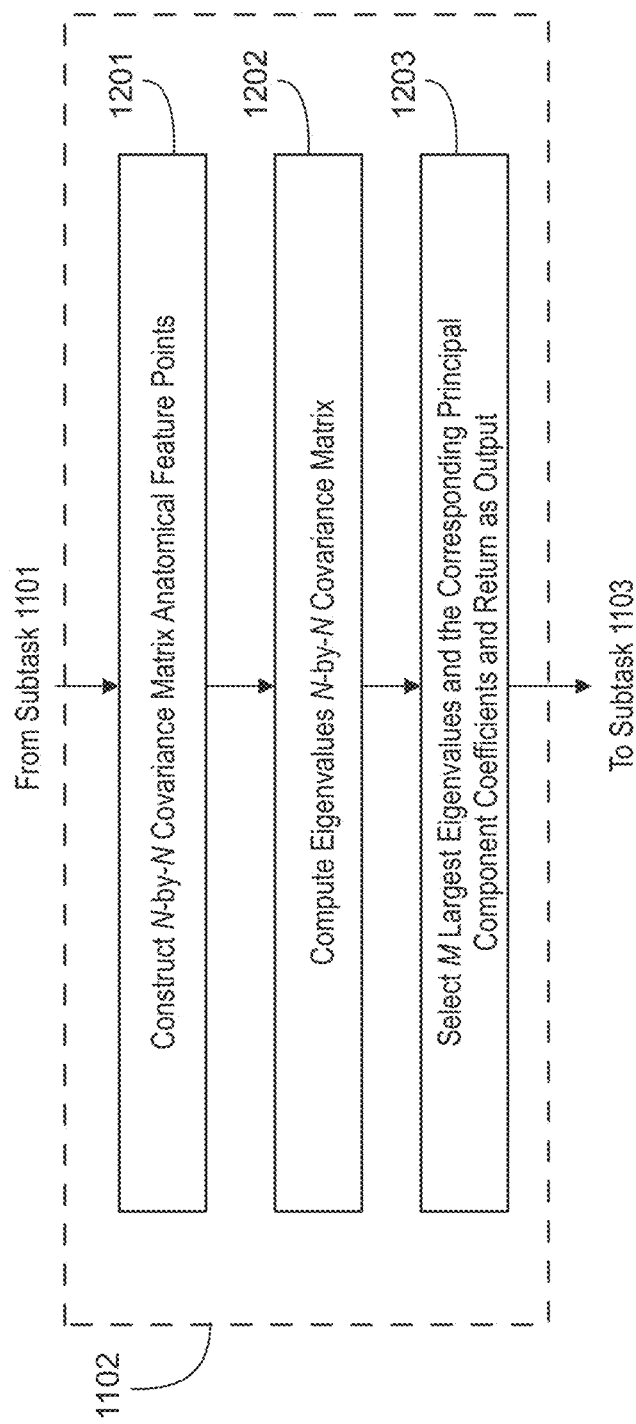
FIG. 12 depicts a detailed flowchart of subtask in accordance with the illustrative embodiment of the present disclosure.

FIG. 12 depicts a detailed flowchart of subtask 1102 in accordance with the illustrative embodiment of the present disclosure. As noted above, in accordance with the illustrative embodiment, a principal component analysis is employed as the feature selection algorithm in the subtasks of FIG. 12; however, as will be appreciated by those skilled in the art, in some other embodiments of the present disclosure some other type of feature selection algorithm may be employed, and it will be clear to those skilled in the art, after reading this disclosure, how to make and use embodiments of the present disclosure that employ such alternative feature selection algorithms. It will further be clear to those skilled in the art, after reading this disclosure, which subtasks depicted in FIG. 12 can be performed simultaneously or in a different order than that depicted. It is noted that the subtask of FIG. 12 is for data dimension reduction if needed. Example techniques include, but are not limited to, principal component analysis (PCA), multi-dimensional scaling (MDS), and the like. The example flowchart shows PCA process as an example and other dimension reduction techniques may be used.

At subtask 1201, the modeling subsystem 104 may construct an N-by-N covariance matrix of all feature points across all training plans, where N is a positive integer equal to K.

At subtask 1202, the modeling subsystem 104 may compute the eigenvalues of the N-by-N covariance matrix.

At subtask 1203, the modeling subsystem 104 may select the M largest of the eigenvalues computed at subtask 1202, where M is a positive integer between 1 and N inclusive, and returns the eigenvectors associated with selected eigenvalues and the principal component scores of the feature sets 202-$i$ as outputs to subtask 1103 of FIG. 11. After subtask 1203, execution continues at subtask 1103.

Figure 13:
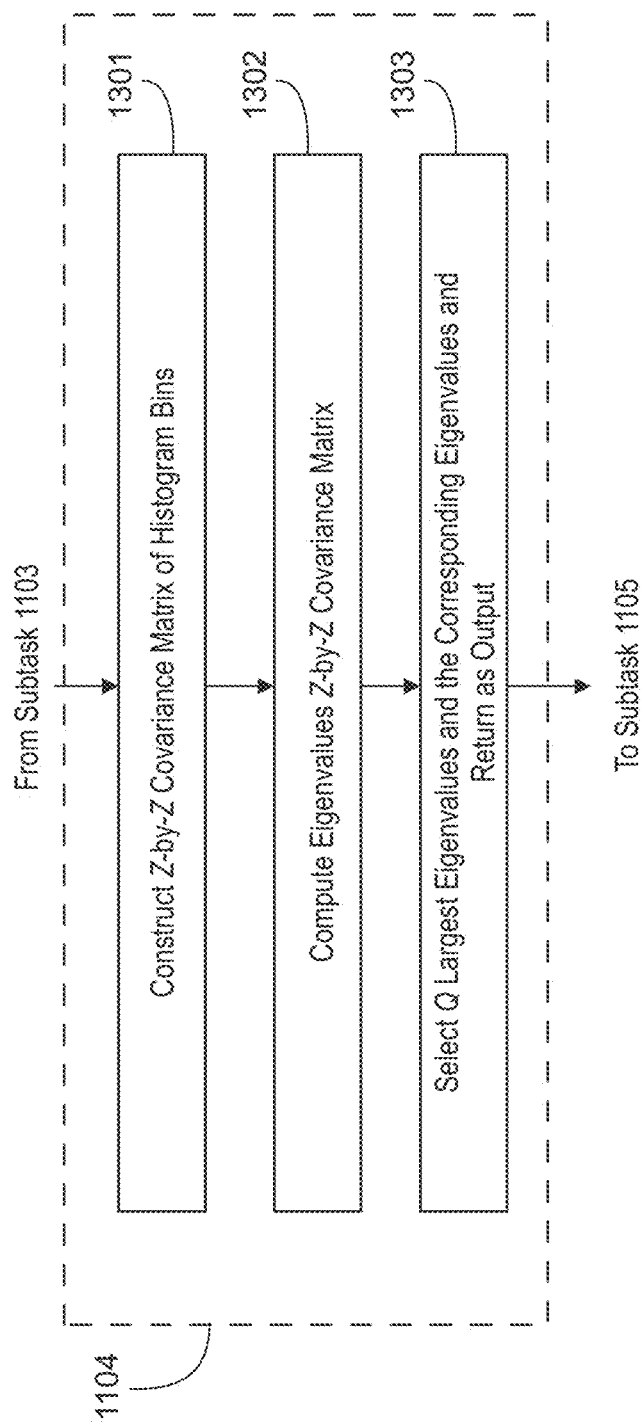
FIG. 13 depicts a detailed flowchart of subtask in accordance with the illustrative embodiment of the present disclosure.

FIG. 13 depicts a detailed flowchart of subtask 1104, in accordance with the illustrative embodiment of the present disclosure. As noted above, in accordance with the illustrative embodiment, a principal component analysis is employed as the feature reduction algorithm in the subtasks of FIG. 13; however, as will be appreciated by those skilled in the art, in some other embodiments of the present disclosure some other type of feature reduction algorithm may be employed, and it will be clear to those skilled in the art, after reading this disclosure, how to make and use embodiments of the present disclosure that employ such alternative feature reduction algorithms. It will further be clear to those skilled in the art, after reading this disclosure, which subtasks depicted in FIG. 13 can be performed simultaneously or in a different order than that depicted.

At subtask 1301, the modeling subsystem 104 may construct a Z-by-Z covariance matrix of Z sample points of dose volume histograms across all plans, where Z is a positive integer equal to L. As will be appreciated by those skilled in the art, in some embodiments of the present disclosure the value of Z may be the same as the value of N used at subtask 1201, while in some other embodiments of the present disclosure, Z may have a different value than N.

At subtask 1302, the modeling subsystem 104 may compute the eigenvalues of the Z-by Z covariance matrix, in well-known fashion.

At subtask 1303, the modeling subsystem 104 may select the Q largest of the eigenvalues computed at subtask 1302, where Q is a positive integer between 1 and Z inclusive, and returns the eigenvectors associated with selected eigenvalues and the principal component scores as outputs to subtask 1105 of FIG. 11. After subtask 1303, execution continues at subtask 1105.

Figure 14:
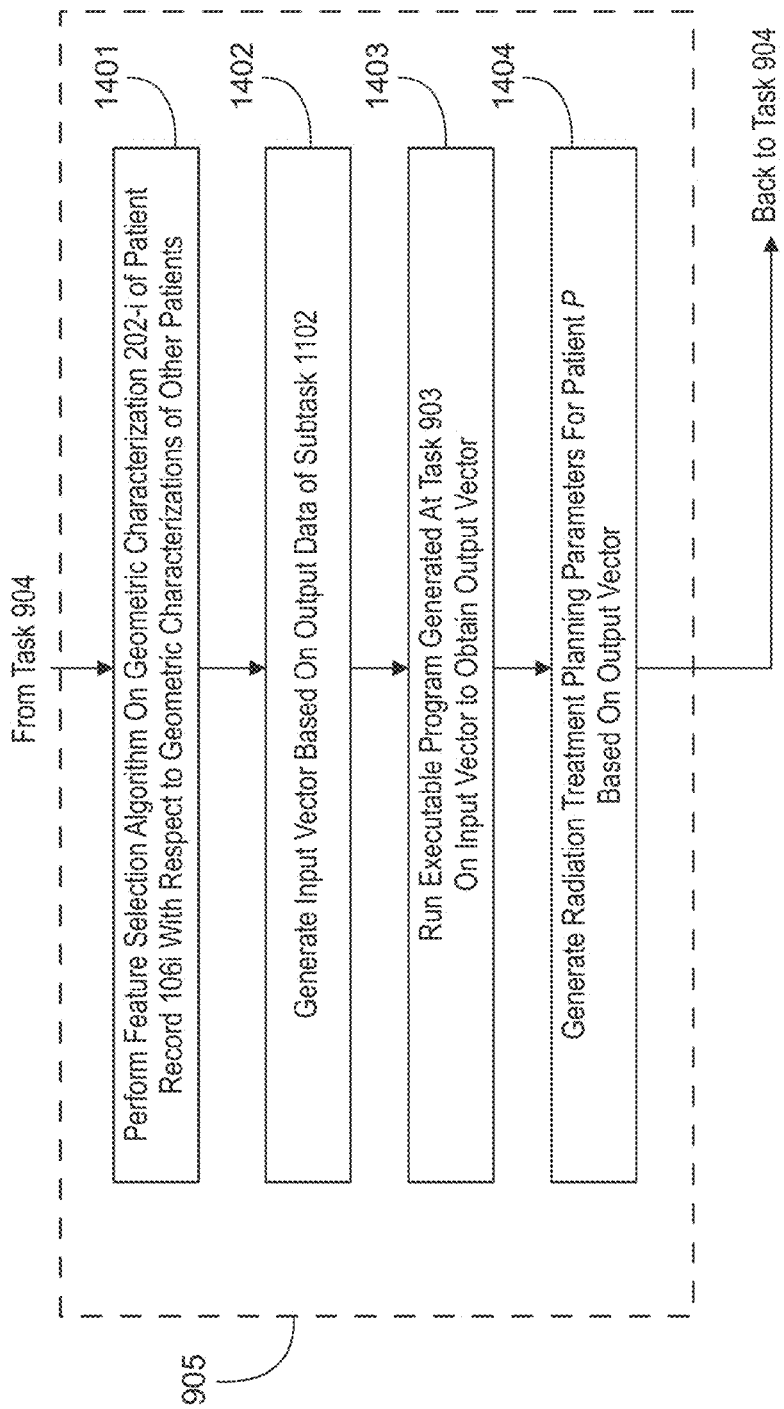
FIG. 14 depicts a detailed flowchart of task in accordance with the illustrative embodiment of the present disclosure.

FIG. 14 depicts a detailed flowchart of task 905, in accordance with the illustrative embodiment of the present disclosure. It will be clear to those skilled in the art, after reading this disclosure, which subtasks depicted in FIG. 14 can be performed simultaneously or in a different order than that depicted. This method is about how to use the trained model to predict dose/DVH parameters of a new patient.

At subtask 1401, the modeling subsystem 104 may perform a feature selection algorithm on the geometric characterization 202-$i$ for patient P (received at task 904) with respect to the geometric characterizations of other patients. A dimension reduction technique may be used. As noted above, in accordance with the illustrative embodiment, a principal component analysis is employed as the feature selection algorithm in the subtasks of FIG. 14; however, as will be appreciated by those skilled in the art, in some other embodiments of the present disclosure some other type of feature selection algorithm may be employed, and it will be clear to those skilled in the art, after reading this disclosure, how to make and use embodiments of the present disclosure that employ such alternative feature selection algorithms.

Subtask 1401 is described in detail below and with respect to FIG. 15.

At subtask 1402, the modeling subsystem 104 may generate an input vector that contains (i) one or more values based on the output data of the principal component analysis of subtask 1401, (ii) the size and shape of patient P's target volume, and (iii) the size(s) and shape(s) of patient P's organ(s) at risk. As will be appreciated by those skilled in the art, in some embodiments of the present disclosure the one or more values of item (i) may simply be the principal component scores corresponding to the M eigenvalues obtained at subtask 1401, while in some other embodiments the one or more values of item (i) may be derived in some way from these M eigenvalues (e.g., via normalization of the eigenvalues, via a technique that combines the eigenvalues in some fashion, etc.).

At subtask 1403, the modeling subsystem 104 may run the executable program generated at task 903 on the input vector and obtains an output vector.

At subtask 1404, the modeling subsystem 104 may generate radiation treatment planning parameters for patient P based on the output vector. Subtask 1404 is described in detail below and with respect to FIG. 16.

After subtask 1404, execution continues back at task 904.

Figure 15:
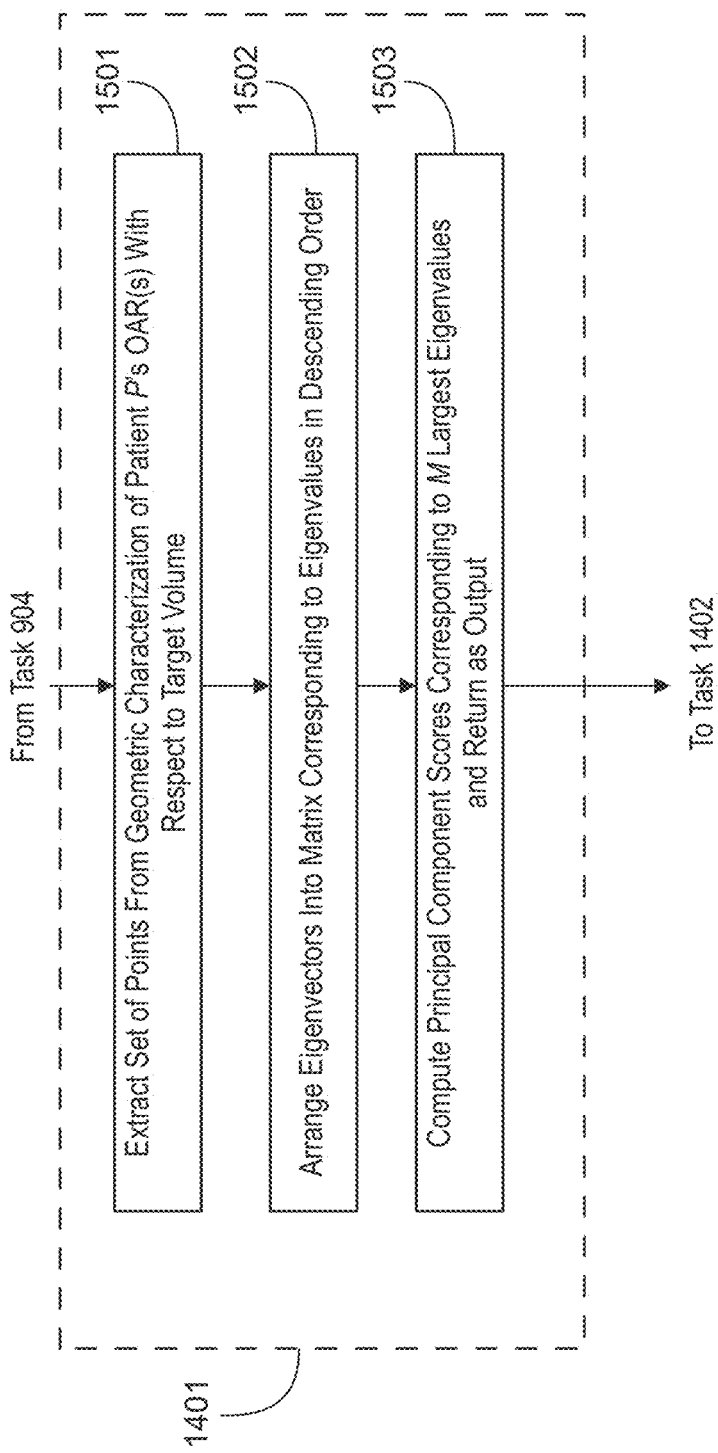
FIG. 15 depicts a detailed flowchart of subtask in accordance with the illustrative embodiment of the present disclosure.

FIG. 15 depicts a detailed flowchart of subtask 1401 in accordance with the illustrative embodiment of the present disclosure. As noted above, in accordance with the illustrative embodiment, a principal component analysis is employed as the feature selection algorithm in the subtasks of FIG. 15; however, as will be appreciated by those skilled in the art, in some other embodiments of the present disclosure some other type of feature selection algorithm may be employed, and it will be clear to those skilled in the art, after reading this disclosure, how to make and use embodiments of the present disclosure that employ such alternative feature selection algorithms. It will further be clear to those skilled in the art, after reading this disclosure, which subtasks depicted in FIG. 15 can be performed simultaneously or in a different order than that depicted.

At subtask 1501, the system of FIG. 1B may arrange the eigenvectors (principal component coefficients) computed at subtask 1102 into a matrix that corresponds to the eigenvalues in descending order. At subtask 1503, the system may computer the principal component scores of the anatomical features as outputs to subtask 1402 of FIG. 14. After subtask 1504, execution may continue at subtask 1402.

Figure 16:
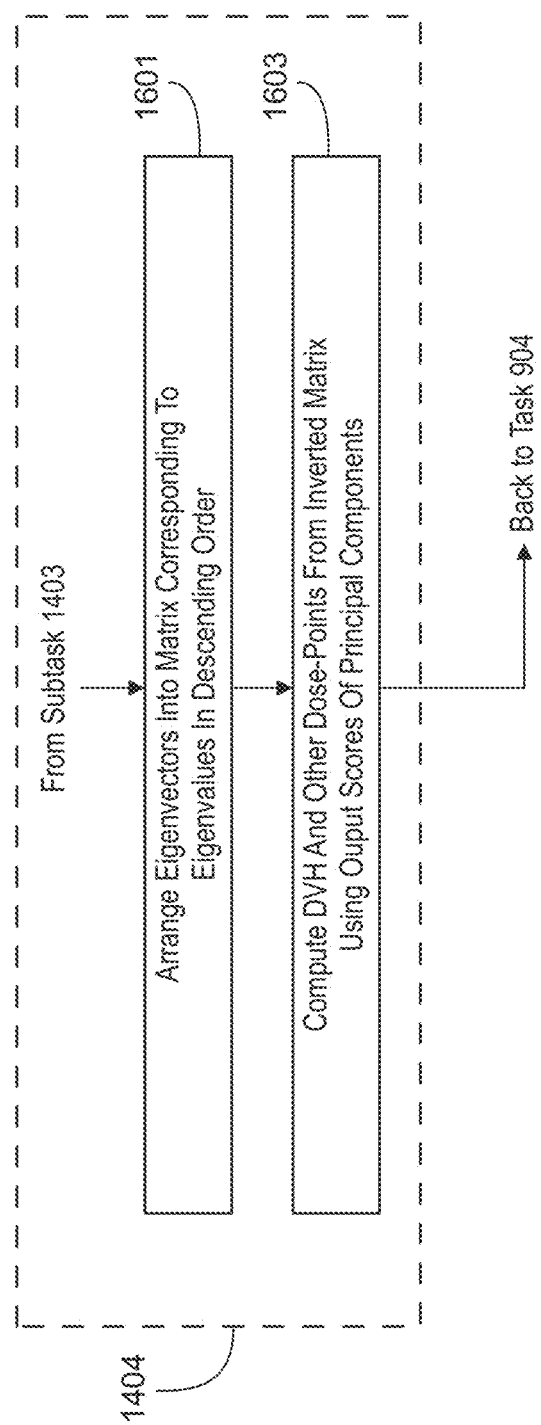
FIG. 16 depicts a detailed flowchart of subtask in accordance with the illustrative embodiment of the present disclosure.

FIG. 16 depicts a detailed flowchart of subtask 1404 in accordance with the illustrative embodiment of the present disclosure. As noted above, in accordance with the illustrative embodiment, a principal component analysis is employed as the feature selection algorithm in the subtasks of FIG. 16; however, as will be appreciated by those skilled in the art, in some other embodiments of the present disclosure some other type of feature selection algorithm may be employed, and it will be clear to those skilled in the art, after reading this disclosure, how to make and use embodiments of the present disclosure that employ such alternative feature selection algorithms. It will further be clear to those skilled in the art, after reading this disclosure, which subtasks depicted in FIG. 18 can be performed simultaneously or in a different order than that depicted.

At subtask 1601, the system of FIG. 1B may arrange the eigenvectors (principal component coefficients) computed at subtask 1104 into a matrix that corresponds to the eigenvalues in descending order.

At subtask 1602, the modeling subsystem 104 may computes a dose volume histogram (DVH) and other dose-points from the matrix using the output scores from subtask 1403.

After subtask 1602, execution continues back at task 904.

Figure 17:
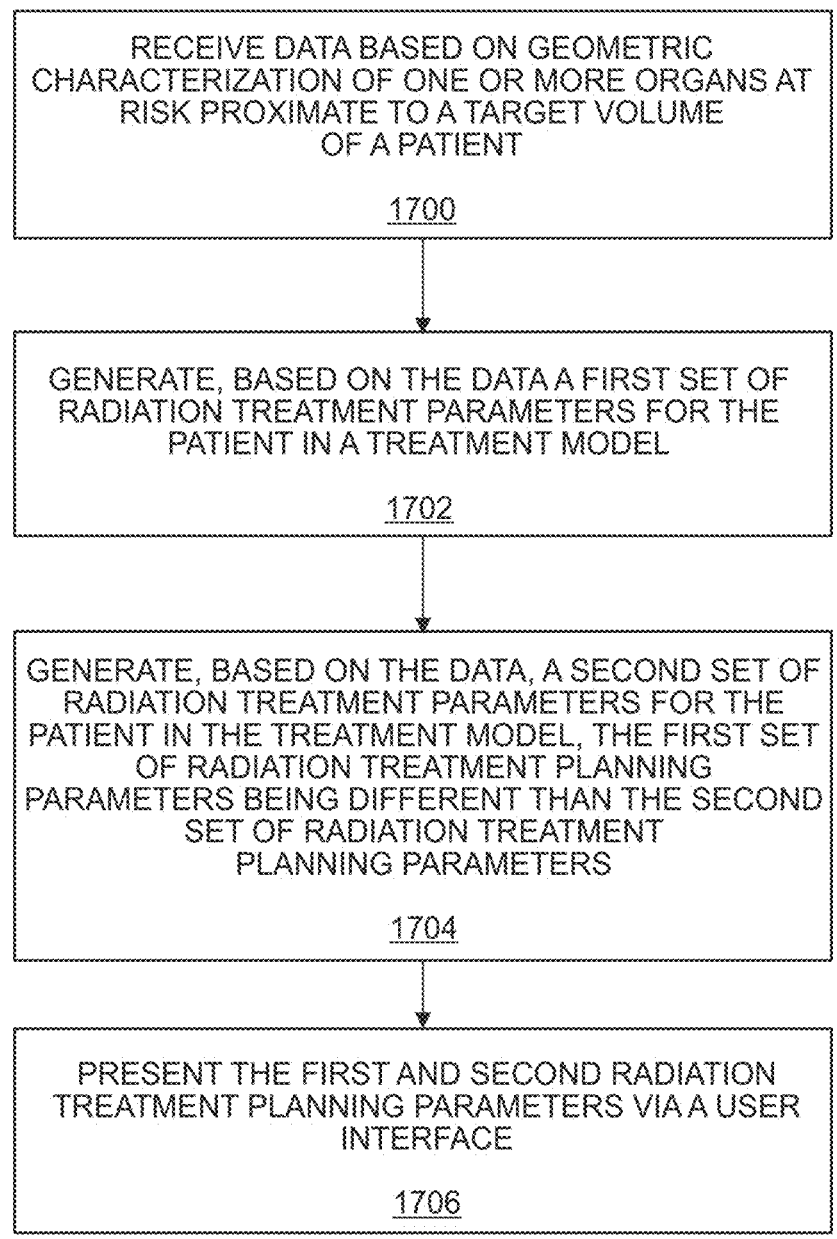
FIG. 17 illustrates a flowchart of an example method for radiation treatment planning in accordance with embodiments of the present disclosure.

In accordance with embodiments of the present disclosure, a treatment model may provide different trade-off options for review by a physician or planner. For example, the treatment model may be a trade-off dose model specifying different sets of radiation treatment parameters for a patient. FIG. 17 illustrates a flowchart of an example method for radiation treatment planning in accordance with embodiments of the present disclosure. The method is described as being implement by the training modeling subsystem 104 shown in FIG. 1, although it should be understood that the method may alternatively be implemented by any suitable component or computing device.

Referring to FIG. 17, the method includes receiving 1700 data based on anatomy and geometric characterization of one or more organs at risk proximate to a target volume of a patient. For example, the system of FIG. 1B may receive the data from the database 102. The geographic characterization may associate each of multiple distances from the target volume with a respective percentage for the volume of the one or more organs at risk. The data may include, but is not limited to, the size of the target volume and the respective sizes and shapes of the one or more organs at risk. Further, the radiation treatment planning parameters are represented by at least one of a dose distribution and a dose volume histogram. The radiation treatment planning parameters may be generated based on a predictive model. Step 1700 may include receiving patient anatomy features based on anatomy and geometric characterization of one or more OAR relative to PTV or vice versa. Further examples include receiving patient treatment dose prescriptions, and other patient treatment information (e.g., organ physiological function, other diseases and condition, etc.).

The method of FIG. 17 includes generating 1702, based on the data, a first set of radiation treatment parameters for the patient in a treatment model. Continuing the aforementioned example, the system of FIG. 1B may generate a set of radiation treatment parameters based on the data. Treatment plan parameters may include, but are not limited to, DVHs, other dose parameters, etc. for PTV and OARs.

The method of FIG. 17 includes generating 1704, based on the data and knowledge, a second set of radiation treatment parameters for the patient in the treatment model. The first set of radiation treatment planning parameters are different than the second set of radiation treatment planning parameters. Continuing the aforementioned example, the system of FIG. 1B may generate another set of radiation treatment parameters based on the data. This other set of radiation treatment planning parameters may be different than the initial set. By review of the different sets, a physician or planner may compare differences between the use of different parameters for a treatment plan. The physician or planner may modify a dose prescription for a specific organ at risk based on a review of the different sets of parameters. The second set or more of model generated treatment parameters may include trade-off options. Example treatment plan parameters include DVHs, other dose parameters, etc. for PTV and OARs.

The method of FIG. 17 includes presenting 1706 the first and second radiation treatment planning parameters via a user interface. Continuing the aforementioned example, the training modeling subsystem 104 may present the planning parameters and/or data relating thereto via a user interface 108. The results of steps 1702 and 1704 may be provided by displaying DVH curves, numerical dose/DVH values, or curves and numbers overlaid with guidelines.

As will be appreciated by those skilled in the art, although the illustrative embodiment is disclosed in the context of a single target volume, the techniques of the illustrative embodiment can easily be adapted by one skilled in the art to accommodate patients having a plurality of target volumes.

As will further be appreciated by those skilled in the art, although the illustrative embodiment employs principal component analysis as the feature selection algorithm, some other embodiments of the present disclosure may employ some other type of data dimension reduction techniques, such as multi-dimensional scaling, and it will be clear to those skilled in the art, after reading this disclosure, how to make and use such alternative embodiments.

As will yet further be appreciated by those skilled in the art, although the geometric characterizations of the illustrative embodiment may be expressed as distances in Euclidean space, the distances are in fact general measurements that may be expressed in some other type of space (e.g., a distance space distorted by radiation beam geometry, etc.), and it will be clear to those skilled in the art, after reading this disclosure, how to make and use embodiments that employ such alternative distance spaces. The geometric characterization also includes shape features such as target to OAR angles, enclosures, etc.

As will still further be appreciated by those skilled in the art, although the illustrative embodiment is disclosed in the context of general intensity-modulated radiation therapy (IMRT), the techniques of the illustrative embodiment can be employed for both static gantry angle intensity-modulated radiation therapy (IMRT) and rotation gantry volumetric modulated arc therapy (VMAT), as well as other types of radiation therapy, including proton therapy technique, TOMOTHERAPY™ technique and ACCURACY™ technique.

Given the patient specific information and standard dose prediction for each OAR, the physician can use the trade-off dose model to modify the dose prediction for a specific OAR. The population based OAR toxicity data may also be included here to assist the physician to make the complex trade-off decision. For any change in one OAR's dose prediction, the dose trade-off model may predict its impact by updating the dose predictions for the PTV and other OARs. The process can continue until the physician finishes the trade-off process.

The trade-off dose model may include one or more of the patient anatomical information. Such information includes, but is not limited to, OAR volumes, PTV volumes, fraction of OAR volumes overlapping with PTV (overlap volume), fraction of OAR colmes outside the treatment fields (out-of-field volumes), fraction of OAR volumes that relate critical toxicity data points, distance to target histogram (DTH) in Euclidean system or other non-Euclidean metrics, distance of target to OAR histogram (DOH) in Euclidean system or non-Euclidean metrics, tightness of the geometric enclosure of PTV surrounding OAR, other shape descriptions, combinations thereof and the like.

The dose parameters that are included in the trade-off model may include one or more of the following measures: dose distribution calculated from a plan generated using dose prediction model, or by an expert planner for this patient, or from Pareto-optimal plans generated for patients; simulated dose distributions from previous patient treatment plans using a machine learning algorithm; specific 3D isodose lines positions and volumes; 3D isodose values at specific anatomical points; PTV dose homogeneity; DVHs; dose volume points (e.g., mean dose, median dose, max dose, dose corresponding to 30% volume, etc.); dose gradient around OAR and PTV; partial dose gradient around one OAR, biological equivalent dose of the tumor volume and OARs, combinations thereof, and the like.

The trade-off prediction model can output the potential trade-off options for physician and planner to review. The options may include, but are not limited to, the following features: simulated dose distributions from previous patient treatment plans using a machine learning algorithm; specific 3D isodose lines' positions and volumes; 3D isodose values at specific anatomical points; PTV dose homogeneity; DVHs; dose volume points (e.g., mean dose, median dose, max dose, dose corresponding to 30% volume, etc.); dose gradient around OAR and PTV; partial dose gradient around one OAR; tumor control probability (TCP) of the tumor volume and normal tissue complication probability (NTCP) of an OAR; biological equivalent dose of the tumor volume and OARs, combinations thereof and the like.

Another aspect of the present disclosure a method for enhancing the quality of existing training plans comprising, consisting of, or consisting essentially of ensuring that each plan achieves Pareto optimal. It is important that the plans used to train the predictive models are of high quality. One strategy to develop high quality training databases comprises selecting clinically accepted plans that are designed by experienced planners and approved by experienced physicians. It is recognized that even these clinically accepted plans are not of the same quality. Additional strategies are developed to improve the quality of the existing plans in a preprocessing step. One possible strategy comprises extracting a set of key criteria from an existing plan and applying multi-criteria optimization to ensure that the new plan solution is Pareto optimal. The Pareto fronts of the MCO can be carefully mapped in this application since the speed is not a constraint. Alternatively, plans generated using Pareto-front search algorithms are supplied to the training model.

In other embodiments, the predictive models may be incrementally updated as new plans are generated. A network of plan databases from multiple treatment centers can be set up to enable efficient and large scale learning of the predictive models. Similarly, and in other embodiments, the guideline models may be updated as new results are published. The experience models will also be updated from more experienced planners and physicians. Advanced web-based platforms (e.g., crowd sourcing) may allow for collaborative acquisition, update, and verification of the computerized models.

Another aspect of the present disclosure provides a system for collecting all evidence, experience, and knowledge of a patient comprising, consisting of, or consisting essentially of a distributed and collaborative web-based platform, the platform converting the evidence, experience and knowledge into computerized models with a process for continuous updates and verification.

Yet another aspect of the present disclosure provides a system for providing decision support using models as described herein, the system continuing to deliver new evidences to the modeling system for incremental learning and enhancement of the computerized models.

In accordance with embodiments, trade-off modeling can involve determining a dose sparing trade-off between different organs at risk. As an example, sparing of single-side parotid gland is a common practice in head-and-neck (HN) intensity modulated radiation therapy (IMRT) planning. Disclosed herein is a mathematical model and system for predicting achievable dose sparing in parotid glands in HN IMRT planning that incorporates single-side sparing considerations based on patient anatomy and learning from prior plan data.

In experimentation, among 68 HN cases analyzed retrospectively, 35 cases had physician prescribed single-side parotid sparing preferences. The single-side sparing model was trained with cases which had single-side sparing preferences, while the standard model was trained with the remainder of cases. A receiver operating characteristics (ROC) analysis was performed to determine the best criterion that separates the two case groups using the physician's single-side sparing prescription as ground truth. The final predictive model (combined model) takes into account the single-side sparing by switching between the standard and single-side sparing models according to the single-side sparing criterion. The models were tested with 20 additional cases. The significance of the improvement of prediction accuracy by the combined model over the standard model was evaluated using the Wilcoxon rank-sum test.

Using the ROC analysis, the best single-side sparing criterion is (1) the predicted median dose of one parotid is higher than 24 Gy; and (2) that of the other is higher than 7 Gy. This criterion gives a true positive rate of 0.82 and a false positive rate of 0.19, respectively. For the bilateral sparing cases, the combined and the standard models performed equally well, with the median of the prediction errors for parotid median dose being 0.34 Gy by both models ($p=0.81$). For the single-side sparing cases, the standard model overestimates the median dose by 7.8 Gy on average, while the predictions by the combined model differ from actual values by only 2.2 Gy ($p=0.005$). Similarly, the sum of residues between the modeled and the actual plan DVHs is the same for the bilateral sparing cases by both models ($p=0.67$), while the standard model predicts significantly higher DVHs than the combined model for the single-side sparing cases ($p=0.01$).

The combined model for predicting parotid sparing that takes into account single-side sparing improves the prediction accuracy over the previous model. For head-and-neck (HN) cancer radiation therapy, IMRT has significant advantage in reducing the severity and incidence of xerostomia over three-dimensional conformal radiotherapy because of improved parotid sparing. The current consensus clinical guidelines for parotid sparing are derived from population based toxicity studies, such as the QUANTEC and RTOG. Studies have shown that gland function reduction occurs minimally at 10-15 Gy mean dose, gradually increases at 20-40 Gy mean dose range, and becomes severe when mean dose >40 Gy. The QUANTEC guideline recommends that at least one parotid gland should receive less than 20 Gy mean dose, or both parotid glands should receive less than 25 Gy mean dose. In addition, the mean dose to each parotid gland should be kept as low as possible. The parotid gland dose sparing objectives recommended by RTOG are: at least one parotid gland should receive less than 26 Gy mean dose, or 20 cc of the combined volume of the left and right parotids should receive no more than 20 Gy dose, or alternatively at least 50% of the one gland receive no more than 30 Gy. As we can see, both guidelines include criterion to spare single side parotid as well as to spare bilateral parotids. Meeting either one of them can usually avoid severe xerostomia. The decision of which criterion to use is often left to the clinician to make during treatment planning.

In clinical practice, the physicians often visually inspect the patient-specific anatomy. In cases where the location of the primary tumor or bulky lymph nodes causes large overlap of one parotid with the planning target volume (PTV) thus it is unlikely to spare both parotid glands, they will choose to reduce or remove the dose constraint to one parotid in exchange for more sparing in the salvageable parotid on the contralateral side for a more favorable radiobiological outcome. Herein, the term "single-side sparing" may refer to the special consideration used to plan these cases, and the term "bilateral sparing" may refer to the cases where the physicians choose to spare both parotid glands.

A number of methods have been developed to predict the achievable organ-at-risk (OAR) dose sparing in HN IMRT treatment planning based on patients' anatomical features and past planning experiences. Knowledge-based mathematical models, as disclosed herein, may be used to describe the quantitative correlations between patient anatomical features and the achievable dose sparing in a number of OARs. These correlations represent the clinical acceptable tradeoff between PTV dose coverage and the dose sparing in these OARs. Disclosed herein are methods and systems that account for the sparing of single side parotid in HN IMRT planning. The sparing of single side parotid reflects a "break point" in the normally continuous tradeoff between the left and right parotids and it is a special case of dose sparing tradeoff between different OARs. Data disclosed herein shows that this type of special, discontinuous tradeoff between left and right parotids is actually a common practice in HN IMRT planning.

In accordance with embodiments, systems and methods disclosed herein may be applied for predicting dose sparing in parotid glands. Models disclosed herein may incorporate single-side sparing considerations so that it can more closely reflect the clinical planning tradeoffs and decisions. This model provides a quantitative criterion for automatic determination of cases suitable for single-side parotid sparing and accounts for the extra dose sparing in the salvageable parotid of these cases.

In an experiment, sixty-eight HN patients were retrospectively retrieved for training OAR dose prediction models, under an Institutional Review Board (IRB) approved protocol. The prescription was 44-50 Gy to primary PTV and 66-70 Gy to boost PTV. These cases include oropharynx, oral cavity, hypopharynx, and larynx tumors. Nasopharynx tumor cases are not included in this study because they usually involve an additional set of critical organs different from other HN cancer types and the correlation between parotid sparing and patient anatomical features is also somewhat different. There was no institutional template for dose constraints in HN IMRT planning. Instead, the dose constraints were prescribed case by case by the physicians after careful examination of patient anatomy and indications. In 35 of these 68 cases physicians prescribed single-side sparing preferences, where the dose constraints were indicated as "minimize when possible" or "no constraint" to the unsalvageable side of the parotid. The dose sparing to the salvageable side was prescribed with tighter constraints and was emphasized during planning by finding the highest level of dose sparing for the parotid without sacrificing the PTV coverage.

For model validation, 20 additional cases, 10 cases with physician prescribed single-side sparing preferences and 10 without, were used. These cases had the same characteristics as those used for model training.

In the previous study, we have successfully built a non-linear model that predicts OAR DVH sparing using an array of anatomical features. This model did not distinguish single-side sparing cases from bilateral sparing cases; all HN cases were trained together to build a generic OAR sparing model. Implementation of this model was detailed in the previous work. In summary, a number of patient's anatomical and dosimetric features were considered in the model (Table I below). In addition to volume features, the features of distance to target histogram (DTH) were extracted by principal component analysis. The prescriptions for PTV dose coverage and dose homogeneity were included as explanatory factors to account for the tradeoff between PTV coverage and OAR sparing. A step-wise multiple regression method was used to select the most significant patient features which influence the OAR dose sparing in the training plans.

TABLE I

List of Patient Anatomical and Dosimetric Features in the Model
Anatomical and Dosimetric Features Distance to primary and boost target histogram
Position of OAR relative to the treatment fields
OAR, position and boost PTV volumes
Fraction of OAR volume overlapping with PTVs (overlap volume)
Fraction of OAR volume outside the treatment fields (out-of-field volume)
PTV dose coverage and dose homogeneity The primary and boost plans within one treatment course may be modeled separately. However, physician's dose constraints are usually prescribed on the summed plans which combine the primary and boost plans for the entire treatment courses. In this study, two predictive models were developed to characterize the dependence of parotid dose sparing on patient anatomical features in the summed plans. The single-side sparing model may be trained by using the spared parotids data in physician prescribed single-side sparing cases, while the standard model was trained with the remainder of cases for which the planning objectives is to spare bilateral parotids. The final model is the combination of these two models. Given a patient case, the combined model initially predicts parotid dose sparing using the standard model. Then, if the predicted parotid dose satisfies certain single-side sparing criterion, the combined model may apply the single-side sparing model to provide prediction of the parotid dose that takes into account the effects of single-side sparing.

In clinical treatment planning, cases with single-side parotid sparing tend to have large overlap between PTV and one side of the parotid, which result in high dose in that parotid. Therefore, in this study we use the median dose (D50) predicted by the standard model as criterion for triggering single-side sparing. The single-side sparing criterion in this study is formulated by median dose instead of mean dose because the physicians prescribe parotid dose sparing constraint in terms of median dose in our institution. Let $D_{50}^{L,Std}$ and $D_{50}^{R,Std}$ represent the predicted median dose in the left and right parotids, respectively, and $d_1$ and $d_2$ be the thresholds doses for the two parotids. A case is identified as a single-side sparing case if the following condition is satisfied:

$$(D_{50}^{L,Std} > d_1 \text{ and } D_{50}^{R,Std} > d_2) \text{ or}$$

$$(D_{50}^{L,Std} > d_2 \text{ and } D_{50}^{R,Std} > d_1).$$

The "or" in the above condition specifies that the condition can be triggered either by $d_1$ applied to right parotid and $d_2$ to left parotid or vice versa.

To determine the best decision threshold, a receiver operating characteristics (ROC) analysis was performed by varying the threshold values and comparing the model-based classification at different thresholds against physician's single-side sparing prescription. The decision criterion were determined by the point on the ROC curve which maximizes the likelihood ratio, which is defined as: likelihood ratio=sensitivity/(1−specificity). A larger value of likelihood ratio means the physician is more likely to prescribe a case as single-side sparing case if the case satisfies the criterion.

Another study has shown strong correlation between portion of parotid volume overlapping with PTV and parotid mean dose. It suggests that sparing the parotid which has large overlap with PTV (>21% of parotid volume) may lead to inadequate PTV coverage. Thus, we tested the alternative method to identify single-side sparing cases by directly using the parotid-PTV overlap volume. A case would be identified as a single-side sparing case if the portion of parotid volume which overlaps with the primary PTV were greater than a threshold value. This method was compared with the criterion based on the predicted parotid median dose by a ROC analysis.

The combined model for parotid dose sparing may be constructed by combining the single-side sparing criterion, the standard and the single-side sparing models. When a case satisfies the single-side sparing criterion, the parotid with lower predicted D50 is chosen to be further spared and its value is predicted by the single-side sparing model.

To assess the effectiveness of the final model (the combined model) and its improvement over the standard model, validation tests were performed using the validation dataset. The validation dataset is outside the training database, with ten cases having single-side sparing preferences prescribed by physicians and ten cases not. Both the standard and combined models are applied to these cases. The differences between the model-predicted values and the actual plan values are calculated to evaluate the prediction accuracy.

Two quantitative measures were calculated to compare the differences in the modeled and actual planned DVHs. The first measure uses D50 as an indicator of dosimetric prediction accuracy. For the combined and standard models, respectively, the difference between the predicted D50 and actual clinical values was calculated for each validation case and the distribution of the differences was visualized in box plots. Furthermore, for the two sets of differences computed from the two models, a Wilcoxon rank-sum test was performed to assess the significance of improvements in prediction accuracy.

While the median of the parotid median dose differences between the combined model prediction and the actual plan values was utilized to assess the prediction accuracy at a specific dosimetric point, the sum of residues (SR) is used as the second measure to quantify the overall difference of the entire DVH curves between the modeled and the actual plan's. SR may be defined as the sum of the differences between two DVHs over each dose bin (calculated at 1% prescription dose interval):

$$SR = \Sigma_{D=0}^{\infty} [V^{Actual}(D) - V^{Model}(D)] \cdot \Delta D,$$

where $V^{Actual}(D)$ and $V^{model}(D)$ are the fractional volume values corresponding to normalized dose D on the actual and modeled DVHs, respectively, and $\Delta D$ is the dose bin width. A positive SR value indicates the actual clinical DVH is higher than the modeled DVH on average, and vice versa. The Wilcoxon rank sum tests were again performed to show the significance of any separation between the two models.

Figure 18:
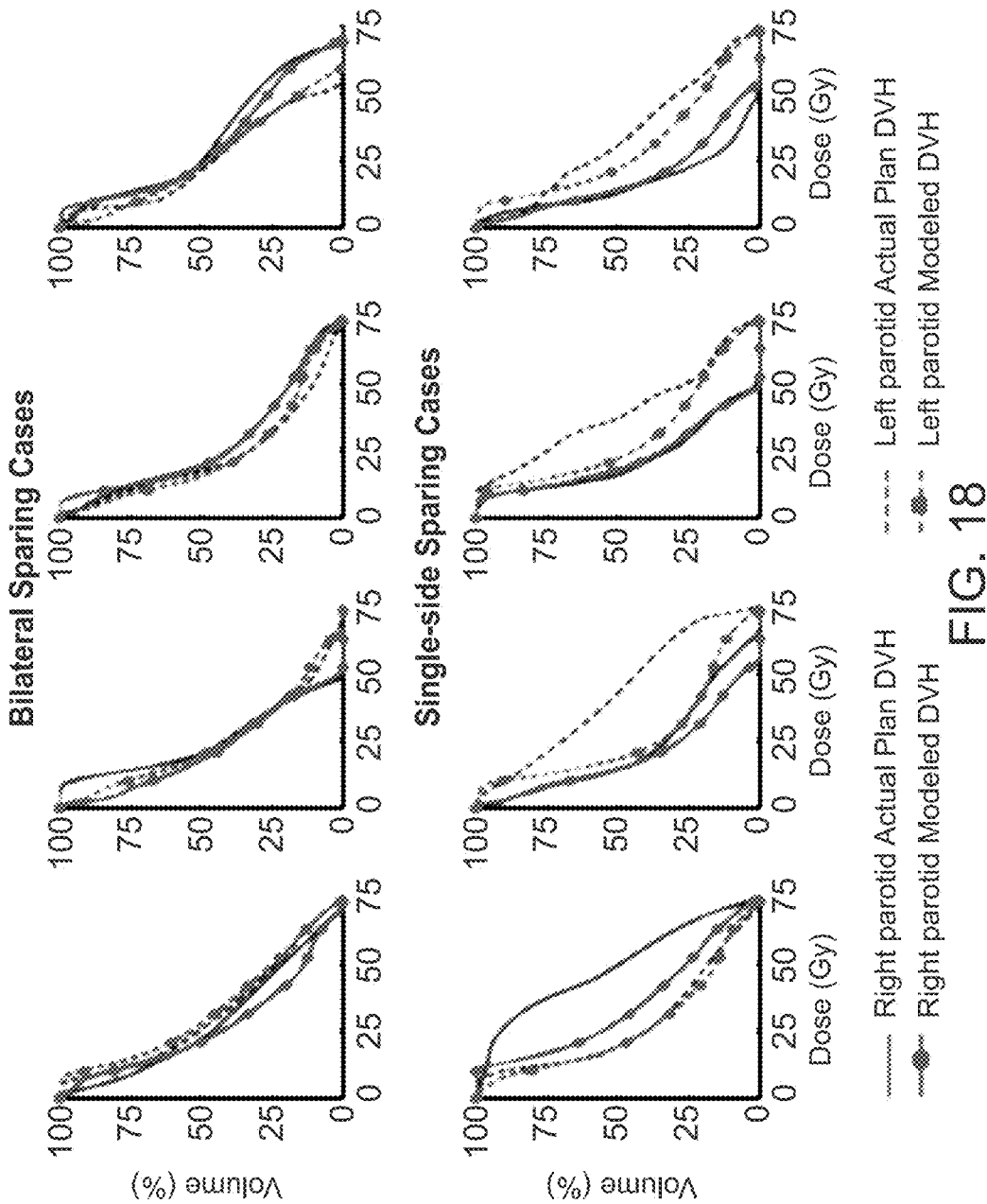
FIG. 18 are graphs of actual plan DVHs and model predicted DVHs of both side parotids in four examples of single-side sparing cases and four examples of bilateral sparing cases from the training data sets.

Both standard and single-side sparing models describe the dependency of the first three principal component scores (PCS) of the parotid DVHs on a number of patient factors. The determination coefficients $R^2$ of the standard models that account for the first two PCS are: PCS1: 0.81, PCS2: 0.68. Those of the single-side sparing models are: PCS1: 0.72, PCS2: 0.45. Examples of four single-side sparing cases and four bilateral sparing cases from the training data sets are shown in FIG. 18, which illustrates graphs of actual plan DVHs and model predicted DVHs of both side parotids in four examples of single-side sparing cases and four examples of bilateral sparing cases from the training data sets. The "nonspared" parotids are not used to train the single-side sparing model. They are shown in FIG. 18 to demonstrate the trade-off effect.

Figure 19:
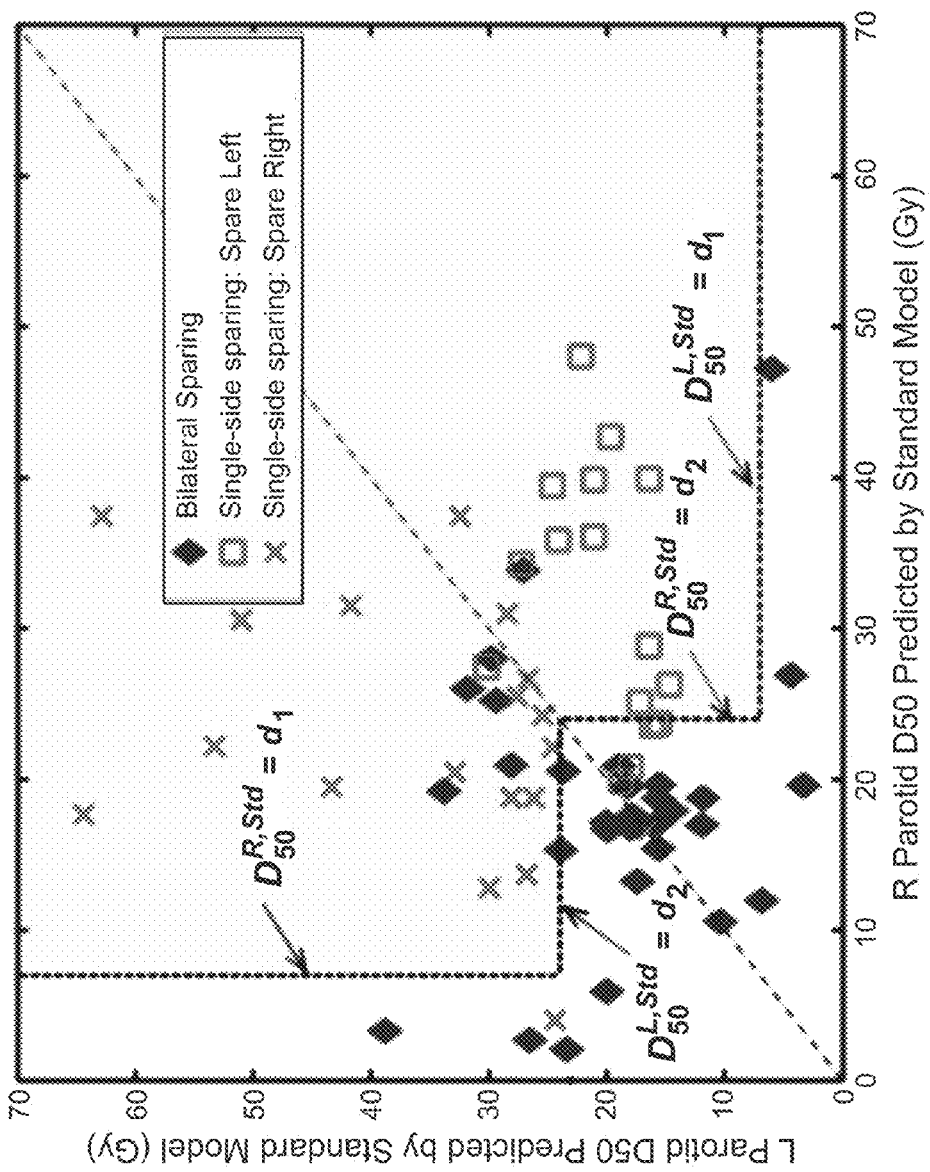
FIG. 19 is a graph of the dosimetric criterion for single-side parotid sparing.

The median dose values predicted by the standard model for the 68 cases are plotted in FIG. 19, which illustrates a graph of the dosimetric criterion for single-side parotid sparing. Each marker represents one patient plan. The single-side sparing region is the light gray area above the two L-shaped single-side sparing threshold lines. The median dose for the left parotid is represented by the Y-axis and that for the right parotid is represented by the X-axis. The single-side sparing thresholds $d_1$ and $d_2$ were varied and the true positive rate (TPR) and false positive rate (FPR) were calculated for each pair of thresholds by comparing the model classification against physician prescriptions (ground truth). The ROC curve is plotted in FIG. 20 as the solid curve. The area under curve (AUC) for the ROC is 0.87. On the ROC curve, the point with the true positive rate and false positive rate of TPR=0.82, FPR=0.19 was chosen. At this point, the likelihood ratio has a maximum at 4.3 and it corresponds to the threshold of $d_1$=25 Gy and $d_2$=7 Gy. Thus a patient case may be considered a single-side sparing case if (1) the predicted median dose of one side parotid is greater than 24 Gy; and (2) the value for the other side is greater than 7 Gy. This single-side sparing region is visualized in FIG. 19 as the light gray area above the L-shaped threshold lines.

Figure 20:
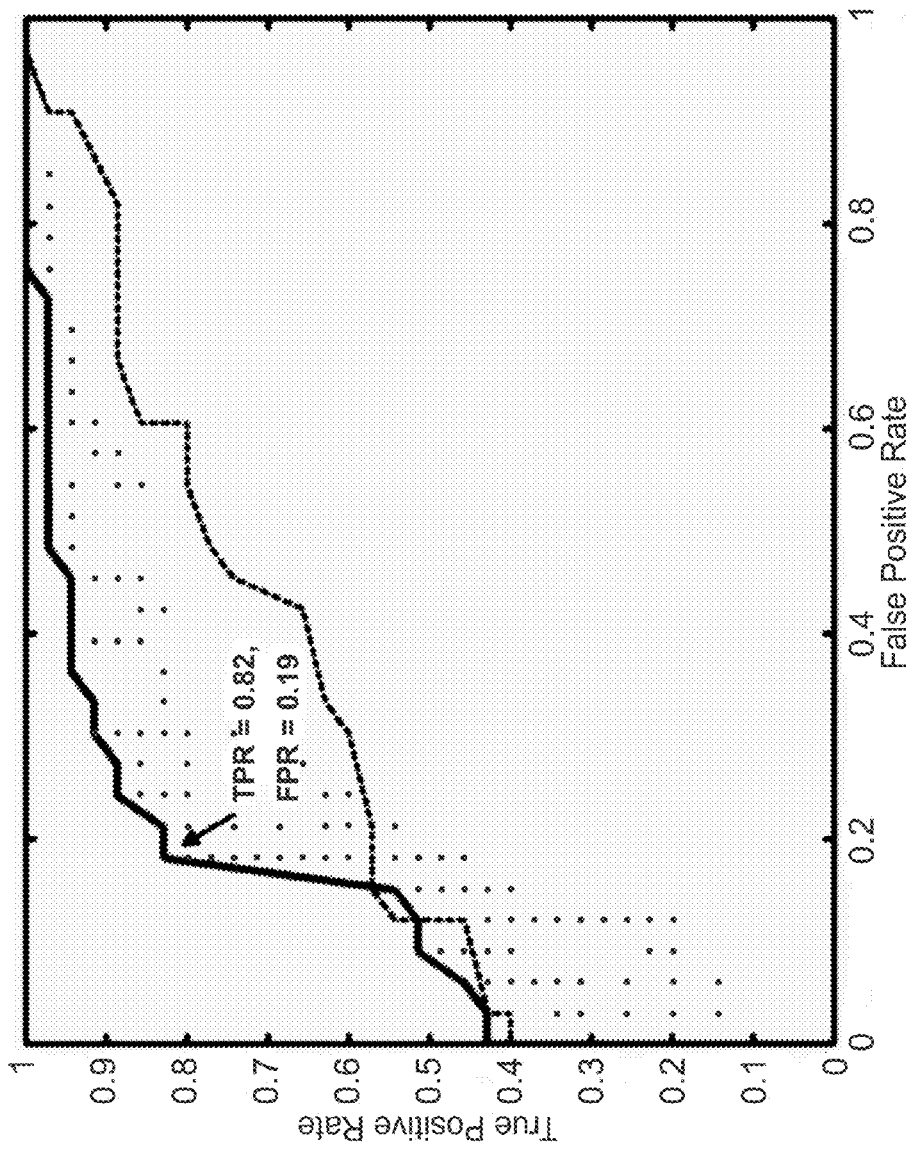
FIG. 20 is a graph of the ROC curve in solid that is constructed by varying the single-side sparing threshold $d_1$ and $d_2$ and comparing the threshold identified single-side sparing cases with the preidentified cases.

As a comparison, the ROC curve calculated by using the portion of parotid volume overlapping with PTV as criterion is also plotted in FIG. 20 as dashed curve. The data in the figure has an AUC of 0.73. The lower AUC value indicates the criterion based on predicted parotid median dose is more consistent with physician's clinical single-side sparing decisions.

With this threshold, 29 of the 35 physicians prescribed single-side sparing cases (square and "X" markers in FIG. 19) are correctly identified as single-side sparing cases, while 27 of the 33 physicians prescribed bilateral sparing cases (diamond markers in FIG. 19) are correctly identified as bilateral sparing cases. Most misclassified cases are close to the diagonal line of the figure indicating high symmetry of the PTV to the left and right parotids. One single-side sparing case misclassified as bilateral sparing case has very low right parotid D50 (<5 Gy) and a left parotid D50 of about 25 Gy.

Within the ten validation cases which have physician prescribed single-side sparing preferences, seven cases were correctly classified. In those three misclassified cases, the predicted D50 for both parotids are in the ranges of 20-24 Gy. Also, the geometrical relationships of the left and right parotids with the PTV are very similar. This indicates that even though physician has prescribed single-side sparing based on his/her personal estimation, the clinical plan can to spare both parotids to less than the critical threshold of 24 Gy.

Within the ten validation cases without physician prescribed single-side sparing, eight cases were correctly classified. In the two misclassified cases, both the right parotid D50 were predicted at about 26 Gy, and the left parotid median doses were predicted at 21 and 19 Gy, respectively. These two cases were just above the single-side sparing threshold of 24 Gy, and were clinically interpreted by physician as bilateral sparing cases.

Figure 21A:
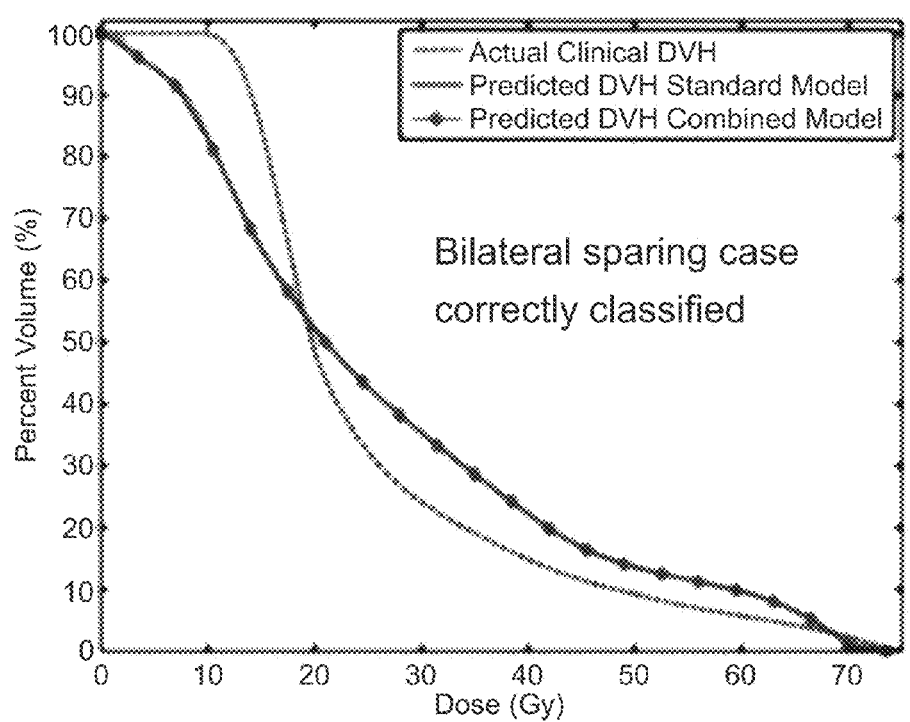
FIGS. 21A, 21B, 21C, and 21D are graphs of two examples of correctly classified cases and two examples of misclassified cases.
Figure 21B:
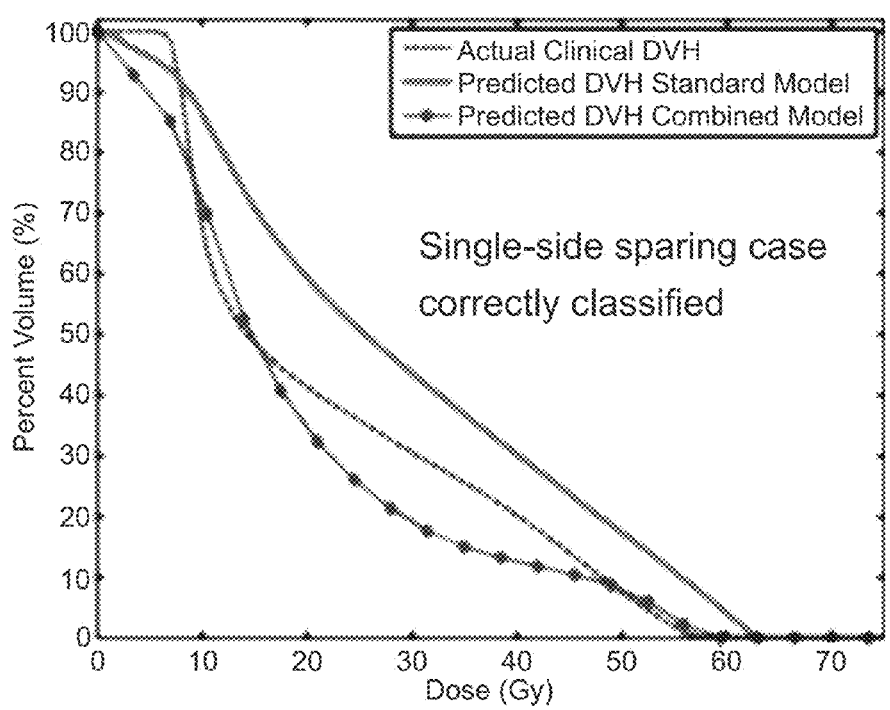
Figure 21C:
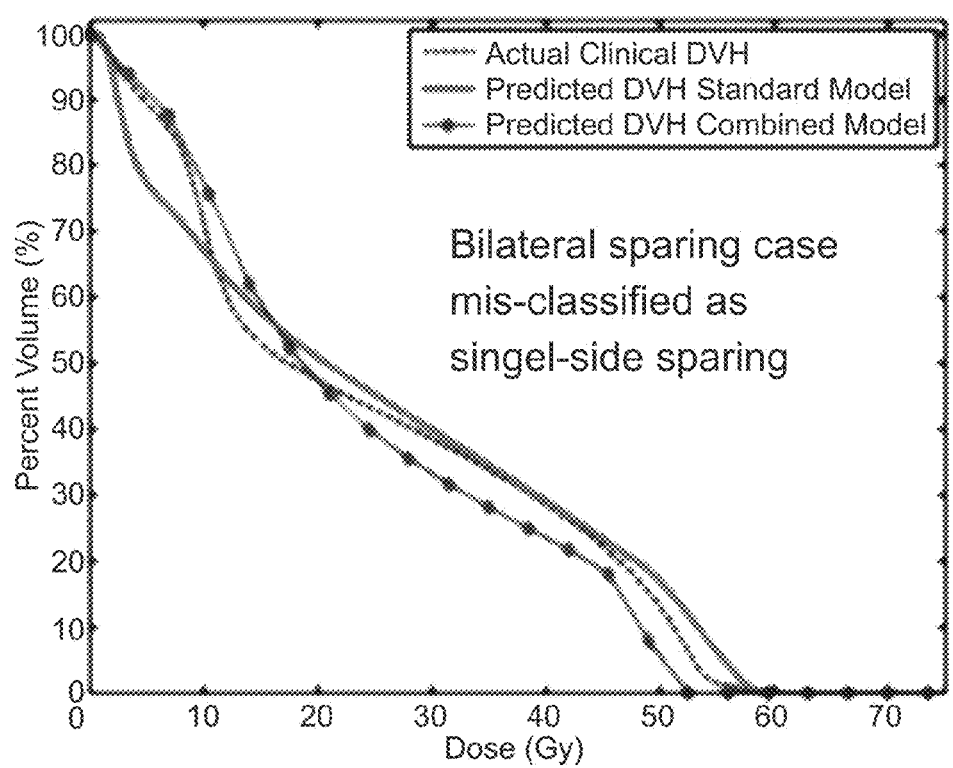
Figure 21D:
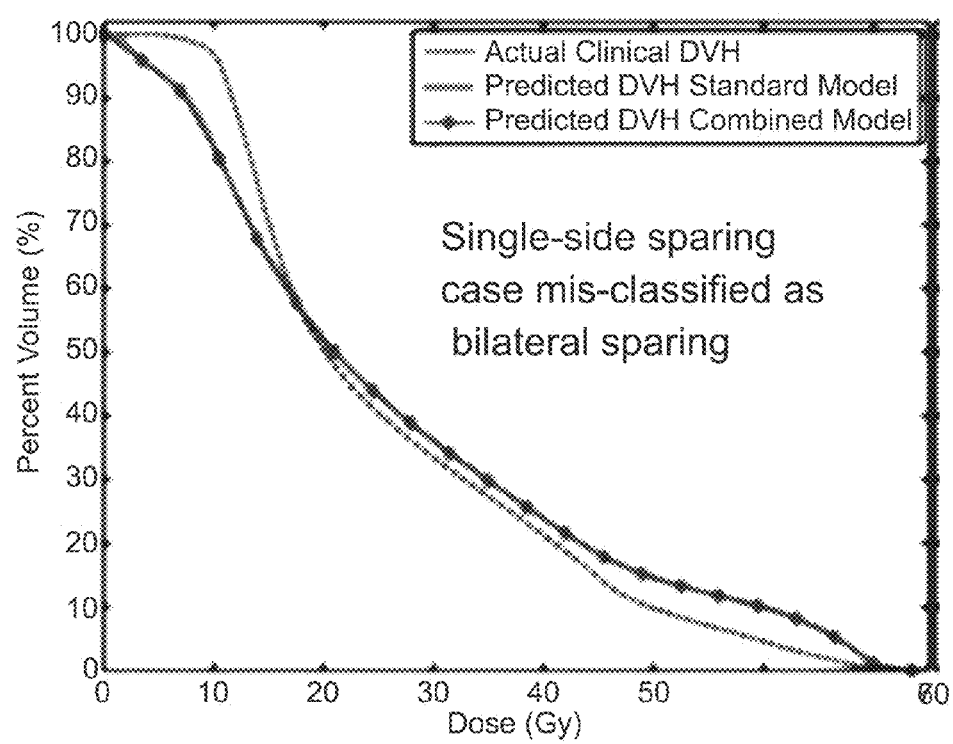

Two examples of correctly classified cases and two examples of misclassified cases are shown in FIGS. 21A-21D, which illustrates graphs of two examples of correctly classified cases and two examples of misclassified cases. Graph (a) and (c) show physician prescribed bilateral sparing cases. The graphs of FIGS. 21B and 21D show physician prescribed single-side sparing cases. As shown in FIGS.

21A-21D, for bilateral sparing cases, both the standard and the combined models predict closely to clinical plan values [graphs of FIGS. 21A and 21C]. For single-side sparing cases, the combined model is much closer to clinical values when single-side sparing is clearly favored in clinical situations as in FIG. 21B. On the other hand, when single-side sparing is borderline necessary (parotid D50 being close to 24 Gy) as shown in FIG. 21D, both the standard and combined models are close to clinical D50 values.

Figure 22A:
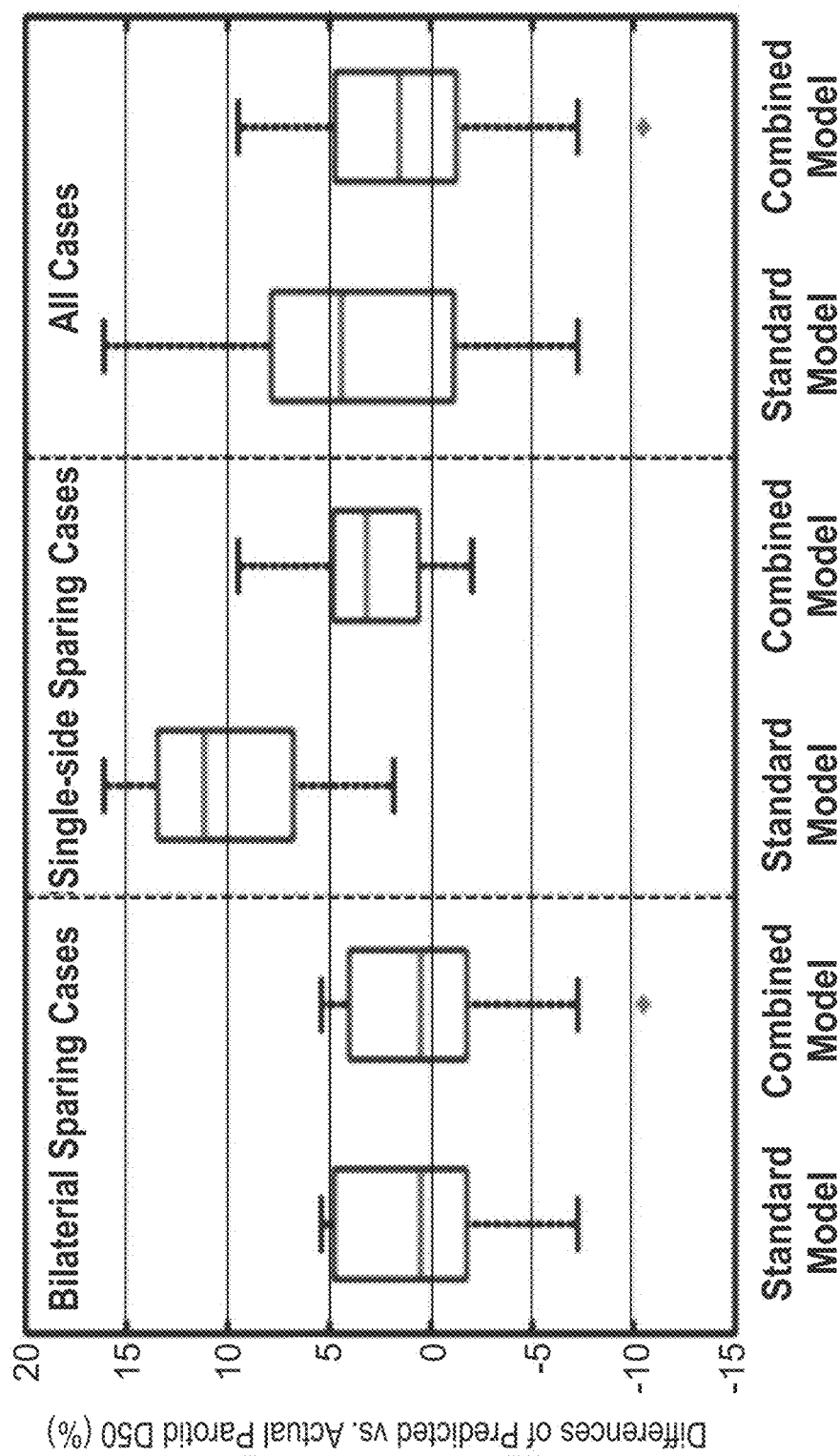
FIGS. 22A and 22B depict box plot showing prediction accuracies on parotid median does (D50) by the standard and combined model.
Figure 22B:
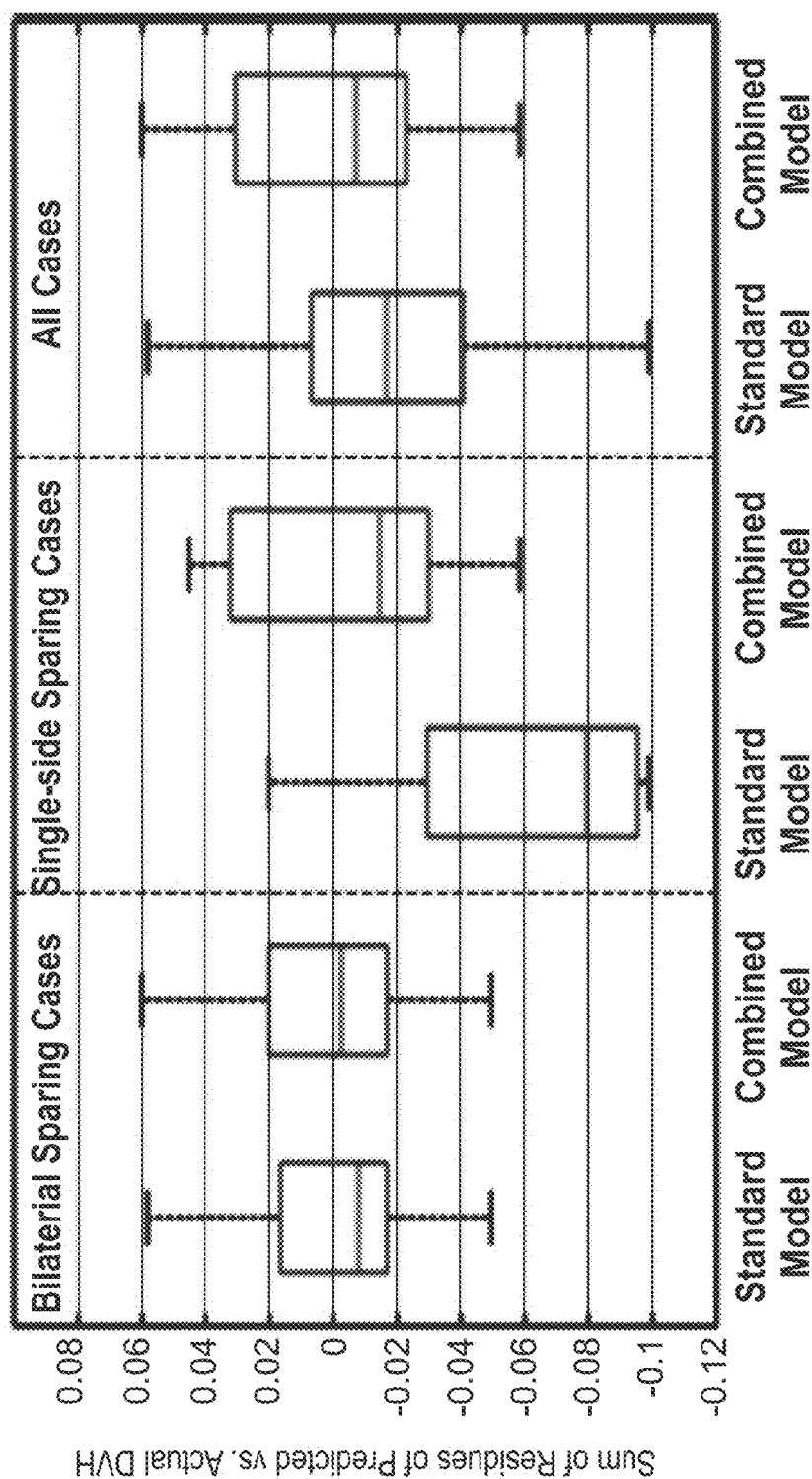

FIGS. 22A and 22B depict box plot showing prediction accuracies on parotid median does (D50) by the standard and combined model. The prediction error is the difference between the model-predicted values and the actual planned values, and is visualized in box plots for the bilateral sparing cases, single-side sparing cases, and all cases together. The plot of FIG. 22A shows differences of parotid median dose. The plot of FIG. 22B shows the sum of residues between the modeled and actual plan DVHs. The plot of FIG. 22A compares the prediction accuracies on parotid median dose between the standard and the combined model. The prediction error is the difference between the predicted median dose values and the actual planned values, and is visualized in box plots for the bilateral sparing cases, single-side sparing cases, and all cases together. In the figure, the horizontal bars inside the boxes indicate the locations of the median of the distributions, and the boxes represent the interquartile range (IQR) of the distributions (the 25% quartile to 75% quartile). Outliers, represented by crosses, are defined as the points more than 1.5 times IQR away from the box edge. The upper and lower extreme values are represented by the horizontal bars connected to the box.

For the bilateral sparing cases, the combined and the standard models performed equally well, with the median of the prediction errors being 0.34 Gy by both models (p=0.81). For the single-side sparing cases, the standard model overestimates the D50 by 7.8 Gy on average, while the predictions by the combined model differ from actual values by only 2.2 Gy (p=0.005). The differences between these two models are not significant when only the bilateral sparing cases are considered or when both the single-side sparing and bilateral sparing cases are considered together (p=0.81 and 0.11). However, the difference between these two models is significant (p=0.005) when single-side sparing cases alone are considered.

The modeled and actual planned DVH curves are compared using the SR index in FIG. 22B. Since the SR calculates the difference of the two DVH curves, a value close to zero indicates a close match between the modeled and the actual planned DVH curves. A positive SR value indicates the actual plan DVH has higher values (hotter) than the modeled DVH on average, and vice versa. The prediction accuracy of the combined model and the standard model is the same for the bilateral sparing cases: the medians of the SR for the two models are −0.002 and −0.009, respectively (p=0.67). For single-side sparing cases, the medians are −0.08 and −0.015, respectively, and are significantly different (p=0.01), which indicates the standard model predicts DVHs significantly higher than the actual planned DVHs. When all the cases are considered together, the medians are −0.018 and −0.007, respectively, and not significantly different (p=0.09).

IMRT planning can involve many different types of tradeoff situations. In addition to the dose sparing tradeoff between the left and right parotid glands, there are also indications in the experimental dataset that the parotid dose sparing is influenced by other OARs in some cases. For example, it can be seen that a lack of oral cavity or larynx constraints comes with a lower parotid dose. The effect of the tradeoff may be treated as the standard deviation of the regression model. It is also noted that, in most clinical cases, the priorities of sparing organs may not follow convention or templates; hence there is high consistency in most cases in terms of the prescriptions for OAR sparing constraints.

Single-side parotid sparing may be prescribed to loosen or eliminate dose constraint to one parotid in exchange for lower median (and mean) dose of the salvageable parotid on the contralateral side. In cases where the PTV mainly resides on one side of the neck, the contralateral side parotid may get little dose, thus there is no need to give up the parotid sparing on the ipsilateral side. These cases are shown along the long arms of the two "L" shapes in FIG. 19 (with the dose threshold of 7 Gy). For these cases, physician and planner often do not just spare single-side parotid. The only exception is in one case where sparing right parotid is emphasized by physician (shown as the "X" on the left side of the FIG. 19), with right parotid D50 getting 5 Gy and left parotid D50 getting about 25 Gy in the actual plan. Although single-side sparing is prescribed, the actual plan attempted to spare bilateral parotids and both DVHs agreed with the standard prediction model.

The single-side sparing classifications may not always agree with physician prescriptions. In most of these misclassified cases, the PTVs located at the center of the neck and the left and right parotids have very similar geometrical relationships to the PTVs. For these cases, the D50 are close to the diagonal line in FIG. 19, and are in the range of 20-30 Gy. In this scenario, the standard model and the combined model have very close predictions, as shown in graphs (c) and (d) of FIG. 21. Hence, physician preferences or model classifications may result in minimal dosimetric difference in clinical plans and the predicted DVHs by both models are close to the clinical DVHs. Most of the misclassified cases fall into this scenario and therefore do not significantly influence the final combined model. Another reason for the misclassification is that the physicians' clinical prescriptions for single-side sparing are used as the ground truth in this study. However, physicians make the single-side sparing prescriptions based on their clinical judgment using visual inspection of patient anatomy and personal estimation of the dose to the parotids before the final treatment plan and dosimetric data are available. Therefore, the physician preferences can be uncertain in some cases when parotid D50 are close to the 24 Gy thresholds.

If there were more objective and physician-independent criteria that determine exactly when single-side sparing may be preferred, those criteria may be used in a model. However, there is currently no consensus clinical criterion to guide the decision whether to spare single side parotid or to spare bilateral parotids. Current models of the radiobiological outcome of parotid sparing are also insufficient to provide an objective criterion. For example, there have been a number of studies to model the correlation between the normal tissue complication probability (NTCP) of parotid gland or salivary gland flow function and the dose volume data. The mean-dose-exponential model which describes the overall salivary function at 6 month after treatment as the mean of the bilateral parotids adequately fit the presented data. However, since both the ipsilateral and contralateral side parotids contribute to the overall salivary function equally in the model, this model cannot account for benefit of preferentially sparing the contralateral parotid which is a common clinical practice. Moiseenko et al. showed orderly dependences of overall whole-mouth salivary function on the mean dose to the highly spared gland for 3 and 12 months data. A logistic model was used to describe the incidence of Grade 4 xerostomia as a function of the mean dose of the spared parotid gland. While this model can be used to evaluate the biological benefit of single-side parotid sparing, it cannot be used to compare the biological benefit of single parotid sparing vs bilateral sparing because only spared parotid is considered. The present approach assumes that the high quality prior plans contain fundamentally good decisions made by physicians and seeks to capture the knowledge behind these decisions by learning from physician approved plans. In addition, the model and criterion obtained in this study reflect the clinical experience of multiple physicians in our institution because our dataset consists of plans done by several physicians. It is further noted that the goal of this work is to improve the accuracy of the ultimate combined models. With a change of threshold dose within 1-2 Gy, the cases which would be misclassified are most likely those with PTVs overlapping both parotids in a similar manner. For these cases, the predictions by the standard model and the combined model are very close, thus the prediction accuracy will not deteriorate significantly. A single-side sparing decision criterion may be expected to perform well for a range of different physicians and institutions.

For cases that clearly favor single-side sparing, the results show that the standard model significantly overestimates the parotid median dose. This indicates the different dosimetric features between the single-side sparing and bilateral sparing plans. In IMRT planning, the salvageable parotid achieved extra dose sparing by relaxing the constraint on the ipsilateral side parotid sparing. This extra dose sparing can be quantified by the difference of the standard and the combined model prediction, which is 5.6 Gy on average. By incorporating published guidelines on differential parotid sparing and learning the planning knowledge embedded in prior IMRT plans, modeling accuracy has significantly improved. The combined model switches between the standard and the single-side sparing models according to the single-side sparing criterion. The residual 2.2 Gy difference between the median dose predicted by the combined model and the actual plan value is an indication of the validation accuracy of the single-side sparing model. The larger validation error by the single-side sparing model is due to the larger case-by-case variation in the resulting parotid sparing when the planner tried to achieve extra sparing for the spared parotid. This variation is also reflected by smaller determination coefficient values of the single-side sparing model compared with the standard model.

Prediction models that "mimic" real clinical planning scenario are highly valuable to clinical IMRT planning as it can potentially lead to more efficient planning and optimal dose sparing. The time and effort spent on trial-and-error process for the search of optimal parotid sparing goals can be greatly reduced, even eliminated with a precise prediction model. Early studies have applied linear relationships between parotid-PTV overlap and mean dose in guiding treatment planning. It is noted that the modeling techniques and the models provided in the present disclosure are in general applicable to intensity modulated radiation therapy in any format, including volumetric modulated arc therapy and tomotherapy.

In an experiment, contributions of various patient anatomical features to the inter-patient OAR dose sparing variation in IMRT planning were systematically studied using machine learning method based on high quality prior plans. The dependence of anatomical factor on OAR dosimetric parameters is formulated into predictive models. The OAR dosimetric parameters generated by these predictive models represent the "best feasible" clinical outcomes based on past planning experience.

IMRT plans of 88 prostate, 106 HN, and 21 spine SBRT treatments were used to train the models. The final models were tested by additional 24 prostate and 48 HN plans. The model for spine SBRT was tested by the leave-one-out method.

For HN and prostate planning, significant patient anatomical features that can affect OAR sparing include, but are not limited to: the distance between OAR and PTV, the portion of OAR volume within an OAR specific distance range, the overlap volume between OAR and PTV, and the portion of OAR volume outside the primary treatment field.

For spine SBRT planning, a significant patient anatomical feature that affects cord sparing is the tightness of the geometric enclosure of PTV surrounding the cord and the homogeneity of PTV dose coverage.

The dosimetric parameters predicted for the test patient cases using the models were in agreement with those from the clinical plans in more than 75% of the cases.

The developed predictive models in experiments indicated substantial correlation between some important patient anatomical features and OAR dose sparing based on expert experiences. These models can be used as effective tools for evaluating the quality of treatment plans customized to individual patient's anatomy.

In accordance with embodiments, an evidence-based approach is provided to quantify the effects of an array of patient anatomical features of the PTVs and OARs and their spatial relationships on the inter-patient OAR dose sparing variation in IMRT plans by learning from a database of high quality prior plans.

Dependence of OAR DVHs on patient anatomical factors were formulized into feature models which were learned from prior plans by a stepwise multiple regression method. IMRT plans for 64 prostate, 82 HN treatments were used to train the models. Two major groups of anatomical features were considered in this study: the volumetric information and the spatial information. The geometry of OARs relative to PTV is represented by the distance-to-target histogram (DTH). Important anatomical and dosimetric features were extracted from DTH and DVH by principal component analysis. The final models were tested by additional 24 prostate and 24 HN plans.

Significant patient anatomical factors contributing to OAR dose sparing in prostate and HN IMRT plans have been analyzed and identified. The factors include the median distance between OAR and PTV, the portion of OAR volume within an OAR specific distance range, and the volumetric factors: the fraction of OAR volume which overlaps with PTV and the portion of OAR volume outside the primary treatment field.

Overall, the determination coefficients $R^2$ for predicting the first principal component score (PCS1) of the OAR DVH by the above factors are above 0.68 for all the OARs and they are more than 0.53 for predicting the second principal component score (PCS2) of the OAR DVHs except brainstem and spinal cord. Thus, the aforementioned set of anatomical features combined has captured significant portions of the DVH variations for the OARs in prostate and HN plans.

To test how well these features capture the inter-patient organ dose sparing variations in general, the DVHs and specific dose-volume indices calculated from the regression models were compared with the actual DVHs and dose-volume indices from each patient's plan in the validation dataset. The dose-volume indices compared were V99%, V85%, and V50% for bladder and rectum in prostate plans and parotids median dose in HN plans. It was found that for the bladder and rectum models, 17 out of 24 plans (71%) were within 6% OAR volume error and 21 plans (85%) were within 10% error. For the parotids model, the median dose values for 30 parotids out of 48 (63%) were within 6% prescription dose error and the values in 40 parotids (83%) were within 10% error.

Quantitative analysis of patient anatomical features and their correlation with OAR dose sparing has identified a number of important factors that explain significant amount of inter-patient DVH variations of OARs. These factors can be incorporated into evidence based learning models as effective features to provide patient-specific OAR dose sparing goals.

IMRT plans of 88 prostate cancer patients and 85 HN cancer patients (a total of 106 plans due to primary and boost PTV volumes) were retrospectively analyzed. Among these plans, 64 prostate and 58 HN patients were selected as training datasets and the other 24 prostate plans and 24 HN plans were set aside as validation datasets. Hence, there are no overlaps between the training datasets and the test datasets.

An array of anatomical features was analyzed to study their contributions to OAR dose sparing. The OARs and their anatomical features analyzed for this study are listed in Table II below.

TABLE II

The OARs and their anatomical features analyzed in this study

| Site | OAR | Anatomical Features |
|---|---|---|
| Prostate | Rectum<br>Bladder | Distance to target histogram (DTH) |
| HN | Parotids<br>Oral cavity<br>Larynx<br>Pharynx<br>Spinal cord<br>Brainstem<br>Mandible | OAR volumes<br>PTV volume<br>Fraction of OAR volume overlapping with PTV (overlap volume)<br>Fraction of OAR volume outside the treatment fields (out-of-field volume) |

Some of these anatomical-geometrical features were selected based on direct clinical experience in IMRT planning and optimization. In general, there are two major groups of anatomical features, the volumetric information and the spatial information. Aside from the volumetric features, the spatial information about the OARs and PTVs also affect the dose deposited in the OARs. The distance-to-target histogram (DTH) was included to encode the spatial relationship between the OARs and the PTV. In the Euclidean space, the value of DTH at a distance bin d is the fraction of OAR volume with its maximum distance to the PTV surface less than d. The simplest form of distance function r from an OAR voxel $v_i$ to the PTV surface, $r(v_i, \text{PTV})$ is:

$$r(v_i, \text{PTV}) = \min\{\|v_i - v_k\| \mid v_k \in s_{PTV}\}.$$

Negative signs are assigned to the distance values for OAR voxels inside PTV to indicate the intrusion of OAR into the PTV.

The dose deposited in an OAR voxel depends not only on its distance to PTV surface, but also on treatment of beam orientations. Two OAR voxels with the same distance to the PTV may have large difference in received dose, simply because one is in the beam's direction and the other is outside the radiation field. As examples, a prostate and a HN plan with calculated dose distributions are shown in graphs (a) and (b), respectively, of FIG. 23, which depicts (a) sagittal CT image of a prostate plan showing the contours of PTV, bladder, and rectum overlaid with isodose lines, (b) coronal CT image of a HN plan showing the contours of PTV, left and right parotids overlaid with isodose lines, (c) and (d) scatter plots of the correlation between dose and distance to PTV surface by the Euclidean distance metric and the non-Euclidean distance metric for the voxels inside (c) bladder in the prostate plan and (d) right parotid in the HN plan. It is noted that the spread of dose-distance correlation is reduced by the non-Euclidean distance metric. In the prostate plan, the bladder is positioned largely superior to the PTV. In the HN plan, a large part of the right parotid is superior to the right part of the PTV and far from the contralateral part of the PTV. In both plans, the OAR voxels outside the primary beam entrance (superior to the beam edge) receive only scatter dose, thus have different dose-distance correlation from other voxels.

To account for the beam configuration effect, a variable, non-Euclidean distance metric was applied. In this formulation, the distance function $r'(v_i, \text{PTV})$ is a function of the distance of the voxel to the PTV as well as the relative position of the voxel to the treatment beams:

$$r'(v_i, \text{PTV}) = r(v_i, \text{PTV}) + f(v_i, \text{PTV}).$$

Figure 23:
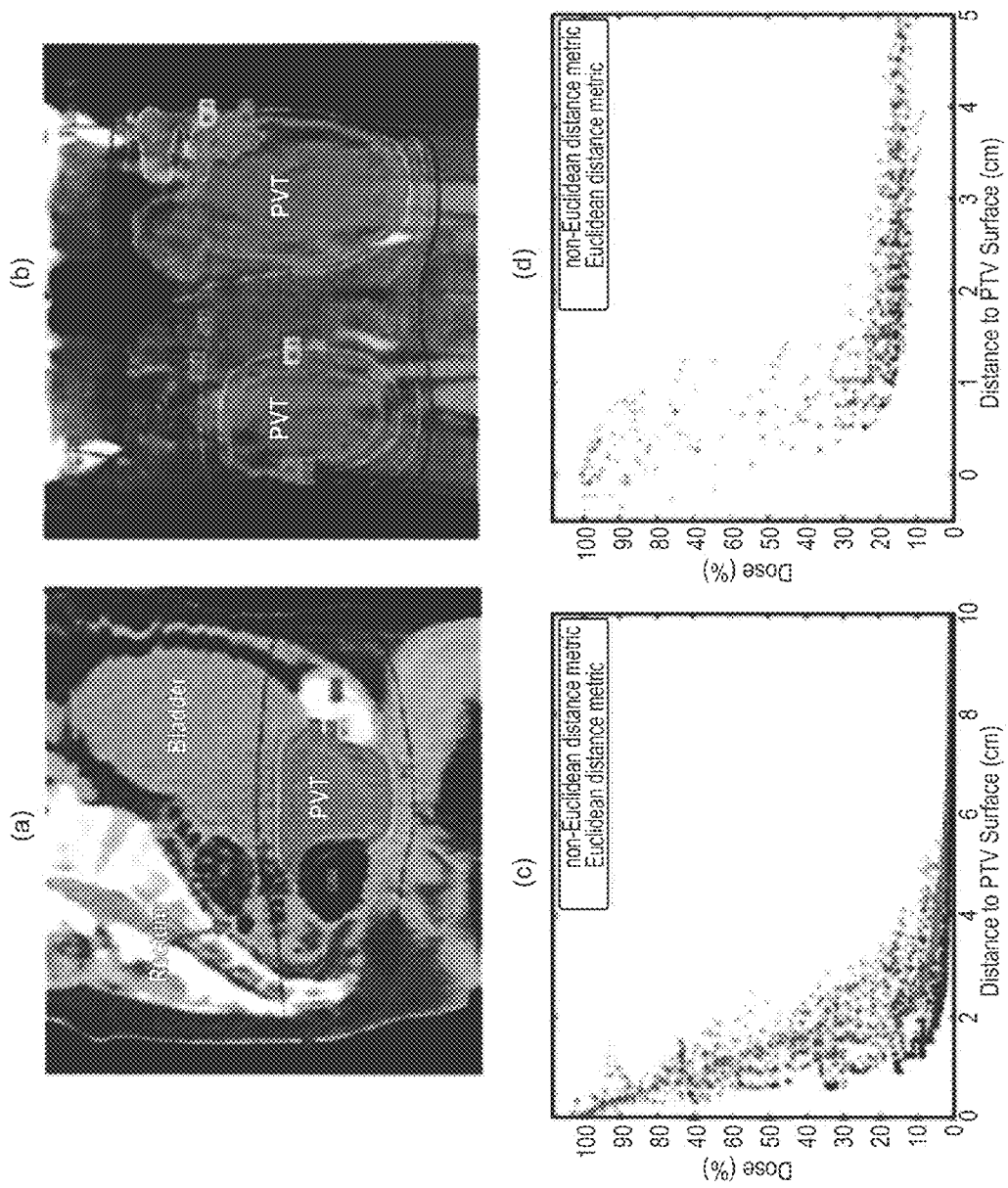
FIG. 23, which depicts (a) sagittal CT image of a prostate plan showing the contours of PTV, bladder, and rectum overlaid with isodose lines, (b) coronal CT image of a HN plan showing the contours of PTV, left and right parotids overlaid with isodose lines, (c) and (d) scatter plots of the correlation between dose and distance to PTV surface by the Euclidean distance metric and the non-Euclidean distance metric for the voxels inside (c) bladder in the prostate plan and (d) right parotid in the HN plan.

Function $f(v_i, \text{PTV})$ is a modification to the Euclidean distance metric which increases the dose fall-off for the voxels outside the primary treatment fields and thus reduce the spread of dose-distance correlation, as shown in (c) and (d) of FIG. 23.

The DTHs and DVHs are continuous functions of distance and dose, respectively. Discretization of these functions results in high dimensional data. Principal component analysis (PCA) is applied to DVHs and DTHs to reduce their dimensions and select the most significant features. With PCA, much of the variability of the histograms can be explained by a small number of principle components. In this study, the first three components of the principal component scores (PCS) were selected as anatomical features.

Once the principal components of the DTH and DVH are extracted by PCA, the principal component scores of the individual DTHs and DVHs of the training datasets are mapped to a few anatomical and dose-volume features. The study involved the systematic analysis of the correlation between these patient anatomical features and the corresponding dose volume features. A stepwise multiple regression method was utilized to perform this analysis. The stepwise regression method adds in most significant anatomical factor to the model and eliminates the least significant one at each step of regression, so that only the significant factors are included in the regression analysis to account for the nonlinear effect between two feature spaces. The significance factors were identified with p-value <0.05. The significance of each individual anatomical feature is represented by the coefficient of partial determination, which measures the correlation between that factor and the residual part of the DVH variation not explained by the factors already included in the model.

To assess how well the selected anatomical features can account for the inter-patient organ-sparing variations, the DVHs calculated from the final regression model were compared with the actual DVHs of each patient's plan in the validation dataset (24 prostate plans and 24 HN plans). The two sets of the DVH curves were plotted and compared. Several specific DVH indices are selected for additional analysis. Specifically, V99%, V85%, and V50% (volumes corresponding to percent prescription dose) of the bladder and rectum were examined for prostate plans and median dose to the parotid were examined for HN plans.

Figure 24B:
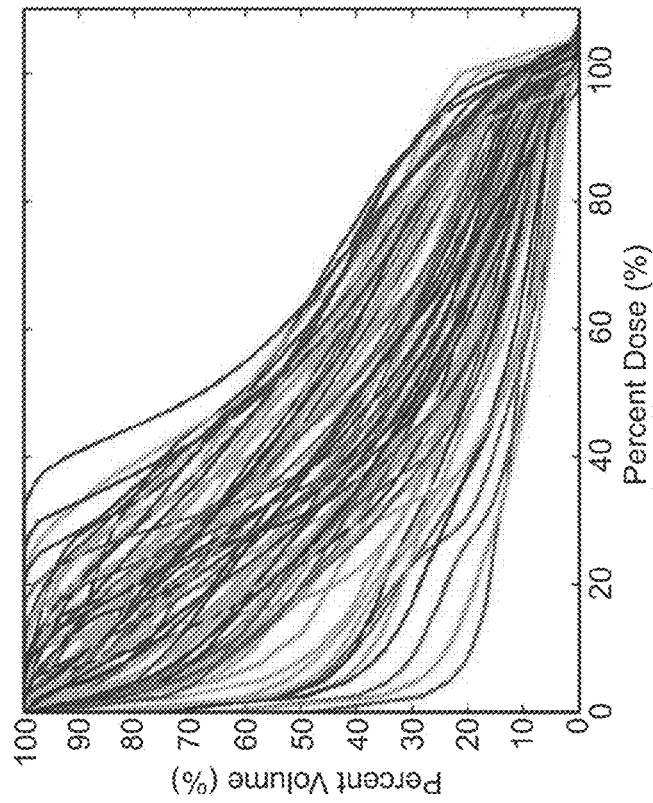
FIGS. 24A-24D are graphs of DVH histograms for the prostate and HN plans.
Figure 24A:
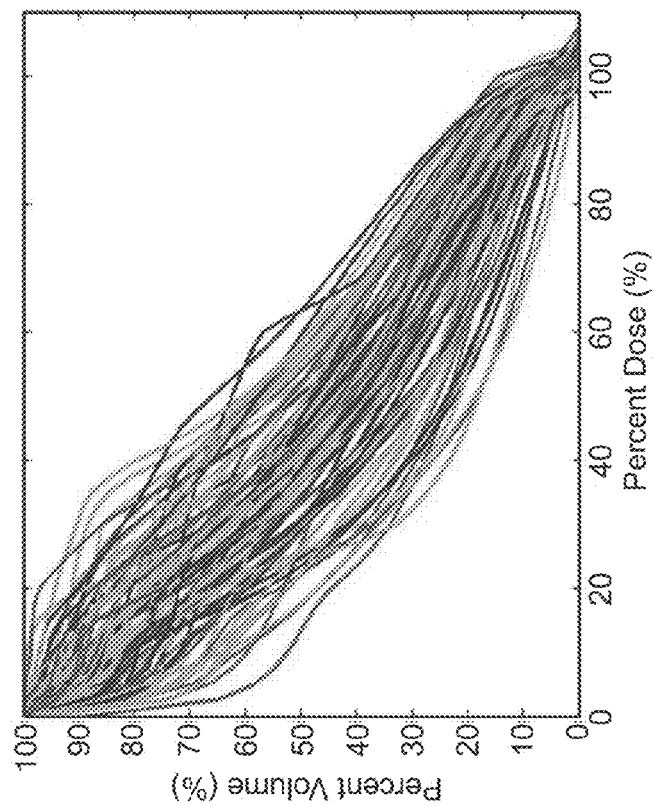
Figure 24D:
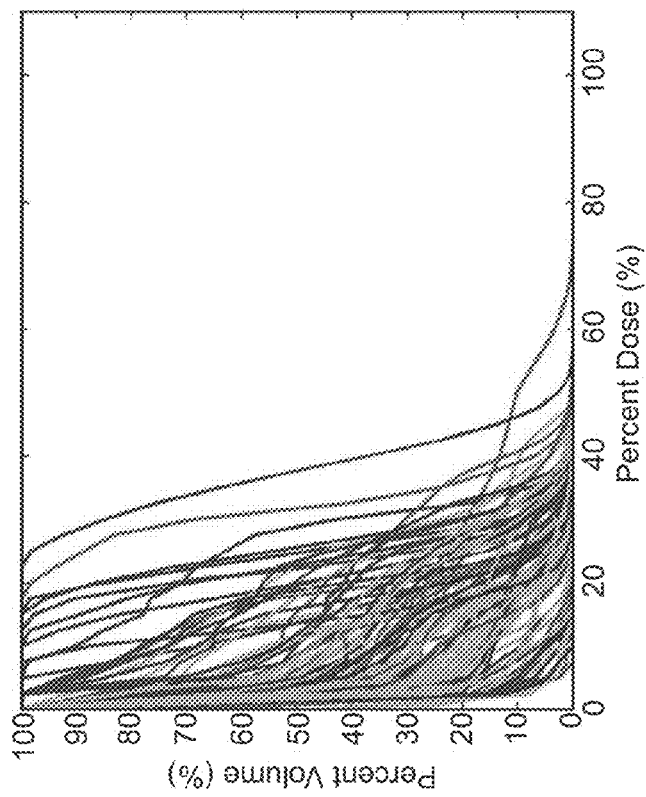
Figure 24C:
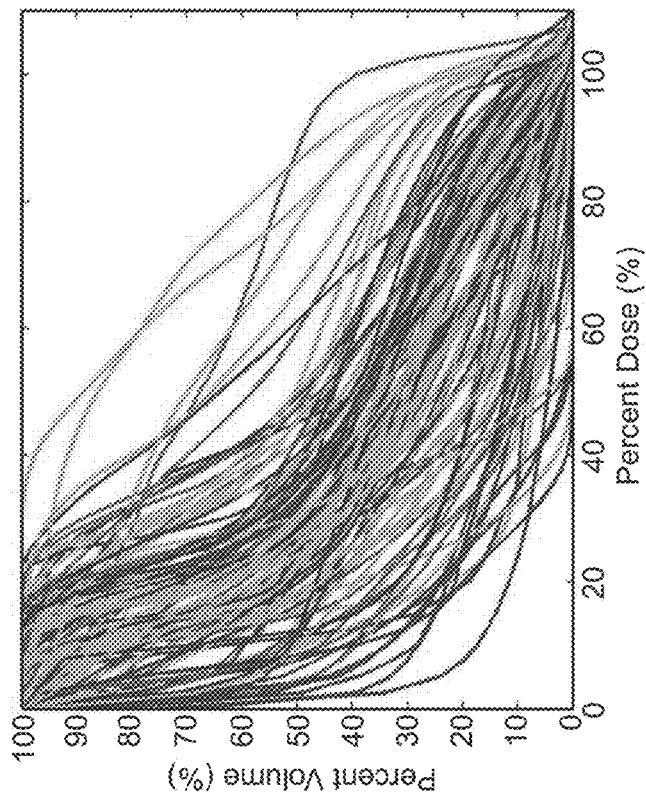

Regarding characterization of the training datasets, the DVH distributions for bladder, rectum, parotids, and brainstem in the training sets are shown in FIGS. 24A-24D, which illustrate graphs of DVH histograms for the prostate and HN plans. The DVHs are grayscale-coded according to the three volume ranges of the OARs. FIG. 24A corresponds to bladder. FIG. 24B corresponds to rectum. FIG. 24C corresponds to parotids. FIG. 24D corresponds to brainstorm (cc=1 cm$^3$). The numbers of plans within the three ranges are approximately 1:2:1 from lowest to highest volume range. As shown, the distribution of the OAR sparing covers a wide range of dose-volume correspondences.

There is a general tendency that the plans with the smallest OAR volume have higher dose indices, while those with largest OAR volume correlate with lower dose indices (as shown in FIGS. 24A-24D). However, the intertwined DVH curves also suggest that the volume information alone is not sufficient to represent all the anatomical influence on the dose distribution in the OARs.

Figure 25:
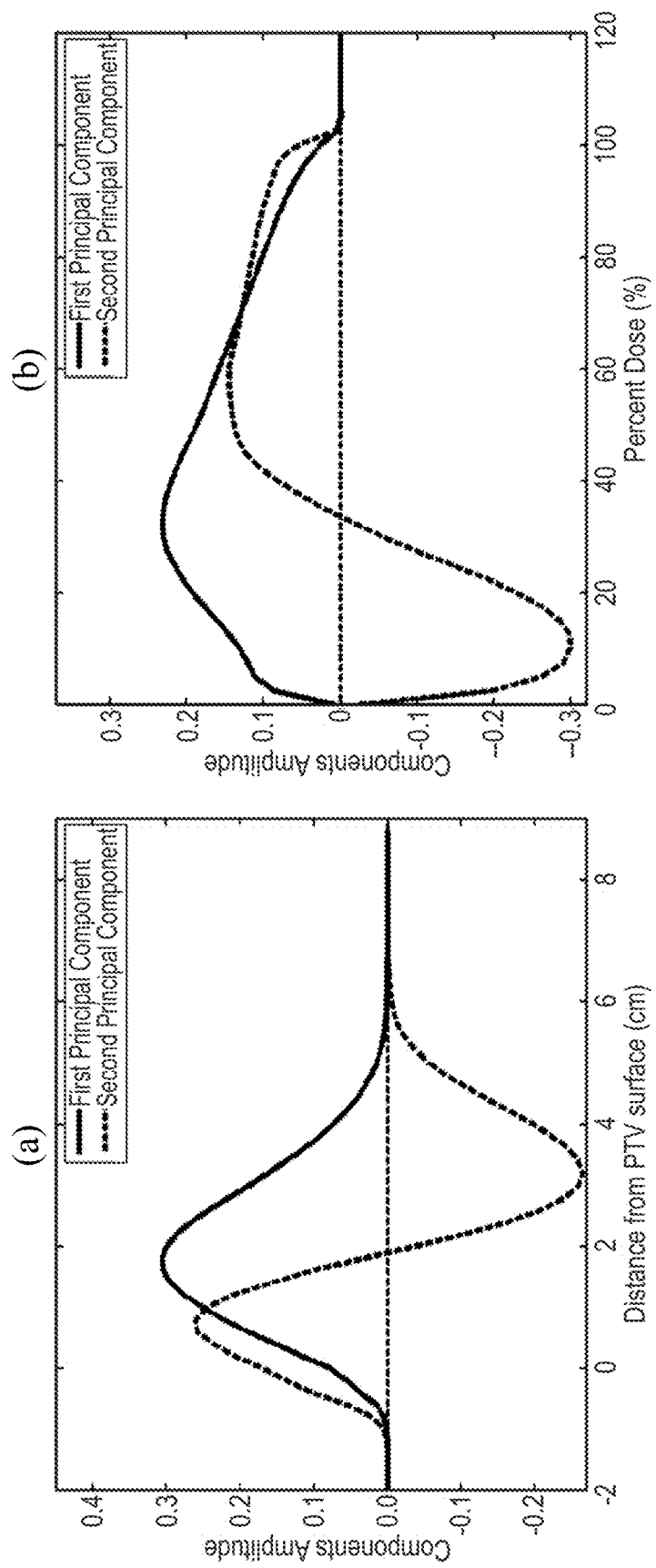
FIG. 25 are graphs showing the principal components for (a) rectum and (b) rectum DVH.

The PCA analysis shows that the most significant three components of PCS can explain more than 95% of the variation of the DVH of all OARs and the most significant three components of DTH PCS can represent the DTH variation at the same level for both datasets. As an example, the coefficients of the first two principal components of rectum DTH and DVH are shown in FIG. 25, which illustrates graphs showing the principal components for (a) rectum and (b) rectum DVH. Each component of the coefficient vector measures the importance of the corresponding data point or histogram bin to the principal component. As can be observed from the figure, the first principal component represents a unidirectional contribution by all data points with one extreme value. It suggests that the first principal component is associated with a single volume value of the dose or distance in DVH and DTH, respectively. On the other hand, the second principal component has two extreme values with opposite signs. This suggests that the second principal component can be interpreted as the interaction of fractional volumes at two different dose or distance bins, or in other words, it is associated with the fractional volume within these two extreme dose or distance values.

Figure 26:
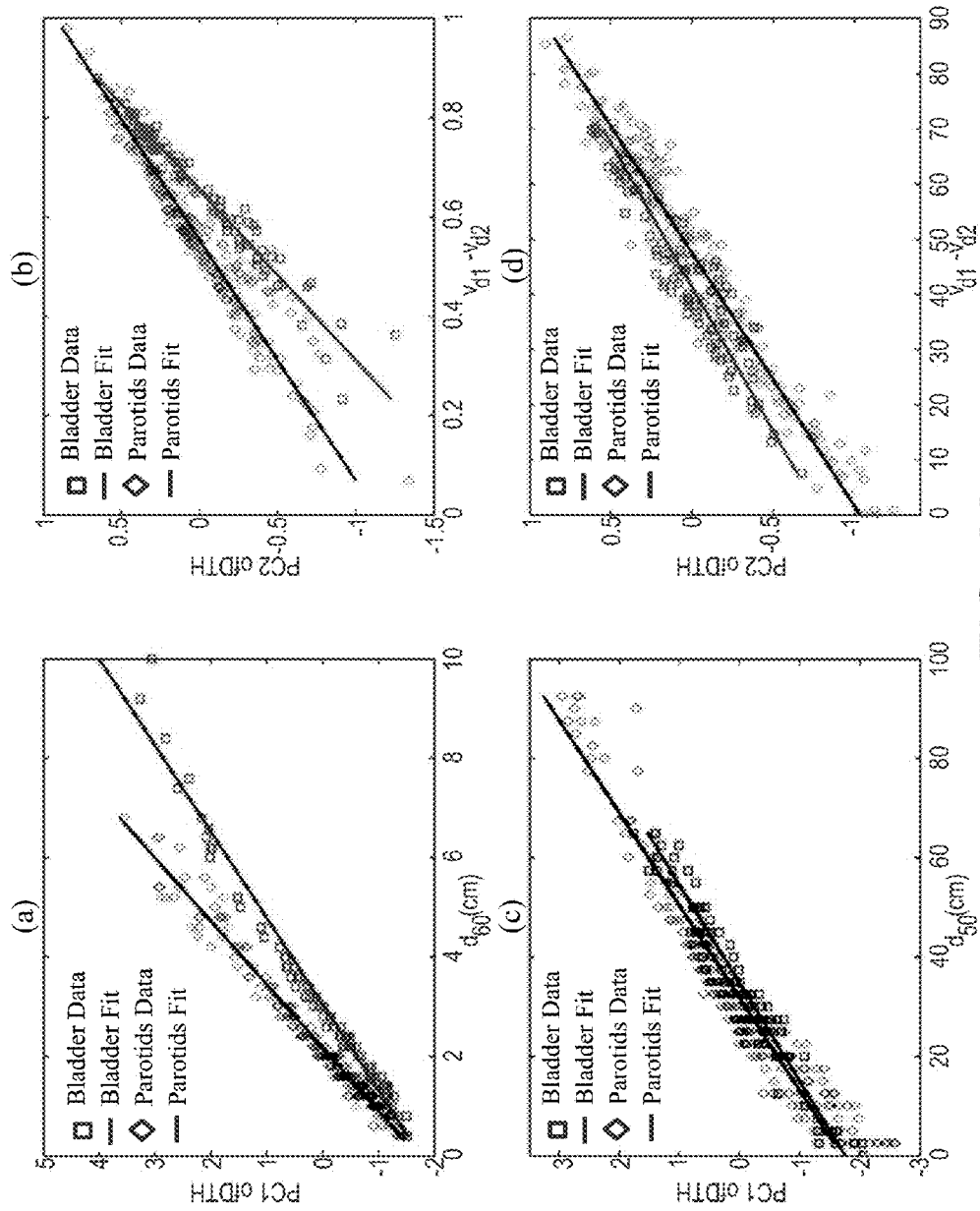
FIG. 26 shows graphs of (a) correlation between PCS1 of bladder and parotid DTH and the distance corresponding to 60% of OAR volume, (b) correlation between PCS2 of bladder and parotids DTH and the average gradient of the DTH within a distance range d1 to d2, (c) correlation between PCS1 of bladder and parotid DVH and the dose corresponding to 50% of OAR volume (D50), and (d) correlation between PCS2 of bladder and parotids DVH and the average gradient of the DVH within a dose range D1 to D2.

Subsequently, the physical meanings of the principal components scores of the DTHs and DVHs are examined by correlating them with dosimetric and anatomical parameters. As shown in FIG. 26 and Table III below, the first principal component score (PCS1) of the DTH is found to be strongly correlated with the distance corresponding to 60% OAR volume (d$_{60}$) for most OARs. It is also closely related to the median distance (d$_{50}$) between the PTV and the OAR. The correlation drops steeply at other distance values. For simplicity, "median distance" is used to refer to both effects in the rest of the analysis hereafter. FIG. 26 shows graphs of (a) correlation between PCS1 of bladder and parotid DTH and the distance corresponding to 60% of OAR volume, (b) correlation between PCS2 of bladder and parotids DTH and the average gradient of the DTH within a distance range d1 to d2, (c) correlation between PCS1 of bladder and parotids DVH and the dose corresponding to 50% of OAR volume (D50), and (d) correlation between PCS2 of bladder and parotids DVH and the average gradient of the DVH within a dose range D1 to D2.

TABLE III

Correlation between principal component scores of DTH and DVH and the patient anatomy and dose-volume distribution indices

| Principle Component Scores | | Patient Anatomy and Dose-Volume Distribution Indices | Correlation Coefficient R |
|---|---|---|---|
| Bladder | DTH PCS1 | d60 | 0.99 |
| | DTH PCS2 | $V_{7.2}$-$V_{0.8}$* | 0.98 |
| | DVH PCS1 | d50 | 0.97 |
| | DVH PCS2 | $V_{10}$-$V_{50}$** | 0.94 |
| Rectum | DTH PCS1 | d60 | 0.98 |
| | DTH PCS2 | $V_{4.0}$-$V_{0.8}$* | 0.93 |
| | DVH PCS1 | d50 | 0.97 |
| | DVH PCS2 | $V_{10}$-$V_{50}$** | 0.94 |
| Parotids | DTH PCS1 | d60 | 0.99 |
| | DTH PCS2 | $V_{4.8}$-$V_{1.4}$* | 0.96 |
| | DVH PCS1 | d50 | 0.95 |
| | DVH PCS2 | $V_{10}$-$V_{50}$** | 0.96 |
| Brainstem | DTH PCS1 | d60 | 0.99 |
| | DTH PCS2 | $V_{4.8}$-$V_{2.1}$* | 0.99 |
| | DVH PCS1 | d50 | 0.94 |
| | DVH PCS2 | $V_5$-$V_{20}$** | 0.89 |

*The notation $V_{d1}$-$V_{d2}$ represents the fraction of OAR volume between two distance values d1 (cm) and d2 (cm).
**The notation $V_{D1}$-$V_{D2}$ represents the fraction of OAR volume between two percent dose values D1 ad D2.

The same figure and table also show that the PCS2 of DTH has a strong correlation with the fraction of OAR volume located within an OAR specific distance range from the PTV. The distance ranges for bladder, rectum in prostate plans and parotids, brainstem in HN plans are listed in Table III. For the other OARs in the HN plans, the distance ranges are: from 0.2 cm to 4.0 cm for mandible, from 1.2 cm to 4.8 cm for oral cavity, from 0.5 cm to 4.8 cm for larynx, from 0.2 cm to 2.1 cm for pharynx, and from 2.5 cm to 24 cm for spinal cord. It is noted that the fraction of volume within a distance range $[r_l, r_u]$, $V[r_1, r_u]$, is proportional to the average slope of DTH $\overline{G_{DTH}}$ in this range:

$$\overline{G_{DTH}} = \frac{1}{r_u - r_i} \int_{r_i}^{r_u} V'(r) \, dr$$

$$= \frac{1}{r_u - r_i} [V(r_u) - V(r_i)]$$

$$= \frac{1}{r_u - r_i} V_{[r_i, r_u]}.$$

This suggests that the PCS2 of DTH represents its dominant gradient.

Similar to DTH, the first DVH PCS (PCS1) and the D$_{50}$ (dose to 50% OAR volume) have strong correlation, suggesting that it represents the median dose in the OAR. The PCS2 of DVH has strong correlation with the portion of volume within a dose range, or equivalently, the average gradient of the DVH on this range. For the bladder and rectum in prostate plans and the parotids in HN plans, the range is between 10% and 50% of the prescribed dose where the largest variations of DVH gradient occur. The corresponding dose ranges for the DVH PCS2 of the OARs which are not listed in Table III are: from 30% to 80% for mandible, from 2% to 72% for oral cavity, from 5% to 35% for larynx, from 45% to 90% for pharynx, and from 5% to 45% for spinal cord. The different dose range represents the stair-like shape of the OAR DVH by four-field conformal treatment plans.

The significant factors which affect OAR dose sparing were identified by stepwise multiple regression model.

These factors and their determination coefficients for bladder and rectum in the prostate plans and parotids, oral cavity, and brainstorm in the HN plans are listed in Table IV below as examples.

TABLE IV

Significant anatomical features contributing to the OAR DVH PCS

| Bladder DVH PCS1 | | Bladder DVH PCS2 | |
| --- | --- | --- | --- |
| Significant Factors | $R^2$ | Significant Factors | $R^2$ |
| DTH PCS1 | 0.81 | Out-of-field Volume | 0.50 |
| $2^{nd}$ Order of DTH PCS1 | 0.22 | Overlap Volume | 0.33 |
| Combined | 0.88 | DTH PCS2 | 0.30 |
| | | Combined | 0.85 |

| Rectum DVH PCS1 | | Rectum DVH PCS2 | |
| --- | --- | --- | --- |
| Significant Factors | $R^2$ | Significant Factors | $R^2$ |
| DTH PCS1 | 0.59 | DTH PCS2 | 0.32 |
| Volume of Rectum | 0.12 | Out-of-field Volume | 0.32 |
| Overlap Volume | 0.08 | Overlap Volume | 0.12 |
| Combined | 0.68 | DTH PCS3 | 0.12 |
| | | Combined | 0.69 |

| Parotid DVH PCS1 | | Parotid DVH PCS2 | |
| --- | --- | --- | --- |
| Significant Factors | $R^2$ | Significant Factors | $R^2$ |
| DTH PCS1 | 0.78 | Out-of-field Volume | 0.46 |
| Volume of Parotid | 0.20 | DTH PCS2 | 0.28 |
| Overlap Volume | 0.19 | Overlap Volume | 0.10 |
| Combined | 0.88 | Combined | 0.77 |

| Oral Cavity DVH PCS1 | | Oral Cavity DVH PCS2 | |
| --- | --- | --- | --- |
| Significant Factors | $R^2$ | Significant Factors | $R^2$ |
| DTH PCS1 | 0.84 | DTH PCS2 | 0.56 |
| PTV Volume | 0.27 | Out-of-field Volume | 0.19 |
| Combined | 0.9 | $2^{nd}$ Order of DTH | 0.15 |
| | | Combined | 0.8 |

| Brainstem DVH PCS1 | | Brainstem DVH PCS2 | |
| --- | --- | --- | --- |
| Significant Factors | $R^2$ | Significant Factors | $R^2$ |
| Out-of-field Volume | 0.85 | DTH PCS1 | 0.15 |
| PTV Volume | 0.16 | DTH PCS2 | 0.03 |
| Brainstem DTH PCS1 | 0.09 | Combined | 0.15 |
| Combined | 0.92 | | |

The partial determination of coefficient represents each feature's individual contribution to PCS1 and PCS2 of the DVH and the multiple determination coefficients represent the overall contribution by all these factors combined. DTH PCS1 is the most significant anatomical factor contributing to the DVH PCS1 of both bladder and rectum in the prostate plans and all the OARs in the HN plans other spinal cord and brainstem. And the most significant factors affecting DVH PCS2 of these OARs are DTH PCS2 and the fraction of OAR volume outside the primary treatment fields (out-of-field volume). As to the other two OARs in the HN plans, the spinal cord and brainstorm, the most significant anatomical factor for their DVH PCS1 is the fraction of the out-of-field OAR volume.

The multiple determination coefficients for the DVH PCS of the OARs which are not listed in Table IV are: $R^2=0.91$ for larynx DVH PCS1, $R^2=0.64$ for larynx DVH PCS2, $R^2=0.9$ for pharynx DVH PCS1, $R^2=0.53$ for pharynx DVH PCS2, $R^2=0.92$ for mandible DVH PCS1, $R^2=0.7$ for mandible DVH PCS2, $R^2=0.86$ for spinal cord DVH PCS1, and $R^2=0.15$ for spinal cord DVH PCS2. Because the second principle components only contribute to less than 15% of the inter-patient DVH variation, the above set of anatomical features combined have captured significant portions of DVH variations for all the OARs in prostate and HN plans.

Figure 27A:
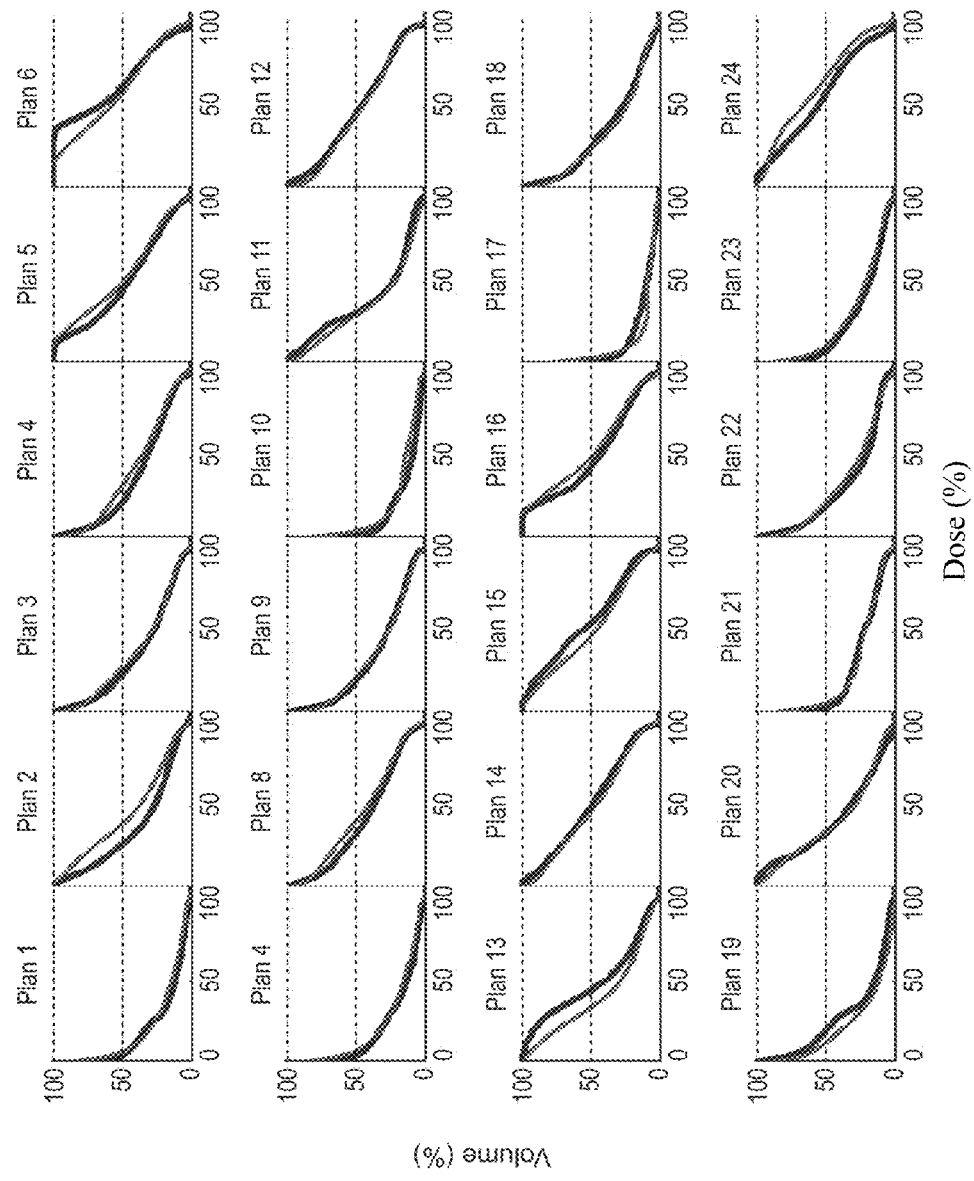
FIGS. 27A-27C are graphs showing comparisons of actual DVHs and the model predicted DVHs.
Figure 27B:
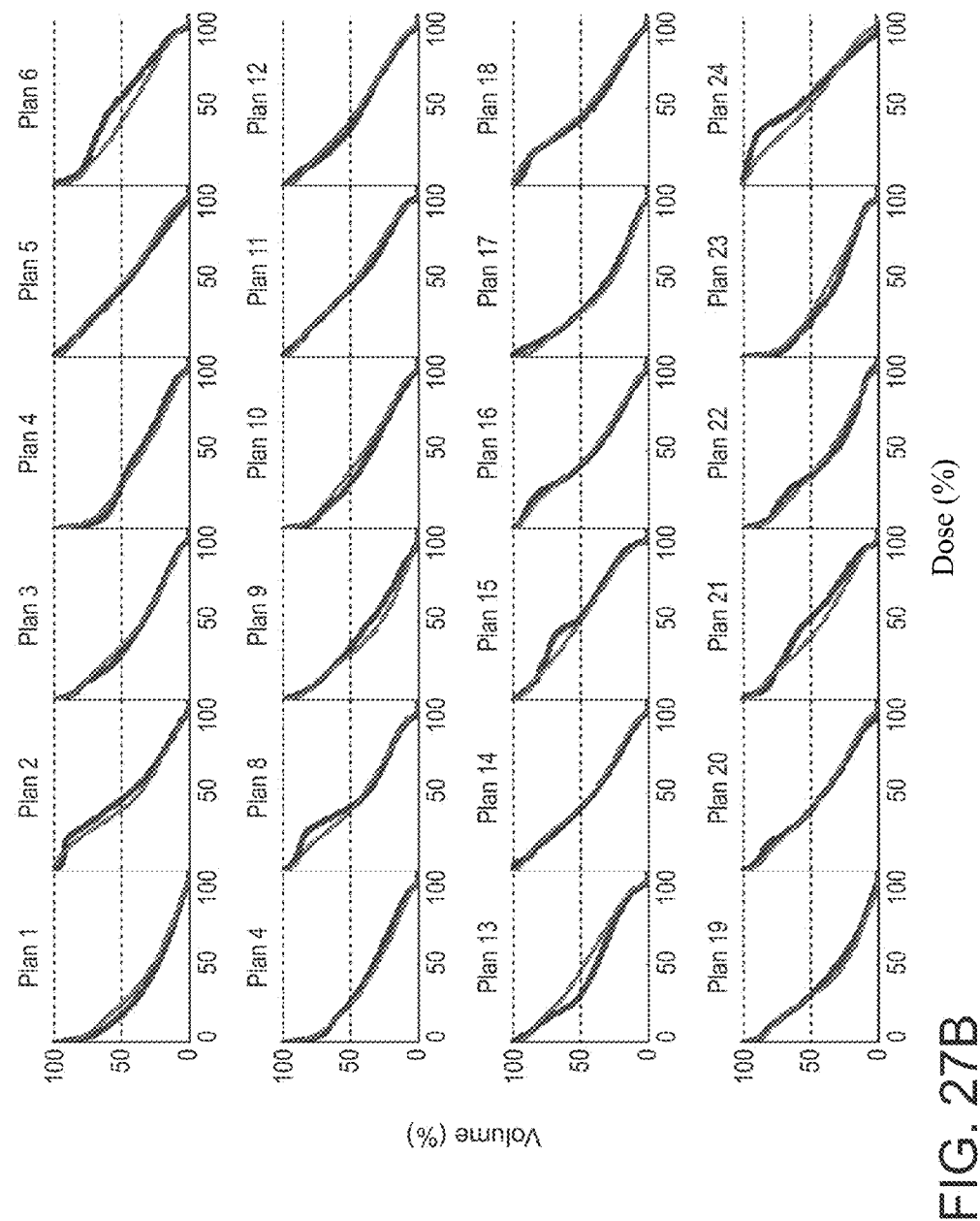
Figure 27C:
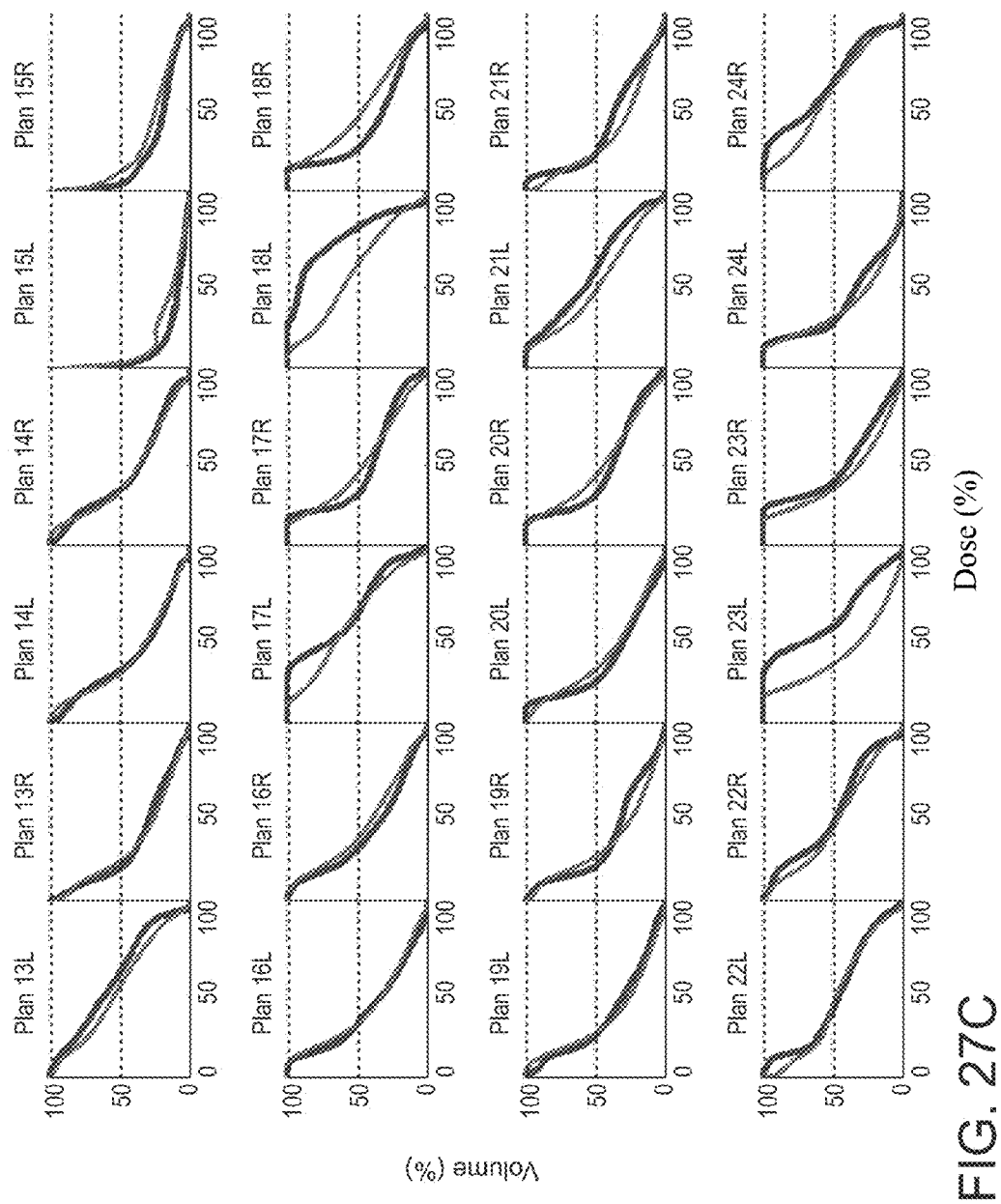

The DVHs of bladder, rectum, and parotids for pans in the validation datasets are calculated by the multiple regression models trained by the training dataset. These model-predicted DVHs are compared to their corresponding DVHs in the actual plans to assess the effectiveness of the factors identified in this study. If the factors used in the trained regression model capture significant portions of the inter-patient OAR dose sparing variation, the model can predict the DVHs in the validation datasets. The comparison of DVHs for a subset of the validation plans are shown in the graphs of FIGS. 27A-27C, which illustrate graphs showing comparisons of actual DVHs and the model predicted DVHs. The plans are a subset of the validation data. Graph (a), (b) and (c) show bladder, rectum, and parotid, respectively. The left and right parotids of the same plan are marked by L and R, respectively. The left and right parotids in HN plans are plotted separately and are marked by L and R, respectively, in the figure.

Figure 28:
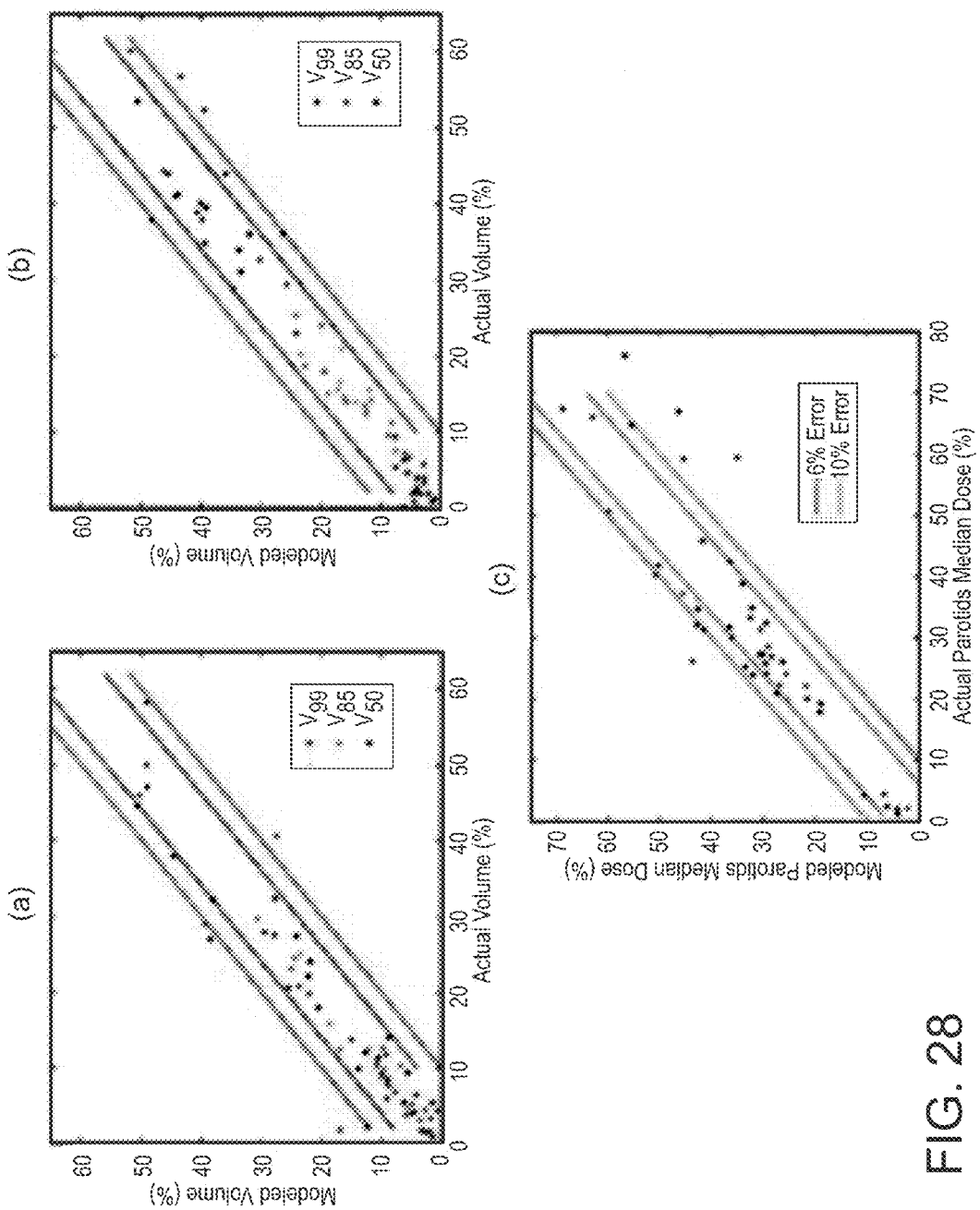
FIG. 28 are graphs showing correlations between the modeled values and the actual plan values for all the validation cases.

To quantify the level of agreement between the modeled DVHs and the actual plan DVHs, specific dose-volume indices are extracted and analyzed. For the prostate plans, the volumes corresponding to 99%, 85%, and 50% of prescribed dose in the modeled plans were compared with those values in the actual plans. Parotid median dose was used for comparison of the HN plans. The correlations between the modeled values and the actual plan values for all the validation cases are plotted in FIG. 28, along with the error bands corresponding to 6% and 10% OAR volume for the prostate plans and 6% and 10% prescription dose for HN plans. It was found that for both the bladder and rectum, 17 out of 24 plans (71%) are within 6% error band and 21 (85%) are within 10% error band; for the parotids, the median dose values for 30 parotids out of 48 (63%) are within 6% error band, and the values in 40 parotids (83%) are within 10% error band.

A series of anatomical features have been analyzed and measured to establish an inter-patient variation model that quantifies the patient specific organ sparing. Based on the anatomical and dosimetric meanings of the principal component scores, the important anatomical features for the OAR dose sparing in prostate and HN plans are: the influence of median distance on median dose, the influence of DTH gradient and out-of-filed OAR volume portion on the gradient of DVH. In HN plans, the brainstem and spinal cord DVHs have different dependence on the anatomical features from the other OARs. The out-of-field volume portion is the dominant factor contributing to brainstem and spinal cord DVH PCS1 (equivalent to mean dose). One of the spatial characteristics attributing to this difference is that brainstem and spinal cord usually extend out of the treatment fields; hence, the ratio of out-of-field volume over entire volume may shift the overall DVH curve on the dose axis.

Figure 29:
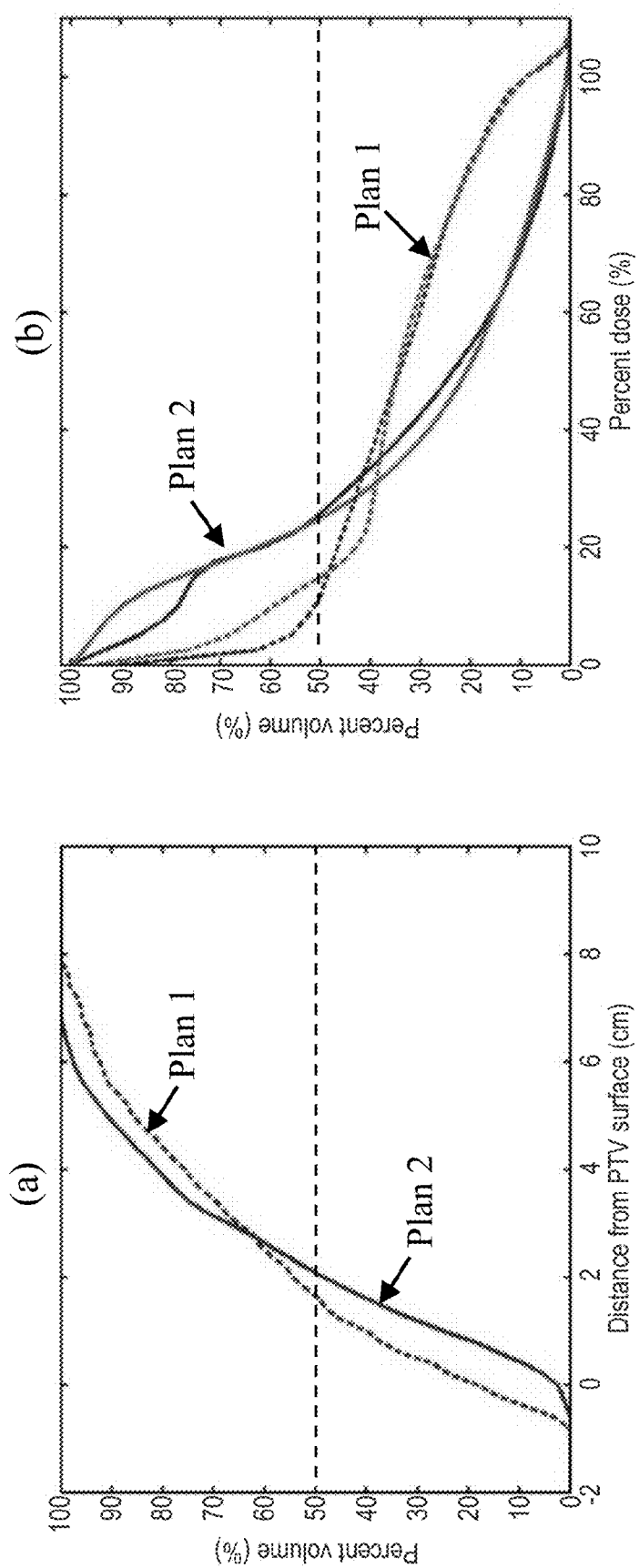
FIG. 29 are graphs of the DTHs and DVHs for the parotids in two HN plans showing crossovers where (a) is the DTH crossing, and (b) is the DVH crossing.

It is noted that DTHs and DVHs have crossovers as shown in FIG. 29, which illustrates graphs of the DTHs and DVHs for the parotids in two HN plans showing crossovers where (a) is the DTH crossing, and (b) is the DVH crossing. This suggest the simple monotomic relationships based on one or a few DTH points may not be sufficient to model the inter-patient variations on organ sparing, and high definition relations may potentially exist and be applied. In this study, the entire DTH and DVH curves are taken into consideration in the feature learning process and high dimension relations are formulated, allowing the inter-patient variation of the OAR DVH be represented cross the entire volume ranges.

For the plans with large prediction errors, two main source of errors may occur. Either these plans have features not yet captured by the current model or these plans are sub-optimal plans. One of the clinical features that has not been taken into account is the tradeoffs in organ sparing. The effect of the tradeoff can be appreciated with prostate plans #2, #13, and #24 where the bladder and rectum dose sparing exhibiting tradeoffs (FIG. 27). These plans have characteristics that the planned DVH is lower than the modeled DVH in one OAR but is higher in another OAR. The DVHs of the right and left parotids in HN plan #18 has the same feature, indicating tradeoff between the left and right parotids. Besides the tradeoff plans, other plans falling below the error bands may potentially be sub-optimal plans and may potentially benefit from re-planning using modeled DVHs as references.

In accordance with embodiments, mathematical models may be used to describe the quantitative correlations between patient anatomical features and the achievable OAR dose sparing. A step-wise multiple regression method may be used to select the significant patient features which influence the OAR dose sparing in the training plans. In one study, two predictive models were developed. The trade-off model was trained with cases in which physicians models were developed. The trade-off model was trained with cases in which physicians prescribed trade-off preferences, while the standard model was trained with the remainder of cases that do not have trade-off prescribed. The final model is the combination of these two models. The final predictive model (combined model) takes into account the trade-off by switching between the standard and tradeoff models according to their trade-off criteria.

Figure 30:
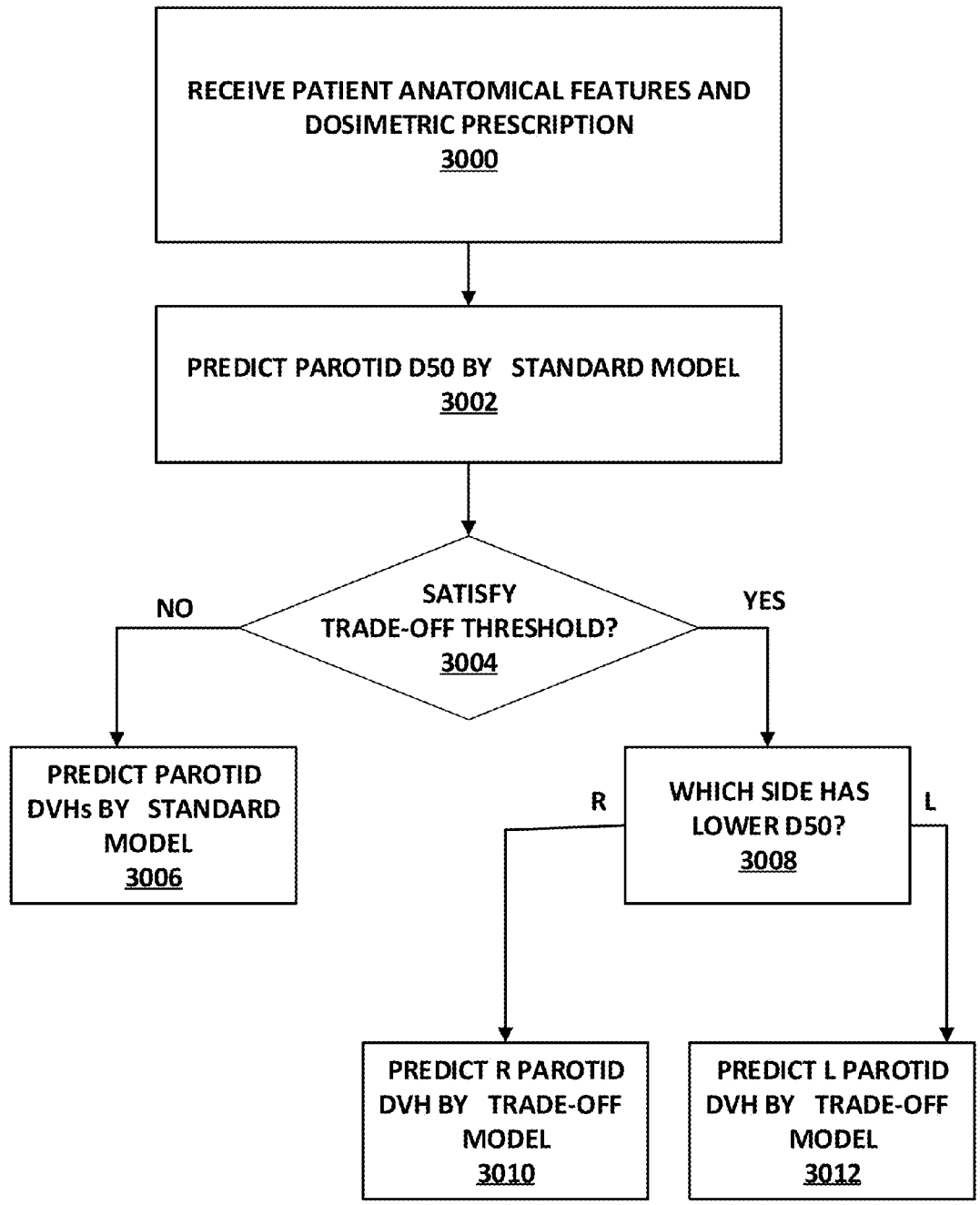
FIG. 30 is a flowchart of an example method for radiation therapy planning in accordance with embodiments of the present disclosure.

FIG. 30 is a flowchart of an example method for radiation therapy planning in accordance with embodiments of the present disclosure. In this example, the method is described as being implemented by the training modeling subsystem 104, although it should be understood that the method may alternatively be implemented by any suitable computing device. It should also be understood that the steps or tasks depicted in FIG. 30 can be performed simultaneously or in a different order than that depicted.

Referring to FIG. 30, the method includes acquiring or receiving 3000 patient anatomical features and dosimetric prescription. The method includes predicting 3002 parotid D50 by a standard model. Further, the method includes determining 3004 whether a trade-off threshold is satisfied. The method also includes predicting 3006 parotid DVHs by the "standard model" in response to determining that the trade-off threshold is not satisfied. Further, the method includes determining 3008 which side has a lower D50 in response to determining that the trade-off threshold is satisfied. In response to determining that the right side has a lower D50, the right parotid DVH is predicted 3010 by the "trade-off" model. In response to determining that the left side has a lower D50, the left parotid DVH is predicted 3012 by the "trade-off" model.

Figure 31:
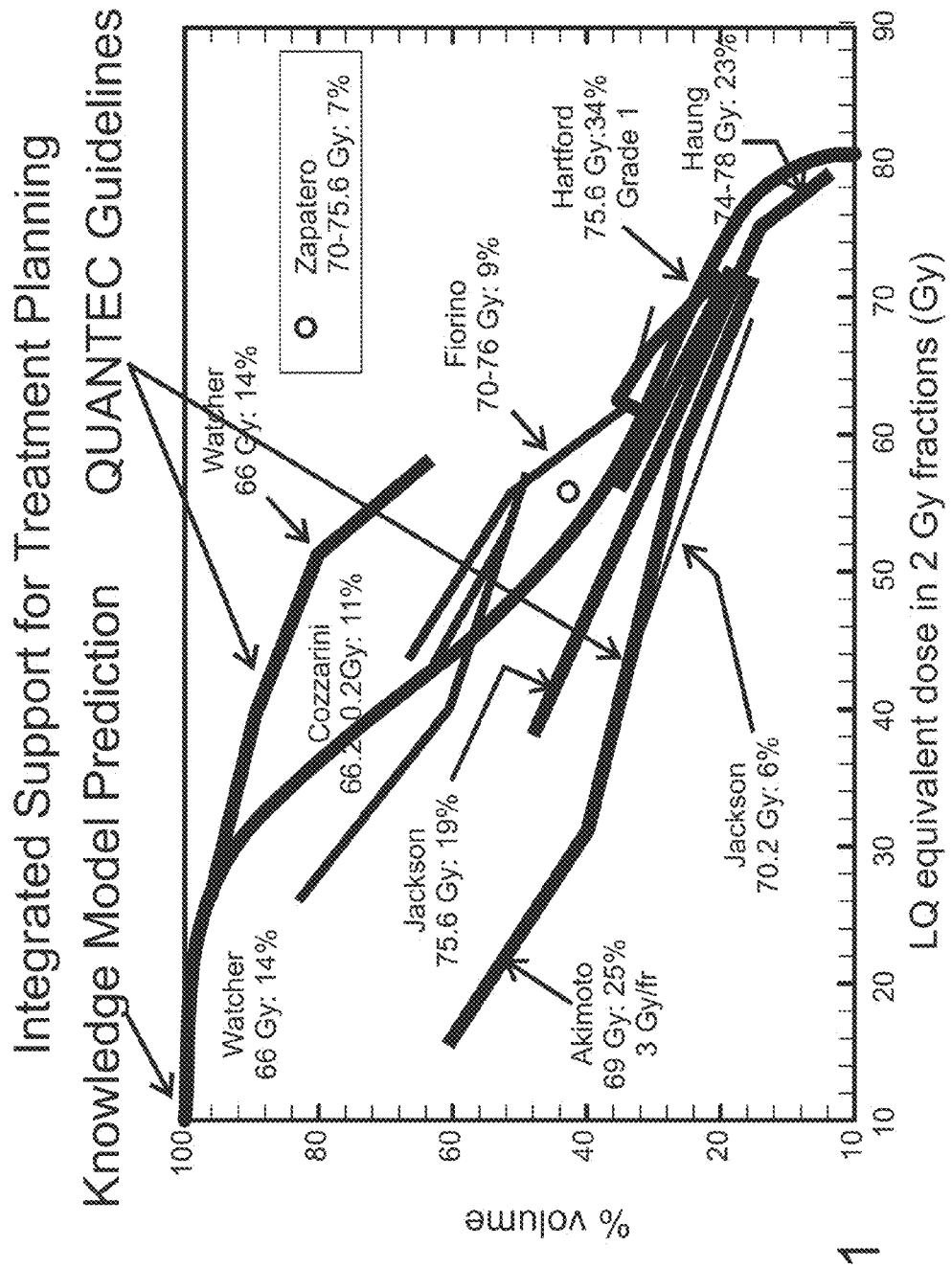
FIG. 31 depicts a graph showing integrated computerized knowledge from various models.

FIG. 31 depicts a graph showing integrated computerized knowledge from various models. Particularly, the figure shows that the system integrates computerized knowledge from all models in an intuitive and interactive ontology framework. The knowledge model prediction of patient-specific organ sparing is presented with population-based organ DVHs and toxicity data from guidelines, clinical trials, etc.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flow chart illustrations and/or block diagrams of methods, apparatus (systems), and computer program products according to embodiments of the subject matter. It will be understood that each block of the flow chart illustrations and/or block diagrams, and combinations of blocks in the flow chart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flow chart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flow chart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flow chart and/or block diagram block or blocks.

The flow chart and block diagrams in the Figures illustrate the architecture, functionality, and operation of possible implementations of systems, methods, and computer program products according to various embodiments of the present subject matter. In this regard, each block in the flow chart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flow chart illustration, and combinations of blocks in the block diagrams and/or flow chart illustration, can be implemented by special purpose hardware-based systems that perform the specified functions or acts or carry out combinations of special purpose hardware and computer instructions.

Any patents or publications mentioned in this specification are indicative of the levels of those skilled in the art to which the present subject matter pertains. These patents and publications are herein incorporated by reference to the same extent as if each individual publication was specifically and individually indicated to be incorporated by reference.

One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed is:

1. A method comprising:
   at a processor and memory;
   receiving data based on patient information and geometric characterization of one or more organs at risk proximate to a target volume of a patient;
   generating, based on the data and a predictive model, a first set of radiation treatment planning parameters for the patient, wherein the predictive model is integrated with a computerized model of clinical trial data;
   extracting, a set of anatomical points from the geometric characterization of the one or more organs at risk and from the target volume of the patient;
   extracting a set of mean dose volume points from a dose volume histogram of the patient;
   generating, based on the data, the extracted set of anatomical points, the extracted set of mean dose volume points, and the predictive model, a second set of radiation treatment planning parameters for treating the patient, the first set of radiation treatment planning parameters being different than the second set of radiation treatment planning parameters;
   presenting the first and second radiation treatment planning parameters via a user interface.

2. The method of claim 1, wherein the patient information includes one or more of patient image, patient organ contour information, target volume contour information, and clinical parameters.

3. The method of claim 1, wherein the geometric characterization associates each of a plurality of distances from the target volume with a respective percentage for a volume of the one or more organs at risk.

4. The method of claim 1, wherein the data comprises a size of the target volume and respective sizes and shapes of the one or more organs at risk.

5. The method of claim 1, wherein the data comprises information about one of radiation treatment knowledge, experience, and preferences, and computerized models of published clinical trials results and guidelines.

6. The method of claim 1, further comprising computing the geometric characterization of the patient.

7. The method of claim 1, wherein the radiation treatment planning parameters are represented by at least one of a dose distribution and the dose volume histogram.

8. The method of claim 1, wherein the data includes a geometric characterization of the target volume with respect to one or more organs at risk.

9. The method of claim 1, further comprising storing the data.

10. The method of claim 1, further comprising training the predictive model on a plurality of input-output mappings, wherein an output of each input-output mapping is based on a dose distribution and the dose volume histogram for the respective patient, and wherein an input of each input-output mapping comprises one or more data that are based on the geometric characterization.

11. A system comprising:
  at least one processor and memory configured to:
    receive data based on patient information and geometric characterization of one or more organs at risk proximate to a target volume of a patient;
    generate, based on the data and a predictive model, a first set of radiation treatment planning parameters for the patient, wherein the predictive model is integrated with a computerized model of clinical trial data;
    extract, a set of anatomical points from the geometric characterization of the one or more organs at risk and from the target volume of the patient;
    extract a set of mean dose volume points from a dose volume histogram of the patient;
    and
    generate, based on the data, the extracted first set of anatomical points, the extracted set of mean dose volume points, and the predictive model, a second set of radiation treatment planning parameters for treating the patient, the first set of radiation treatment planning parameters being different than the second set of radiation treatment planning parameters; and
  a user interface configured to present the first and second radiation treatment planning parameters.

12. The system of claim 11, wherein the patient information includes one or more of patient image, patient organ contour information, target volume contour information, and clinical parameters.

13. The system of claim 11, wherein the geometric characterization associates each of a plurality of distances from the target volume with a respective percentage for the volume of the one or more organs at risk.

14. The system of claim 11, wherein the data comprises an size of the target volume and respective sizes and shapes of the one or more organs at risk.

15. The system of claim 11, wherein the data comprises information about one of knowledge, experience, and preferences, and computerized models of published clinical trials results and guidelines.

16. The system of claim 11, wherein the at least one processor and memory are configured to compute the geometric characterization of the patient.

17. The system of claim 11, wherein the first set and second set of radiation treatment planning parameters are represented by at least one of a dose distribution and the dose volume histogram.

18. The system of claim 11, wherein the data includes a geometric characterization of the target volume with respect to one or more organs at risk.

19. The system of claim 11, wherein the at least one processor and memory are configured to store the data.

20. The system of claim 11, wherein the at least one processor and memory configured to train a predictive model on a plurality of input-output mappings, wherein an output of each input-output mapping is based on a dose distribution and the dose volume histogram for the respective patient, and wherein an input of each input-output mapping comprises one or more data that are based on the geometric characterization.

21. A computer program product comprising a computer readable storage medium having program instructions embodied therewith, wherein execution of the program instructions by a computing device causes the computing device to:
  receive, by the computing device, data based on patient information and geometric characterization of one or more organs at risk proximate to a target volume of a patient;
  generate, by the computing device, based on the data and a predictive model, a first set of radiation treatment planning parameters for the patient in a treatment model, wherein the predictive model is integrated with a computerized model of clinical trial data;
  extract, by the computing device, a set of anatomical points from the geometric characterization of the one or more organs at risk and from the target volume of the patient;
  extract, by the computing device, a set of mean dose volume points from a dose volume histogram of the patient;
  and
  generate, by the computing device and based on the data, the extracted set of anatomical points, the extracted set of mean dose volume points, second set of dose volume points, and the predictive model, a second set of radiation treatment planning parameters for treating the patient, the first set of radiation treatment planning parameters being different than the second set of radiation treatment planning parameters; and
  present, by the computing device and based on the data, the first and second radiation treatment planning parameters.

* * * * *